US011155601B2

(12) United States Patent
Moses et al.

(10) Patent No.: US 11,155,601 B2
(45) Date of Patent: Oct. 26, 2021

(54) MODIFIED VON WILLEBRAND FACTOR HAVING IMPROVED HALF-LIFE

(71) Applicant: CSL Behring Lengnau AG, Lengnau (CH)

(72) Inventors: Michael Moses, Graevenwiesbach (DE); Stefan Schulte, Marburg (DE); Gerhard Dickneite, Marburg (DE); Uwe Kalina, Marburg (DE); Sabine Pestel, Marburg (DE); Thomas Weimer, Gladenbach (DE)

(73) Assignee: CSL BEHRING LENGNAU AG, Lengnau (CH)

( * ) Notice: Subject to any disclaimer, the term of this patent is extended or adjusted under 35 U.S.C. 154(b) by 266 days.

(21) Appl. No.: 15/555,894

(22) PCT Filed: Mar. 4, 2016

(86) PCT No.: PCT/EP2016/054647
§ 371 (c)(1),
(2) Date: Sep. 5, 2017

(87) PCT Pub. No.: WO2016/142288
PCT Pub. Date: Sep. 15, 2016

(65) Prior Publication Data
US 2018/0051067 A1 Feb. 22, 2018

(30) Foreign Application Priority Data
Mar. 6, 2015 (EP) .................................. 15158065

(51) Int. Cl.
*C07K 14/755* (2006.01)
*A61P 43/00* (2006.01)
*A61P 7/04* (2006.01)

(52) U.S. Cl.
CPC .............. *C07K 14/755* (2013.01); *A61P 7/04* (2018.01); *A61P 43/00* (2018.01)

(58) Field of Classification Search
CPC ........... C07K 14/755; A61P 43/00; A61P 7/04
See application file for complete search history.

(56) References Cited

U.S. PATENT DOCUMENTS

| | | |
|---|---|---|
| 4,444,887 A | 4/1984 | Hoffmann |
| 4,716,111 A | 12/1987 | Osband et al. |
| 4,816,397 A | 3/1989 | Boss et al. |
| 4,816,567 A | 3/1989 | Cabilly et al. |
| 4,970,300 A | 11/1990 | Fulton et al. |
| 5,219,996 A | 6/1993 | Bodmer et al. |
| 5,225,539 A | 7/1993 | Winter |
| 5,413,923 A | 5/1995 | Kucherlapati et al. |
| 5,530,101 A | 6/1996 | Queen et al. |
| 5,545,806 A | 8/1996 | Lonberg et al. |
| 5,565,332 A | 10/1996 | Hoogenboom et al. |
| 5,569,825 A | 10/1996 | Lonberg et al. |
| 5,585,089 A | 12/1996 | Queen et al. |
| 5,625,126 A | 4/1997 | Lonberg et al. |
| 5,633,425 A | 5/1997 | Lonberg et al. |
| 5,658,570 A | 8/1997 | Newman et al. |
| 5,661,016 A | 8/1997 | Lonberg et al. |
| 5,685,570 A | 8/1997 | Newman et al. |
| 5,681,722 A | 10/1997 | Newman et al. |
| 5,693,761 A | 12/1997 | Queen et al. |
| 5,693,762 A | 12/1997 | Queen et al. |
| 5,693,780 A | 12/1997 | Newman et al. |
| 5,807,715 A | 9/1998 | Morrison et al. |
| 5,814,318 A | 9/1998 | Lonberg et al. |
| 5,885,793 A | 3/1999 | Griffiths et al. |
| 5,916,771 A | 6/1999 | Hori et al. |
| 5,939,598 A | 8/1999 | Kucherlapati et al. |
| 6,180,370 B1 | 1/2001 | Queen et al. |
| 7,217,797 B2 | 5/2007 | Hinton et al. |
| 7,217,798 B2 | 5/2007 | Hinton et al. |
| 7,361,740 B2 | 4/2008 | Hinton et al. |
| 7,365,168 B2 | 4/2008 | Hinton et al. |
| 2007/0280931 A1 | 12/2007 | Chen et al. |
| 2010/0113364 A1 | 5/2010 | Turecek et al. |
| 2010/0113365 A1 | 5/2010 | Turecek et al. |
| 2010/0168391 A1 | 7/2010 | Siekmann et al. |
| 2010/0173830 A1 | 7/2010 | Turecek et al. |
| 2010/0173831 A1 | 7/2010 | Turecek et al. |

FOREIGN PATENT DOCUMENTS

| | | |
|---|---|---|
| EP | 0 239 400 A2 | 9/1987 |
| EP | 0 392 745 A2 | 10/1990 |
| EP | 0 519 596 A1 | 12/1992 |
| EP | 0 592 106 A1 | 4/1994 |
| EP | 0 948 544 B1 | 10/1999 |
| WO | WO 1986/01533 A1 | 3/1986 |
| WO | WO 1991/09967 A1 | 7/1991 |
| WO | WO 1991/10741 A1 | 7/1991 |

(Continued)

OTHER PUBLICATIONS

Cleveland Clnic, blood cogaulation disorders, accessed online Oct. 10, 2019.*
L. Hilbert, Expression of two type 2N von Willebrand disease mutations identified in exon 18 of von Willebrand factor gene, 2004 Blackwell Publishing Ltd, British Journal of Haematology, 127, 184-189.*
Mechanisms of Carcinogenesis, section 3, 2008, International Agency for research on Cancer.*
Badirou I, Kurdi M, Legendre P, Rayes J, Bryckaert M, et al. (2012) In Vivo Analysis of the Role of O-Glycosylations of Von Willebrand Factor. PLoS ONE 7(5): e37508. doi: 10.1371/journal.pone.0037508.*
Agata A. Nowak, O-linked glycosylation of von Willebrand factor modulates the interaction with platelet receptor glycoprotein Ib under static and shear stress conditions, Blood, Jul. 5, 2012 vol. 120, No. 1, pp. 214-221.*

(Continued)

*Primary Examiner* — James H Alstrum-Acevedo
*Assistant Examiner* — Erinne R Dabkowski
(74) *Attorney, Agent, or Firm* — Finnegan, Henderson, Farabow, Garrett & Dunner, LLP

(57) ABSTRACT

The invention relates to a modified VWF molecule for use in the treatment of a blood coagulation disorder.

13 Claims, 2 Drawing Sheets
Specification includes a Sequence Listing.

(56) References Cited

FOREIGN PATENT DOCUMENTS

| | | |
|---|---|---|
| WO | WO 1992/01047 A1 | 1/1992 |
| WO | WO 1994/15625 A1 | 7/1994 |
| WO | WO 1996/33735 A1 | 10/1996 |
| WO | WO 1996/34096 A1 | 10/1996 |
| WO | WO 1997/03193 A1 | 1/1997 |
| WO | WO 1997/11957 A1 | 4/1997 |
| WO | WO 1997/40145 A1 | 10/1997 |
| WO | WO 1998/16654 A1 | 4/1998 |
| WO | WO 1998/24893 A2 | 6/1998 |
| WO | WO 1998/46645 A2 | 10/1998 |
| WO | WO 1998/50433 A2 | 11/1998 |
| WO | WO 1999/55306 A1 | 11/1999 |
| WO | WO 2002/060951 A2 | 8/2002 |
| WO | WO 2002/103024 A2 | 12/2002 |
| WO | WO 2003/031464 A2 | 4/2003 |
| WO | WO 2003/087355 A1 | 10/2003 |
| WO | WO 2003/093313 A2 | 11/2003 |
| WO | WO 2004/067566 A1 | 8/2004 |
| WO | WO 2004/075923 A2 | 9/2004 |
| WO | WO 2004/101740 A2 | 11/2004 |
| WO | WO 2005/117984 A2 | 12/2005 |
| WO | WO 2005/123780 A2 | 12/2005 |
| WO | WO 2006/053299 A2 | 5/2006 |
| WO | WO 2006/071801 A2 | 7/2006 |
| WO | WO 2006/108590 A1 | 10/2006 |
| WO | WO 2007/126808 A1 | 11/2007 |
| WO | WO 2008/082669 A2 | 7/2008 |
| WO | WO 2008077616 A1 | 7/2008 |
| WO | WO 2008/135501 A1 | 11/2008 |
| WO | WO 2008/151817 | 12/2008 |
| WO | WO 2009/007451 A1 | 1/2009 |
| WO | WO 2009/062100 A1 | 5/2009 |
| WO | WO 2009/108806 A1 | 9/2009 |
| WO | WO 2009/156137 A1 | 12/2009 |
| WO | WO 2010/014708 A2 | 2/2010 |
| WO | WO 2010/045568 A1 | 4/2010 |
| WO | WO 2010/102886 A1 | 9/2010 |
| WO | WO 2010/115866 A1 | 10/2010 |
| WO | WO 2011/101242 A1 | 8/2011 |
| WO | WO 2011/101267 A1 | 8/2011 |
| WO | WO 2011/101277 A1 | 8/2011 |
| WO | WO 2011/101284 A1 | 8/2011 |
| WO | WO 2011/131510 A2 | 10/2011 |
| WO | WO 2012/007324 A2 | 1/2012 |
| WO | WO 2013/083858 A1 | 6/2013 |
| WO | WO 2013/167303 A1 | 11/2013 |

OTHER PUBLICATIONS

Thorpe, P. E., et al., "The Preparation and Cytotoxic Properties of Antibody-Toxin Conjugates," Immunological Rev., vol. 62, pp. 119-158 (1982).
Lee, L. M., et al., "An Effect of Predilution on Potency Assays of Factor VIII Concentrates," Thrombosis Research, vol. 30, pp. 511-519 (1983).
Wahl, R. L., et al., "Investigative Nuclear Medicine," The Journal of Nuclear Medicine, vol. 24, pp. 316-325 (1983).
Morrison, S. L., "Transfectomas Provide Novel Chimeric Antibodies," Science, vol. 229, pp. 1202-1207.
Oi, V. T., et al., "Chimeric Antibodies," BioTechniques, vol. 4(3), pp. 214-221 (1986).
Collins, C. J., et al., "Molecular cloning of the human gene4 for von Willebrand factor and identification of the transcription initiation site," Proc. Natl. Acad. Sci., vol. 84, pp. 4393-4397 (1987).
Hellström, K. E., et al., "Controlled Drug Delivery Fundamentals and Applications," $2^{nd}$ Ed., Marcel Dekker, Inc., pp. 623-653 (1987).
Riechmann, L., et al., "Reshaping human antibodies for therapy," Nature, vol. 332, pp. 323-327 (1984).
Gillies, S. D., et al., "High-level expression of chimeric antibodies using adapted cDNA variable region cassettes," Journal of Immunological Methods, vol. 125, pp. 191-202 (1989).
Canfield, S. M., et al., "The Binding Affinity of Human IgG for its High Affinity Fc Receptor is Determined by Multiple Amino Acids in the $C^H2$ Domain and is Modulated by the Hinge Region," J. Exp. Med., vol. 173, pp. 1483-1491 (1991).
Lund, J., et al., "Human Fc gamma RI and Fc gamma RII interact with distinct but overlapping sites on human IgG," J. Immunol, vol. 147(8), pp. 2657-2662 (1991).
Padlan, E. A., "A Possible Procedure for Reducing the Immunogenicity of Antibody Variable Domains While Preserving Their Ligand-Binding Properties," Molecular Immunology, vol. 28(4/5), pp. 489-498 (1991).
Fischer, B., et al., "Structural analysis of recombinant von Willebrand factor: identification of hetero- and homo-dimers," FEBS Letters vol. 351, pp. 345-348 (1994).
Jespers, L. S., et al., "Guiding the Selection of Human Antibodies from Phage Display Repertoires to a Single Epitope of an Antigen," Nature Publishing Group, Bio0/Technology, vol. 12, pp. 899-903 (1994).
Roguska, M. A., "Humanization of murine monoclonal antibodies through variable domain resurfacing," Proc. Natl. Acad. Sci., vol. 91, pp. 969-973 (1994).
Studnicka, G. M., "Human-engineered monoclonal antibodies retain full specific binding activity by preserving non-CDR complementarity-modulating residues," Protein Engineering, vol. 7(6), pp. 805-814 (1994).
Suzuki, N., et al., "Molecular Cloning and Expression of cDNA Encoding Human Macrophage C-Type Lectin," The American Association of Immunologists, pp. 128-135 (1996).
Dubowchik, G. M., et al., "Receptor-mediated and enzyme-dependent targeting of cytotoxic anticancer drugs," Pharmacology & Therapeutics, vol. 83, pp. 67-123 (1999).
Bendetowicz, et al., "Binding of Factor VIII to von Willebrand Factor is Enabled by cleavage of the von Willebrand Factor Propeptide and Enhanced by Formation of Disulfide-Linked Multimers," Blood, 92(2): 529-538 (1998).
Kallas, A., et al., "The von Willebrand factor collagen-binding activity assay: clinical application," Ann Hematol, vol. 80, pp. 466-471 (2001).
Chapman, A. P., "PEGylated antibodies and antibody fragments for improved therapy: a review," Advanced Drug Delivery Reviews, vol. 54, pp. 531-545 (2002).
McCormick, C. L., et al., "Water-Soluble Polymers," Encylopedia of Plymer Science and Technology, Wood Composites, vol. 12, pp. 452-521 (2002).
Federici, A. B., "A sensitive ristocetin co-factor activity assay with recombinant glycoprotein Ibα for the diagnosis of patients with low von Willebrand factor levels," Haematologics, vol. 89(1), pp. 77-85 (2004).
Sucker, C., et al., "Determination of von Willebrand Factor Activity: Evaluation of the HaemosIL™ Assay in Comparison With Established Procedures," Clinical and Applied Thrombosis/Hemostasis, vol. 12(3), pp. 305-310 (2006).
Canis, K., et al., "The plasma von Willebrand factor O-glycome comprises a surprising variety of structures including ABH antigens and disialosyl motifs," Journal of Thrombosis and Hemostasis, vol. 8, pp. 137-145 (2010).
Veyradier, A., et al., "Validation of the first commercial ELISA for type 2N von Willebrand's disease diagnosis," Haemophilia, vol. 17, pp. 944-951 (2011).
Canis, K., et al., "Mapping the N-glycome of human von Willebrand factor," Biochem J., vol. 447, pp. 217-228 (2012).
Badirou, I., et al., "In vivo Analysis of the Role of O-Glycosylations of Von Willebrand Factor," PlosOne, vol. 7, Issue 5, May 2012 (11 pages).
Zhou, Y. F., et al., "Sequence and structure relationships within von Willebrand factor," Blood, vol. 120(2), pp. 449-458 (2012).
XP002742402 Database UniProt [Online], Nov. 26, 2014. Retrieved from EBI accession No. UNIPROT: A0A093H1R9 (2 pages).
XP002742403 UNIPROT [Online], Jul. 5, 2004. Rtrieved from EBI accession No. UNIPROT:Q76913 (2 pages).
International Search Report and the Written Opinion of the International Searching Authority, issued in International Application No. PCT/EP2016/054647, dated May 30, 2016, 15 pages.

(56) References Cited

OTHER PUBLICATIONS

European Search Report issued in EP Patent Application No. 15158065.1, dated Aug. 3, 2015, 8 pages.

* cited by examiner

SEQUENCE LISTING

```
<160> NUMBER OF SEQ ID NOS: 12

<210> SEQ ID NO 1
<211> LENGTH: 8442
<212> TYPE: DNA
<213> ORGANISM: Homo sapiens
<220> FEATURE:
<221> NAME/KEY: CDS
<222> LOCATION: (1)..(8442)

<400> SEQUENCE: 1
```

```
atg att cct gcc aga ttt gcc ggg gtg ctg ctt gct ctg gcc ctc att    48
Met Ile Pro Ala Arg Phe Ala Gly Val Leu Leu Ala Leu Ala Leu Ile
1               5                   10                  15 ttg cca ggg acc ctt tgt gca gaa gga act cgc ggc agg tca tcc acg    96
Leu Pro Gly Thr Leu Cys Ala Glu Gly Thr Arg Gly Arg Ser Ser Thr
            20                  25                  30 gcc cga tgc agc ctt ttc gga agt gac ttc gtc aac acc ttt gat ggg   144
Ala Arg Cys Ser Leu Phe Gly Ser Asp Phe Val Asn Thr Phe Asp Gly
        35                  40                  45 agc atg tac agc ttt gcg gga tac tgc agt tac ctc ctg gca ggg ggc   192
Ser Met Tyr Ser Phe Ala Gly Tyr Cys Ser Tyr Leu Leu Ala Gly Gly
    50                  55                  60 tgc cag aaa cgc tcc ttc tcg att att ggg gac ttc cag aat ggc aag   240
Cys Gln Lys Arg Ser Phe Ser Ile Ile Gly Asp Phe Gln Asn Gly Lys
65                  70                  75                  80 aga gtg agc ctc tcc gtg tat ctt ggg gaa ttt ttt gac atc cat ttg   288
Arg Val Ser Leu Ser Val Tyr Leu Gly Glu Phe Phe Asp Ile His Leu
                85                  90                  95 ttt gtc aat ggt acc gtg aca cag ggg gac caa aga gtc tcc atg ccc   336
Phe Val Asn Gly Thr Val Thr Gln Gly Asp Gln Arg Val Ser Met Pro
            100                 105                 110 tat gcc tcc aaa ggg ctg tat cta gaa act gag gct ggg tac tac aag   384
Tyr Ala Ser Lys Gly Leu Tyr Leu Glu Thr Glu Ala Gly Tyr Tyr Lys
        115                 120                 125 ctg tcc ggt gag gcc tat ggc ttt gtg gcc agg atc gat ggc agc ggc   432
Leu Ser Gly Glu Ala Tyr Gly Phe Val Ala Arg Ile Asp Gly Ser Gly
    130                 135                 140 aac ttt caa gtc ctg ctg tca gac aga tac ttc aac aag acc tgc ggg   480
Asn Phe Gln Val Leu Leu Ser Asp Arg Tyr Phe Asn Lys Thr Cys Gly
145                 150                 155                 160 ctg tgt ggc aac ttt aac atc ttt gct gaa gat gac ttt atg acc caa   528
Leu Cys Gly Asn Phe Asn Ile Phe Ala Glu Asp Asp Phe Met Thr Gln
                165                 170                 175 gaa ggg acc ttg acc tcg gac cct tat gac ttt gcc aac tca tgg gct   576
Glu Gly Thr Leu Thr Ser Asp Pro Tyr Asp Phe Ala Asn Ser Trp Ala
            180                 185                 190 ctg agc agt gga gaa cag tgg tgt gaa cgg gca tct cct ccc agc agc   624
Leu Ser Ser Gly Glu Gln Trp Cys Glu Arg Ala Ser Pro Pro Ser Ser
        195                 200                 205 tca tgc aac atc tcc tct ggg gaa atg cag aag ggc ctg tgg gag cag   672
Ser Cys Asn Ile Ser Ser Gly Glu Met Gln Lys Gly Leu Trp Glu Gln
    210                 215                 220 tgc cag ctt ctg aag agc acc tcg gtg ttt gcc cgc tgc cac cct ctg   720
Cys Gln Leu Leu Lys Ser Thr Ser Val Phe Ala Arg Cys His Pro Leu
225                 230                 235                 240 gtg gac ccc gag cct ttt gtg gcc ctg tgt gag aag act ttg tgt gag   768
Val Asp Pro Glu Pro Phe Val Ala Leu Cys Glu Lys Thr Leu Cys Glu
                245                 250                 255 tgt gct ggg ggg ctg gag tgc gcc tgc cct gcc ctc ctg gag tac gcc   816
Cys Ala Gly Gly Leu Glu Cys Ala Cys Pro Ala Leu Leu Glu Tyr Ala
            260                 265                 270 cgg acc tgt gcc cag gag gga atg gtg ctg tac ggc tgg acc gac cac   864
Arg Thr Cys Ala Gln Glu Gly Met Val Leu Tyr Gly Trp Thr Asp His
        275                 280                 285 agc gcg tgc agc cca gtg tgc cct gct ggt atg gag tat agg cag tgt   912
Ser Ala Cys Ser Pro Val Cys Pro Ala Gly Met Glu Tyr Arg Gln Cys
    290                 295                 300 gtg tcc cct tgc gcc agg acc tgc cag agc ctg cac atc aat gaa atg   960
Val Ser Pro Cys Ala Arg Thr Cys Gln Ser Leu His Ile Asn Glu Met
```

```
                     305                    310                       315                      320
  tgt cag gag cga tgc gtg gat ggc tgc agc tgc cct gag gga cag ctc         1008
  Cys Gln Glu Arg Cys Val Asp Gly Cys Ser Cys Pro Glu Gly Gln Leu
                      325                     330                    335 ctg gat gaa ggc ctc tgc gtg gag agc acc gag tgt ccc tgc gtg cat         1056
  Leu Asp Glu Gly Leu Cys Val Glu Ser Thr Glu Cys Pro Cys Val His
                  340                     345                    350 tcc gga aag cgc tac cct ccc ggc acc tcc ctc tct cga gac tgc aac         1104
  Ser Gly Lys Arg Tyr Pro Pro Gly Thr Ser Leu Ser Arg Asp Cys Asn
              355                     360                    365 acc tgc att tgc cga aac agc cag tgg atc tgc agc aat gaa gaa tgt         1152
  Thr Cys Ile Cys Arg Asn Ser Gln Trp Ile Cys Ser Asn Glu Glu Cys
          370                     375                    380 cca ggg gag tgc ctt gtc aca ggt caa tca cac ttc aag agc ttt gac         1200
  Pro Gly Glu Cys Leu Val Thr Gly Gln Ser His Phe Lys Ser Phe Asp
  385                     390                    395                    400 aac aga tac ttc acc ttc agt ggg atc tgc cag tac ctg ctg gcc cgg         1248
  Asn Arg Tyr Phe Thr Phe Ser Gly Ile Cys Gln Tyr Leu Leu Ala Arg
                      405                    410                    415 gat tgc cag gac cac tcc ttc tcc att gtc att gag act gtc cag tgt         1296
  Asp Cys Gln Asp His Ser Phe Ser Ile Val Ile Glu Thr Val Gln Cys
                  420                    425                    430 gct gat gac cgc gac gct gtg tgc acc cgc tcc gtc acc gtc cgg ctg         1344
  Ala Asp Asp Arg Asp Ala Val Cys Thr Arg Ser Val Thr Val Arg Leu
              435                    440                    445 cct ggc ctg cac aac agc ctt gtg aaa ctg aag cat ggg gca gga gtt         1392
  Pro Gly Leu His Asn Ser Leu Val Lys Leu Lys His Gly Ala Gly Val
          450                    455                    460 gcc atg gat ggc cag gac gtc cag ctc ccc ctc ctg aaa ggt gac ctc         1440
  Ala Met Asp Gly Gln Asp Val Gln Leu Pro Leu Leu Lys Gly Asp Leu
  465                    470                    475                    480 cgc atc cag cat aca gtg acg gcc tcc gtg cgc ctc agc tac ggg gag         1488
  Arg Ile Gln His Thr Val Thr Ala Ser Val Arg Leu Ser Tyr Gly Glu
                      485                    490                    495 gac ctg cag atg gac tgg gat ggc cgc ggg agg ctg ctg gtg aag ctg         1536
  Asp Leu Gln Met Asp Trp Asp Gly Arg Gly Arg Leu Leu Val Lys Leu
                  500                    505                    510 tcc ccc gtc tat gcc ggg aag acc tgc ggc ctg tgt ggg aat tac aat         1584
  Ser Pro Val Tyr Ala Gly Lys Thr Cys Gly Leu Cys Gly Asn Tyr Asn
              515                    520                    525 ggc aac cag ggc gac gac ttc ctt acc ccc tct ggg ctg gcg gag ccc         1632
  Gly Asn Gln Gly Asp Asp Phe Leu Thr Pro Ser Gly Leu Ala Glu Pro
          530                    535                    540 cgg gtg gag gac ttc ggg aac gcc tgg aag ctg cac ggg gac tgc cag         1680
  Arg Val Glu Asp Phe Gly Asn Ala Trp Lys Leu His Gly Asp Cys Gln
  545                    550                    555                    560 gac ctg cag aag cag cac agc gat ccc tgc gcc ctc aac ccg cgc atg         1728
  Asp Leu Gln Lys Gln His Ser Asp Pro Cys Ala Leu Asn Pro Arg Met
                      565                    570                    575 acc agg ttc tcc gag gag gcg tgc gcg gtc ctg acg tcc ccc aca ttc         1776
  Thr Arg Phe Ser Glu Glu Ala Cys Ala Val Leu Thr Ser Pro Thr Phe
                  580                    585                    590 gag gcc tgc cat cgt gcc gtc agc ccg ctg ccc tac ctg cgg aac tgc         1824
  Glu Ala Cys His Arg Ala Val Ser Pro Leu Pro Tyr Leu Arg Asn Cys
              595                    600                    605 cgc tac gac gtg tgc tcc tgc tcg gac ggc cgc gag tgc ctg tgc ggc         1872
  Arg Tyr Asp Val Cys Ser Cys Ser Asp Gly Arg Glu Cys Leu Cys Gly
          610                    615                    620 gcc ctg gcc agc tat gcc gcg gcc tgc gcg ggg aga ggc gtg cgc gtc         1920
```

-continued

| | | |
|---|---|---|
| Ala Leu Ala Ser Tyr Ala Ala Cys Ala Gly Arg Gly Val Arg Val<br>625                             630                            635                         640 | | |
| gcg tgg cgc gag cca ggc cgc tgt gag ctg aac tgc ccg aaa ggc cag<br>Ala Trp Arg Glu Pro Gly Arg Cys Glu Leu Asn Cys Pro Lys Gly Gln<br>                      645                          650                         655 | 1968 |
| gtg tac ctg cag tgc ggg acc ccc tgc aac ctg acc tgc cgc tct ctc<br>Val Tyr Leu Gln Cys Gly Thr Pro Cys Asn Leu Thr Cys Arg Ser Leu<br>660                           665                           670 | 2016 |
| tct tac ccg gat gag gaa tgc aat gag gcc tgc ctg gag ggc tgc ttc<br>Ser Tyr Pro Asp Glu Glu Cys Asn Glu Ala Cys Leu Glu Gly Cys Phe<br>                      675                         680                         685 | 2064 |
| tgc ccc cca ggg ctc tac atg gat gag agg ggg gac tgc gtc ccc aag<br>Cys Pro Pro Gly Leu Tyr Met Asp Glu Arg Gly Asp Cys Val Pro Lys<br>690                           695                           700 | 2112 |
| gcc cag tgc ccc tgt tac tat gac ggt gag atc ttc cag cca gaa gac<br>Ala Gln Cys Pro Cys Tyr Tyr Asp Gly Glu Ile Phe Gln Pro Glu Asp<br>705                           710                         715                         720 | 2160 |
| atc ttc tca gac cat cac acc atg tgc tac tgt gag gat ggc ttc atg<br>Ile Phe Ser Asp His His Thr Met Cys Tyr Cys Glu Asp Gly Phe Met<br>                          725                           730                         735 | 2208 |
| cac tgt acc atg agt gga gtc ccc gga agc ttg ctg cct gac gct gtc<br>His Cys Thr Met Ser Gly Val Pro Gly Ser Leu Leu Pro Asp Ala Val<br>                    740                         745                         750 | 2256 |
| ctc agc agt ccc ctg tct cat cgc agc aaa agg agc cta tcc tgt cgg<br>Leu Ser Ser Pro Leu Ser His Arg Ser Lys Arg Ser Leu Ser Cys Arg<br>              755                         760                         765 | 2304 |
| ccc ccc atg gtc aag ctg gtg tgt ccc gct gac aac ctg cgg gct gaa<br>Pro Pro Met Val Lys Leu Val Cys Pro Ala Asp Asn Leu Arg Ala Glu<br>770                           775                         780 | 2352 |
| ggg ctc gag tgt acc aaa acg tgc cag aac tat gac ctg gag tgc atg<br>Gly Leu Glu Cys Thr Lys Thr Cys Gln Asn Tyr Asp Leu Glu Cys Met<br>785                           790                         795                         800 | 2400 |
| agc atg ggc tgt gtc tct ggc tgc ctc tgc ccc ccg ggc atg gtc cgg<br>Ser Met Gly Cys Val Ser Gly Cys Leu Cys Pro Pro Gly Met Val Arg<br>                         805                         810                         815 | 2448 |
| cat gag aac aga tgt gtg gcc ctg gaa agg tgt ccc tgc ttc cat cag<br>His Glu Asn Arg Cys Val Ala Leu Glu Arg Cys Pro Cys Phe His Gln<br>                  820                         825                         830 | 2496 |
| ggc aag gag tat gcc cct gga gaa aca gtg aag att ggc tgc aac act<br>Gly Lys Glu Tyr Ala Pro Gly Glu Thr Val Lys Ile Gly Cys Asn Thr<br>              835                         840                         845 | 2544 |
| tgt gtc tgt cgg gac cgg aag tgg aac tgc aca gac cat gtg tgt gat<br>Cys Val Cys Arg Asp Arg Lys Trp Asn Cys Thr Asp His Val Cys Asp<br>850                           855                         860 | 2592 |
| gcc acg tgc tcc acg atc ggc atg gcc cac tac ctc acc ttc gac ggg<br>Ala Thr Cys Ser Thr Ile Gly Met Ala His Tyr Leu Thr Phe Asp Gly<br>865                           870                         875                         880 | 2640 |
| ctc aaa tac ctg ttc ccc ggg gag tgc cag tac gtt ctg gtg cag gat<br>Leu Lys Tyr Leu Phe Pro Gly Glu Cys Gln Tyr Val Leu Val Gln Asp<br>                  885                         890                         895 | 2688 |
| tac tgc ggc agt aac cct ggg acc ttt cgg atc cta gtg ggg aat aag<br>Tyr Cys Gly Ser Asn Pro Gly Thr Phe Arg Ile Leu Val Gly Asn Lys<br>                900                         905                         910 | 2736 |
| gga tgc agc cac ccc tca gtg aaa tgc aag aaa cgg gtc acc atc ctg<br>Gly Cys Ser His Pro Ser Val Lys Cys Lys Lys Arg Val Thr Ile Leu<br>              915                         920                         925 | 2784 |
| gtg gag gga gga gag att gag ctg ttt gac ggg gag gtg aat gtg aag<br>Val Glu Gly Gly Glu Ile Glu Leu Phe Asp Gly Glu Val Asn Val Lys<br>930                           935                         940 | 2832 |

|   |   |   |   |   |   |   |   |   |   |   |   |   |   |   |      |
|---|---|---|---|---|---|---|---|---|---|---|---|---|---|---|------|
| agg | ccc | atg | aag | gat | gag | act | cac | ttt | gag | gtg | gtg | gag | tct | ggc | cgg | 2880 |
| Arg | Pro | Met | Lys | Asp | Glu | Thr | His | Phe | Glu | Val | Val | Glu | Ser | Gly | Arg |
| 945 | | | | | 950 | | | | 955 | | | | | 960 | |

| tac | atc | att | ctg | ctg | ctg | ggc | aaa | gcc | ctc | tcc | gtg | gtc | tgg | gac | cgc | 2928 |
|---|---|---|---|---|---|---|---|---|---|---|---|---|---|---|---|---|
| Tyr | Ile | Ile | Leu | Leu | Leu | Gly | Lys | Ala | Leu | Ser | Val | Val | Trp | Asp | Arg |
| | | | | 965 | | | | | 970 | | | | | 975 | |

| cac | ctg | agc | atc | tcc | gtg | gtc | ctg | aag | cag | aca | tac | cag | gag | aaa | gtg | 2976 |
|---|---|---|---|---|---|---|---|---|---|---|---|---|---|---|---|---|
| His | Leu | Ser | Ile | Ser | Val | Val | Leu | Lys | Gln | Thr | Tyr | Gln | Glu | Lys | Val |
| | | | 980 | | | | | 985 | | | | | 990 | | |

| tgt | ggc | ctg | tgt | ggg | aat | ttt | gat | ggc | atc | cag | aac | aat | gac | ctc | acc | 3024 |
|---|---|---|---|---|---|---|---|---|---|---|---|---|---|---|---|---|
| Cys | Gly | Leu | Cys | Gly | Asn | Phe | Asp | Gly | Ile | Gln | Asn | Asn | Asp | Leu | Thr |
| | | 995 | | | | | 1000 | | | | | 1005 | | | |

| agc | agc | aac | ctc | caa | gtg | gag | gaa | gac | cct | gtg | gac | ttt | ggg | aac | 3069 |
|---|---|---|---|---|---|---|---|---|---|---|---|---|---|---|---|
| Ser | Ser | Asn | Leu | Gln | Val | Glu | Glu | Asp | Pro | Val | Asp | Phe | Gly | Asn |
| | 1010 | | | | | 1015 | | | | | 1020 | | | | |

| tcc | tgg | aaa | gtg | agc | tcg | cag | tgt | gct | gac | acc | aga | aaa | gtg | cct | 3114 |
|---|---|---|---|---|---|---|---|---|---|---|---|---|---|---|---|
| Ser | Trp | Lys | Val | Ser | Ser | Gln | Cys | Ala | Asp | Thr | Arg | Lys | Val | Pro |
| | 1025 | | | | | 1030 | | | | | 1035 | | | | |

| ctg | gac | tca | tcc | cct | gcc | acc | tgc | cat | aac | aac | atc | atg | aag | cag | 3159 |
|---|---|---|---|---|---|---|---|---|---|---|---|---|---|---|---|
| Leu | Asp | Ser | Ser | Pro | Ala | Thr | Cys | His | Asn | Asn | Ile | Met | Lys | Gln |
| | 1040 | | | | | 1045 | | | | | 1050 | | | | |

| acg | atg | gtg | gat | tcc | tcc | tgt | aga | atc | ctt | acc | agt | gac | gtc | ttc | 3204 |
|---|---|---|---|---|---|---|---|---|---|---|---|---|---|---|---|
| Thr | Met | Val | Asp | Ser | Ser | Cys | Arg | Ile | Leu | Thr | Ser | Asp | Val | Phe |
| 1055 | | | | | 1060 | | | | | 1065 | | | | | |

| cag | gac | tgc | aac | aag | ctg | gtg | gac | ccc | gag | cca | tat | ctg | gat | gtc | 3249 |
|---|---|---|---|---|---|---|---|---|---|---|---|---|---|---|---|
| Gln | Asp | Cys | Asn | Lys | Leu | Val | Asp | Pro | Glu | Pro | Tyr | Leu | Asp | Val |
| 1070 | | | | | 1075 | | | | | 1080 | | | | | |

| tgc | att | tac | gac | acc | tgc | tcc | tgt | gag | tcc | att | ggg | gac | tgc | gcc | 3294 |
|---|---|---|---|---|---|---|---|---|---|---|---|---|---|---|---|
| Cys | Ile | Tyr | Asp | Thr | Cys | Ser | Cys | Glu | Ser | Ile | Gly | Asp | Cys | Ala |
| 1085 | | | | | 1090 | | | | | 1095 | | | | | |

| tgc | ttc | tgc | gac | acc | att | gct | gcc | tat | gcc | cac | gtg | tgt | gcc | cag | 3339 |
|---|---|---|---|---|---|---|---|---|---|---|---|---|---|---|---|
| Cys | Phe | Cys | Asp | Thr | Ile | Ala | Ala | Tyr | Ala | His | Val | Cys | Ala | Gln |
| 1100 | | | | | 1105 | | | | | 1110 | | | | | |

| cat | ggc | aag | gtg | gtg | acc | tgg | agg | acg | gcc | aca | ttg | tgc | ccc | cag | 3384 |
|---|---|---|---|---|---|---|---|---|---|---|---|---|---|---|---|
| His | Gly | Lys | Val | Val | Thr | Trp | Arg | Thr | Ala | Thr | Leu | Cys | Pro | Gln |
| 1115 | | | | | 1120 | | | | | 1125 | | | | | |

| agc | tgc | gag | gag | agg | aat | ctc | cgg | gag | aac | ggg | tat | gag | tgt | gag | 3429 |
|---|---|---|---|---|---|---|---|---|---|---|---|---|---|---|---|
| Ser | Cys | Glu | Glu | Arg | Asn | Leu | Arg | Glu | Asn | Gly | Tyr | Glu | Cys | Glu |
| 1130 | | | | | 1135 | | | | | 1140 | | | | | |

| tgg | cgc | tat | aac | agc | tgt | gca | cct | gcc | tgt | caa | gtc | acg | tgt | cag | 3474 |
|---|---|---|---|---|---|---|---|---|---|---|---|---|---|---|---|
| Trp | Arg | Tyr | Asn | Ser | Cys | Ala | Pro | Ala | Cys | Gln | Val | Thr | Cys | Gln |
| 1145 | | | | | 1150 | | | | | 1155 | | | | | |

| cac | cct | gag | cca | ctg | gcc | tgc | cct | gtg | cag | tgt | gtg | gag | ggc | tgc | 3519 |
|---|---|---|---|---|---|---|---|---|---|---|---|---|---|---|---|
| His | Pro | Glu | Pro | Leu | Ala | Cys | Pro | Val | Gln | Cys | Val | Glu | Gly | Cys |
| 1160 | | | | | 1165 | | | | | 1170 | | | | | |

| cat | gcc | cac | tgc | cct | cca | ggg | aaa | atc | ctg | gat | gag | ctt | ttg | cag | 3564 |
|---|---|---|---|---|---|---|---|---|---|---|---|---|---|---|---|
| His | Ala | His | Cys | Pro | Pro | Gly | Lys | Ile | Leu | Asp | Glu | Leu | Leu | Gln |
| 1175 | | | | | 1180 | | | | | 1185 | | | | | |

| acc | tgc | gtt | gac | cct | gaa | gac | tgt | cca | gtg | tgt | gag | gtg | gct | ggc | 3609 |
|---|---|---|---|---|---|---|---|---|---|---|---|---|---|---|---|
| Thr | Cys | Val | Asp | Pro | Glu | Asp | Cys | Pro | Val | Cys | Glu | Val | Ala | Gly |
| 1190 | | | | | 1195 | | | | | 1200 | | | | | |

| cgg | cgt | ttt | gcc | tca | gga | aag | aaa | gtc | acc | ttg | aat | ccc | agt | gac | 3654 |
|---|---|---|---|---|---|---|---|---|---|---|---|---|---|---|---|
| Arg | Arg | Phe | Ala | Ser | Gly | Lys | Lys | Val | Thr | Leu | Asn | Pro | Ser | Asp |
| 1205 | | | | | 1210 | | | | | 1215 | | | | | |

| cct | gag | cac | tgc | cag | att | tgc | cac | tgt | gat | gtt | gtc | aac | ctc | acc | 3699 |
|---|---|---|---|---|---|---|---|---|---|---|---|---|---|---|---|
| Pro | Glu | His | Cys | Gln | Ile | Cys | His | Cys | Asp | Val | Val | Asn | Leu | Thr |
| 1220 | | | | | 1225 | | | | | 1230 | | | | | |

| tgt | gaa | gcc | tgc | cag | gag | ccg | gga | ggc | ctg | gtg | gtg | cct | ccc | aca | 3744 |
|---|---|---|---|---|---|---|---|---|---|---|---|---|---|---|---|
| Cys | Glu | Ala | Cys | Gln | Glu | Pro | Gly | Gly | Leu | Val | Val | Pro | Pro | Thr |
| 1235 | | | | | 1240 | | | | | 1245 | | | | | |

```
gat gcc ccg gtg agc ccc acc act ctg tat gtg gag gac atc tcg      3789
Asp Ala Pro Val Ser Pro Thr Thr Leu Tyr Val Glu Asp Ile Ser
    1250             1255             1260 gaa ccg ccg ttg cac gat ttc tac tgc agc agg cta ctg gac ctg      3834
Glu Pro Pro Leu His Asp Phe Tyr Cys Ser Arg Leu Leu Asp Leu
    1265             1270             1275 gtc ttc ctg ctg gat ggc tcc tcc agg ctg tcc gag gct gag ttt      3879
Val Phe Leu Leu Asp Gly Ser Ser Arg Leu Ser Glu Ala Glu Phe
    1280             1285             1290 gaa gtg ctg aag gcc ttt gtg gtg gac atg atg gag cgg ctg cgc      3924
Glu Val Leu Lys Ala Phe Val Val Asp Met Met Glu Arg Leu Arg
    1295             1300             1305 atc tcc cag aag tgg gtc cgc gtg gcc gtg gtg gag tac cac gac      3969
Ile Ser Gln Lys Trp Val Arg Val Ala Val Val Glu Tyr His Asp
    1310             1315             1320 ggc tcc cac gcc tac atc ggg ctc aag gac cgg aag cga ccg tca      4014
Gly Ser His Ala Tyr Ile Gly Leu Lys Asp Arg Lys Arg Pro Ser
    1325             1330             1335 gag ctg cgg cgc att gcc agc cag gtg aag tat gcg ggc agc cag      4059
Glu Leu Arg Arg Ile Ala Ser Gln Val Lys Tyr Ala Gly Ser Gln
    1340             1345             1350 gtg gcc tcc acc agc gag gtc ttg aaa tac aca ctg ttc caa atc      4104
Val Ala Ser Thr Ser Glu Val Leu Lys Tyr Thr Leu Phe Gln Ile
    1355             1360             1365 ttc agc aag atc gac cgc cct gaa gcc tcc cgc atc gcc ctg ctc      4149
Phe Ser Lys Ile Asp Arg Pro Glu Ala Ser Arg Ile Ala Leu Leu
    1370             1375             1380 ctg atg gcc agc cag gag ccc caa cgg atg tcc cgg aac ttt gtc      4194
Leu Met Ala Ser Gln Glu Pro Gln Arg Met Ser Arg Asn Phe Val
    1385             1390             1395 cgc tac gtc cag ggc ctg aag aag aag aag gtc att gtg atc ccg      4239
Arg Tyr Val Gln Gly Leu Lys Lys Lys Lys Val Ile Val Ile Pro
    1400             1405             1410 gtg ggc att ggg ccc cat gcc aac ctc aag cag atc cgc ctc atc      4284
Val Gly Ile Gly Pro His Ala Asn Leu Lys Gln Ile Arg Leu Ile
    1415             1420             1425 gag aag cag gcc cct gag aac aag gcc ttc gtg ctg agc agt gtg      4329
Glu Lys Gln Ala Pro Glu Asn Lys Ala Phe Val Leu Ser Ser Val
    1430             1435             1440 gat gag ctg gag cag caa agg gac gag atc gtt agc tac ctc tgt      4374
Asp Glu Leu Glu Gln Gln Arg Asp Glu Ile Val Ser Tyr Leu Cys
    1445             1450             1455 gac ctt gcc cct gaa gcc cct cct cct act ctg ccc ccc cac atg      4419
Asp Leu Ala Pro Glu Ala Pro Pro Pro Thr Leu Pro Pro His Met
    1460             1465             1470 gca caa gtc act gtg ggc ccg ggg ctc ttg ggg gtt tcg acc ctg      4464
Ala Gln Val Thr Val Gly Pro Gly Leu Leu Gly Val Ser Thr Leu
    1475             1480             1485 ggg ccc aag agg aac tcc atg gtt ctg gat gtg gcg ttc gtc ctg      4509
Gly Pro Lys Arg Asn Ser Met Val Leu Asp Val Ala Phe Val Leu
    1490             1495             1500 gaa gga tcg gac aaa att ggt gaa gcc gac ttc aac agg agc aag      4554
Glu Gly Ser Asp Lys Ile Gly Glu Ala Asp Phe Asn Arg Ser Lys
    1505             1510             1515 gag ttc atg gag gag gtg att cag cgg atg gat gtg ggc cag gac      4599
Glu Phe Met Glu Glu Val Ile Gln Arg Met Asp Val Gly Gln Asp
    1520             1525             1530 agc atc cac gtc acg gtg ctg cag tac tcc tac atg gtg acc gtg      4644
Ser Ile His Val Thr Val Leu Gln Tyr Ser Tyr Met Val Thr Val
```

-continued

|  | 1535 |  |  |  | 1540 |  |  |  | 1545 |  |  |  |  |
|---|---|---|---|---|---|---|---|---|---|---|---|---|---|
| gag | tac | ccc | ttc | agc | gag | gca | cag | tcc | aaa | ggg | gac | atc | ctg | cag | 4689 |
| Glu | Tyr | Pro | Phe | Ser | Glu | Ala | Gln | Ser | Lys | Gly | Asp | Ile | Leu | Gln |  |
|  | 1550 |  |  |  | 1555 |  |  |  | 1560 |  |  |  |  |

| cgg | gtg | cga | gag | atc | cgc | tac | cag | ggc | ggc | aac | agg | acc | aac | act | 4734 |
| Arg | Val | Arg | Glu | Ile | Arg | Tyr | Gln | Gly | Gly | Asn | Arg | Thr | Asn | Thr |  |
| 1565 |  |  |  | 1570 |  |  |  | 1575 |  |  |  |  |

| ggg | ctg | gcc | ctg | cgg | tac | ctc | tct | gac | cac | agc | ttc | ttg | gtc | agc | 4779 |
| Gly | Leu | Ala | Leu | Arg | Tyr | Leu | Ser | Asp | His | Ser | Phe | Leu | Val | Ser |  |
| 1580 |  |  |  | 1585 |  |  |  | 1590 |  |  |  |  |

| cag | ggt | gac | cgg | gag | cag | gcg | ccc | aac | ctg | gtc | tac | atg | gtc | acc | 4824 |
| Gln | Gly | Asp | Arg | Glu | Gln | Ala | Pro | Asn | Leu | Val | Tyr | Met | Val | Thr |  |
| 1595 |  |  |  | 1600 |  |  |  | 1605 |  |  |  |  |

| gga | aat | cct | gcc | tct | gat | gag | atc | aag | agg | ctg | cct | gga | gac | atc | 4869 |
| Gly | Asn | Pro | Ala | Ser | Asp | Glu | Ile | Lys | Arg | Leu | Pro | Gly | Asp | Ile |  |
| 1610 |  |  |  | 1615 |  |  |  | 1620 |  |  |  |  |

| cag | gtg | gtg | ccc | att | gga | gtg | ggc | cct | aat | gcc | aac | gtg | cag | gag | 4914 |
| Gln | Val | Val | Pro | Ile | Gly | Val | Gly | Pro | Asn | Ala | Asn | Val | Gln | Glu |  |
| 1625 |  |  |  | 1630 |  |  |  | 1635 |  |  |  |  |

| ctg | gag | agg | att | ggc | tgg | ccc | aat | gcc | cct | atc | ctc | atc | cag | gac | 4959 |
| Leu | Glu | Arg | Ile | Gly | Trp | Pro | Asn | Ala | Pro | Ile | Leu | Ile | Gln | Asp |  |
| 1640 |  |  |  | 1645 |  |  |  | 1650 |  |  |  |  |

| ttt | gag | acg | ctc | ccc | cga | gag | gct | cct | gac | ctg | gtg | ctg | cag | agg | 5004 |
| Phe | Glu | Thr | Leu | Pro | Arg | Glu | Ala | Pro | Asp | Leu | Val | Leu | Gln | Arg |  |
| 1655 |  |  |  | 1660 |  |  |  | 1665 |  |  |  |  |

| tgc | tgc | tcc | gga | gag | ggg | ctg | cag | atc | ccc | acc | ctc | tcc | cct | gca | 5049 |
| Cys | Cys | Ser | Gly | Glu | Gly | Leu | Gln | Ile | Pro | Thr | Leu | Ser | Pro | Ala |  |
| 1670 |  |  |  | 1675 |  |  |  | 1680 |  |  |  |  |

| cct | gac | tgc | agc | cag | ccc | ctg | gac | gtg | atc | ctt | ctc | ctg | gat | ggc | 5094 |
| Pro | Asp | Cys | Ser | Gln | Pro | Leu | Asp | Val | Ile | Leu | Leu | Leu | Asp | Gly |  |
| 1685 |  |  |  | 1690 |  |  |  | 1695 |  |  |  |  |

| tcc | tcc | agt | ttc | cca | gct | tct | tat | ttt | gat | gaa | atg | aag | agt | ttc | 5139 |
| Ser | Ser | Ser | Phe | Pro | Ala | Ser | Tyr | Phe | Asp | Glu | Met | Lys | Ser | Phe |  |
| 1700 |  |  |  | 1705 |  |  |  | 1710 |  |  |  |  |

| gcc | aag | gct | ttc | att | tca | aaa | gcc | aat | ata | ggg | cct | cgt | ctc | act | 5184 |
| Ala | Lys | Ala | Phe | Ile | Ser | Lys | Ala | Asn | Ile | Gly | Pro | Arg | Leu | Thr |  |
| 1715 |  |  |  | 1720 |  |  |  | 1725 |  |  |  |  |

| cag | gtg | tca | gtg | ctg | cag | tat | gga | agc | atc | acc | acc | att | gac | gtg | 5229 |
| Gln | Val | Ser | Val | Leu | Gln | Tyr | Gly | Ser | Ile | Thr | Thr | Ile | Asp | Val |  |
| 1730 |  |  |  | 1735 |  |  |  | 1740 |  |  |  |  |

| cca | tgg | aac | gtg | gtc | ccg | gag | aaa | gcc | cat | ttg | ctg | agc | ctt | gtg | 5274 |
| Pro | Trp | Asn | Val | Val | Pro | Glu | Lys | Ala | His | Leu | Leu | Ser | Leu | Val |  |
| 1745 |  |  |  | 1750 |  |  |  | 1755 |  |  |  |  |

| gac | gtc | atg | cag | cgg | gag | gga | ggc | ccc | agc | caa | atc | ggg | gat | gcc | 5319 |
| Asp | Val | Met | Gln | Arg | Glu | Gly | Gly | Pro | Ser | Gln | Ile | Gly | Asp | Ala |  |
| 1760 |  |  |  | 1765 |  |  |  | 1770 |  |  |  |  |

| ttg | ggc | ttt | gct | gtg | cga | tac | ttg | act | tca | gaa | atg | cat | ggg | gcg | 5364 |
| Leu | Gly | Phe | Ala | Val | Arg | Tyr | Leu | Thr | Ser | Glu | Met | His | Gly | Ala |  |
| 1775 |  |  |  | 1780 |  |  |  | 1785 |  |  |  |  |

| cgc | ccg | gga | gcc | tca | aag | gcg | gtg | gtc | atc | ctg | gtc | acg | gac | gtc | 5409 |
| Arg | Pro | Gly | Ala | Ser | Lys | Ala | Val | Val | Ile | Leu | Val | Thr | Asp | Val |  |
| 1790 |  |  |  | 1795 |  |  |  | 1800 |  |  |  |  |

| tct | gtg | gat | tca | gtg | gat | gca | gca | gct | gat | gcc | gcc | agg | tcc | aac | 5454 |
| Ser | Val | Asp | Ser | Val | Asp | Ala | Ala | Ala | Asp | Ala | Ala | Arg | Ser | Asn |  |
| 1805 |  |  |  | 1810 |  |  |  | 1815 |  |  |  |  |

| aga | gtg | aca | gtg | ttc | cct | att | gga | att | gga | gat | cgc | tac | gat | gca | 5499 |
| Arg | Val | Thr | Val | Phe | Pro | Ile | Gly | Ile | Gly | Asp | Arg | Tyr | Asp | Ala |  |
| 1820 |  |  |  | 1825 |  |  |  | 1830 |  |  |  |  |

| gcc | cag | cta | cgg | atc | ttg | gca | ggc | cca | gca | ggc | gac | tcc | aac | gtg | 5544 |

```
                Ala Gln Leu Arg Ile Leu Ala Gly Pro Ala Gly Asp Ser Asn Val
                    1835                1840                1845 gtg aag ctc cag cga atc gaa gac ctc cct acc atg gtc acc ttg           5589
Val Lys Leu Gln Arg Ile Glu Asp Leu Pro Thr Met Val Thr Leu
1850                1855                1860 ggc aat tcc ttc ctc cac aaa ctg tgc tct gga ttt gtt agg att           5634
Gly Asn Ser Phe Leu His Lys Leu Cys Ser Gly Phe Val Arg Ile
1865                1870                1875 tgc atg gat gag gat ggg aat gag aag agg ccc ggg gac gtc tgg           5679
Cys Met Asp Glu Asp Gly Asn Glu Lys Arg Pro Gly Asp Val Trp
1880                1885                1890 acc ttg cca gac cag tgc cac acc gtg act tgc cag cca gat ggc           5724
Thr Leu Pro Asp Gln Cys His Thr Val Thr Cys Gln Pro Asp Gly
1895                1900                1905 cag acc ttg ctg aag agt cat cgg gtc aac tgt gac cgg ggg ctg           5769
Gln Thr Leu Leu Lys Ser His Arg Val Asn Cys Asp Arg Gly Leu
1910                1915                1920 agg cct tcg tgc cct aac agc cag tcc cct gtt aaa gtg gaa gag           5814
Arg Pro Ser Cys Pro Asn Ser Gln Ser Pro Val Lys Val Glu Glu
1925                1930                1935 acc tgt ggc tgc cgc tgg acc tgc ccc tgc gtg tgc aca ggc agc           5859
Thr Cys Gly Cys Arg Trp Thr Cys Pro Cys Val Cys Thr Gly Ser
1940                1945                1950 tcc act cgg cac atc gtg acc ttt gat ggg cag aat ttc aag ctg           5904
Ser Thr Arg His Ile Val Thr Phe Asp Gly Gln Asn Phe Lys Leu
1955                1960                1965 act ggc agc tgt tct tat gtc cta ttt caa aac aag gag cag gac           5949
Thr Gly Ser Cys Ser Tyr Val Leu Phe Gln Asn Lys Glu Gln Asp
1970                1975                1980 ctg gag gtg att ctc cat aat ggt gcc tgc agc cct gga gca agg           5994
Leu Glu Val Ile Leu His Asn Gly Ala Cys Ser Pro Gly Ala Arg
1985                1990                1995 cag ggc tgc atg aaa tcc atc gag gtg aag cac agt gcc ctc tcc           6039
Gln Gly Cys Met Lys Ser Ile Glu Val Lys His Ser Ala Leu Ser
2000                2005                2010 gtc gag ctg cac agt gac atg gag gtg acg gtg aat ggg aga ctg           6084
Val Glu Leu His Ser Asp Met Glu Val Thr Val Asn Gly Arg Leu
2015                2020                2025 gtc tct gtt cct tac gtg ggt ggg aac atg gaa gtc aac gtt tat           6129
Val Ser Val Pro Tyr Val Gly Gly Asn Met Glu Val Asn Val Tyr
2030                2035                2040 ggt gcc atc atg cat gag gtc aga ttc aat cac ctt ggt cac atc           6174
Gly Ala Ile Met His Glu Val Arg Phe Asn His Leu Gly His Ile
2045                2050                2055 ttc aca ttc act cca caa aac aat gag ttc caa ctg cag ctc agc           6219
Phe Thr Phe Thr Pro Gln Asn Asn Glu Phe Gln Leu Gln Leu Ser
2060                2065                2070 ccc aag act ttt gct tca aag acg tat ggt ctg tgt ggg atc tgt           6264
Pro Lys Thr Phe Ala Ser Lys Thr Tyr Gly Leu Cys Gly Ile Cys
2075                2080                2085 gat gag aac gga gcc aat gac ttc atg ctg agg gat ggc aca gtc           6309
Asp Glu Asn Gly Ala Asn Asp Phe Met Leu Arg Asp Gly Thr Val
2090                2095                2100 acc aca gac tgg aaa aca ctt gtt cag gaa tgg act gtg cag cgg           6354
Thr Thr Asp Trp Lys Thr Leu Val Gln Glu Trp Thr Val Gln Arg
2105                2110                2115 cca ggg cag acg tgc cag ccc atc ctg gag gag cag tgt ctt gtc           6399
Pro Gly Gln Thr Cys Gln Pro Ile Leu Glu Glu Gln Cys Leu Val
2120                2125                2130
```

| | | | | | | | | | | |
|---|---|---|---|---|---|---|---|---|---|---|
| ccc | gac | agc | tcc | cac | tgc | cag | gtc | ctc | ctc | tta | cca | ctg | ttt | gct | 6444 |
| Pro | Asp | Ser | Ser | His | Cys | Gln | Val | Leu | Leu | Leu | Pro | Leu | Phe | Ala | |
| 2135 | | | | 2140 | | | | | 2145 | | | | | | |

| gaa | tgc | cac | aag | gtc | ctg | gct | cca | gcc | aca | ttc | tat | gcc | atc | tgc | 6489 |
|---|---|---|---|---|---|---|---|---|---|---|---|---|---|---|---|
| Glu | Cys | His | Lys | Val | Leu | Ala | Pro | Ala | Thr | Phe | Tyr | Ala | Ile | Cys | |
| 2150 | | | | | 2155 | | | | | 2160 | | | | | |

| cag | cag | gac | agt | tgc | cac | cag | gag | caa | gtg | tgt | gag | gtg | atc | gcc | 6534 |
|---|---|---|---|---|---|---|---|---|---|---|---|---|---|---|---|
| Gln | Gln | Asp | Ser | Cys | His | Gln | Glu | Gln | Val | Cys | Glu | Val | Ile | Ala | |
| 2165 | | | | | 2170 | | | | | | 2175 | | | | |

| tct | tat | gcc | cac | ctc | tgt | cgg | acc | aac | ggg | gtc | tgc | gtt | gac | tgg | 6579 |
|---|---|---|---|---|---|---|---|---|---|---|---|---|---|---|---|
| Ser | Tyr | Ala | His | Leu | Cys | Arg | Thr | Asn | Gly | Val | Cys | Val | Asp | Trp | |
| 2180 | | | | 2185 | | | | | | 2190 | | | | | |

| agg | aca | cct | gat | ttc | tgt | gct | atg | tca | tgc | cca | cca | tct | ctg | gtt | 6624 |
|---|---|---|---|---|---|---|---|---|---|---|---|---|---|---|---|
| Arg | Thr | Pro | Asp | Phe | Cys | Ala | Met | Ser | Cys | Pro | Pro | Ser | Leu | Val | |
| 2195 | | | | | 2200 | | | | | 2205 | | | | | |

| tat | aac | cac | tgt | gag | cat | ggc | tgt | ccc | cgg | cac | tgt | gat | ggc | aac | 6669 |
|---|---|---|---|---|---|---|---|---|---|---|---|---|---|---|---|
| Tyr | Asn | His | Cys | Glu | His | Gly | Cys | Pro | Arg | His | Cys | Asp | Gly | Asn | |
| 2210 | | | | 2215 | | | | | | 2220 | | | | | |

| gtg | agc | tcc | tgt | ggg | gac | cat | ccc | tcc | gaa | ggc | tgt | ttc | tgc | cct | 6714 |
|---|---|---|---|---|---|---|---|---|---|---|---|---|---|---|---|
| Val | Ser | Ser | Cys | Gly | Asp | His | Pro | Ser | Glu | Gly | Cys | Phe | Cys | Pro | |
| 2225 | | | | | 2230 | | | | | 2235 | | | | | |

| cca | gat | aaa | gtc | atg | ttg | gaa | ggc | agc | tgt | gtc | cct | gaa | gag | gcc | 6759 |
|---|---|---|---|---|---|---|---|---|---|---|---|---|---|---|---|
| Pro | Asp | Lys | Val | Met | Leu | Glu | Gly | Ser | Cys | Val | Pro | Glu | Glu | Ala | |
| 2240 | | | | | 2245 | | | | | 2250 | | | | | |

| tgc | act | cag | tgc | att | ggt | gag | gat | gga | gtc | cag | cac | cag | ttc | ctg | 6804 |
|---|---|---|---|---|---|---|---|---|---|---|---|---|---|---|---|
| Cys | Thr | Gln | Cys | Ile | Gly | Glu | Asp | Gly | Val | Gln | His | Gln | Phe | Leu | |
| 2255 | | | | | 2260 | | | | | 2265 | | | | | |

| gaa | gcc | tgg | gtc | ccg | gac | cac | cag | ccc | tgt | cag | atc | tgc | aca | tgc | 6849 |
|---|---|---|---|---|---|---|---|---|---|---|---|---|---|---|---|
| Glu | Ala | Trp | Val | Pro | Asp | His | Gln | Pro | Cys | Gln | Ile | Cys | Thr | Cys | |
| 2270 | | | | | 2275 | | | | | 2280 | | | | | |

| ctc | agc | ggg | cgg | aag | gtc | aac | tgc | aca | acg | cag | ccc | tgc | ccc | acg | 6894 |
|---|---|---|---|---|---|---|---|---|---|---|---|---|---|---|---|
| Leu | Ser | Gly | Arg | Lys | Val | Asn | Cys | Thr | Thr | Gln | Pro | Cys | Pro | Thr | |
| 2285 | | | | | 2290 | | | | | 2295 | | | | | |

| gcc | aaa | gct | ccc | acg | tgt | ggc | ctg | tgt | gaa | gta | gcc | cgc | ctc | cgc | 6939 |
|---|---|---|---|---|---|---|---|---|---|---|---|---|---|---|---|
| Ala | Lys | Ala | Pro | Thr | Cys | Gly | Leu | Cys | Glu | Val | Ala | Arg | Leu | Arg | |
| 2300 | | | | | 2305 | | | | | 2310 | | | | | |

| cag | aat | gca | gac | cag | tgc | tgc | ccc | gag | tat | gag | tgt | gtg | tgt | gac | 6984 |
|---|---|---|---|---|---|---|---|---|---|---|---|---|---|---|---|
| Gln | Asn | Ala | Asp | Gln | Cys | Cys | Pro | Glu | Tyr | Glu | Cys | Val | Cys | Asp | |
| 2315 | | | | | 2320 | | | | | 2325 | | | | | |

| cca | gtg | agc | tgt | gac | ctg | ccc | cca | gtg | cct | cac | tgt | gaa | cgt | ggc | 7029 |
|---|---|---|---|---|---|---|---|---|---|---|---|---|---|---|---|
| Pro | Val | Ser | Cys | Asp | Leu | Pro | Pro | Val | Pro | His | Cys | Glu | Arg | Gly | |
| 2330 | | | | | 2335 | | | | | 2340 | | | | | |

| ctc | cag | ccc | aca | ctg | acc | aac | cct | ggc | gag | tgc | aga | ccc | aac | ttc | 7074 |
|---|---|---|---|---|---|---|---|---|---|---|---|---|---|---|---|
| Leu | Gln | Pro | Thr | Leu | Thr | Asn | Pro | Gly | Glu | Cys | Arg | Pro | Asn | Phe | |
| 2345 | | | | | 2350 | | | | | 2355 | | | | | |

| acc | tgc | gcc | tgc | agg | aag | gag | gag | tgc | aaa | aga | gtg | tcc | cca | ccc | 7119 |
|---|---|---|---|---|---|---|---|---|---|---|---|---|---|---|---|
| Thr | Cys | Ala | Cys | Arg | Lys | Glu | Glu | Cys | Lys | Arg | Val | Ser | Pro | Pro | |
| 2360 | | | | | 2365 | | | | | 2370 | | | | | |

| tcc | tgc | ccc | ccg | cac | cgt | ttg | ccc | acc | ctt | cgg | aag | acc | cag | tgc | 7164 |
|---|---|---|---|---|---|---|---|---|---|---|---|---|---|---|---|
| Ser | Cys | Pro | Pro | His | Arg | Leu | Pro | Thr | Leu | Arg | Lys | Thr | Gln | Cys | |
| 2375 | | | | | 2380 | | | | | 2385 | | | | | |

| tgt | gat | gag | tat | gag | tgt | gcc | tgc | aac | tgt | gtc | aac | tcc | aca | gtg | 7209 |
|---|---|---|---|---|---|---|---|---|---|---|---|---|---|---|---|
| Cys | Asp | Glu | Tyr | Glu | Cys | Ala | Cys | Asn | Cys | Val | Asn | Ser | Thr | Val | |
| 2390 | | | | | 2395 | | | | | 2400 | | | | | |

| agc | tgt | ccc | ctt | ggg | tac | ttg | gcc | tca | acc | gcc | acc | aat | gac | tgt | 7254 |
|---|---|---|---|---|---|---|---|---|---|---|---|---|---|---|---|
| Ser | Cys | Pro | Leu | Gly | Tyr | Leu | Ala | Ser | Thr | Ala | Thr | Asn | Asp | Cys | |
| 2405 | | | | | 2410 | | | | | 2415 | | | | | |

| ggc | tgt | acc | aca | acc | acc | tgc | ctt | ccc | gac | aag | gtg | tgt | gtc | cac | 7299 |
|---|---|---|---|---|---|---|---|---|---|---|---|---|---|---|---|
| Gly | Cys | Thr | Thr | Thr | Thr | Cys | Leu | Pro | Asp | Lys | Val | Cys | Val | His | |
| 2420 | | | | | 2425 | | | | | 2430 | | | | | |

```
cga agc acc atc tac cct gtg ggc cag ttc tgg gag gag ggc tgc      7344
Arg Ser Thr Ile Tyr Pro Val Gly Gln Phe Trp Glu Glu Gly Cys
    2435            2440                2445 gat gtg tgc acc tgc acc gac atg gag gat gcc gtg atg ggc ctc      7389
Asp Val Cys Thr Cys Thr Asp Met Glu Asp Ala Val Met Gly Leu
    2450            2455                2460 cgc gtg gcc cag tgc tcc cag aag ccc tgt gag gac agc tgt cgg      7434
Arg Val Ala Gln Cys Ser Gln Lys Pro Cys Glu Asp Ser Cys Arg
    2465            2470                2475 tcg ggc ttc act tac gtt ctg cat gaa ggc gag tgc tgt gga agg      7479
Ser Gly Phe Thr Tyr Val Leu His Glu Gly Glu Cys Cys Gly Arg
    2480            2485                2490 tgc ctg cca tct gcc tgt gag gtg gtg act ggc tca ccg cgg ggg      7524
Cys Leu Pro Ser Ala Cys Glu Val Val Thr Gly Ser Pro Arg Gly
    2495            2500                2505 gac tcc cag tct tcc tgg aag agt gtc ggc tcc cag tgg gcc tcc      7569
Asp Ser Gln Ser Ser Trp Lys Ser Val Gly Ser Gln Trp Ala Ser
    2510            2515                2520 ccg gag aac ccc tgc ctc atc aat gag tgt gtc cga gtg aag gag      7614
Pro Glu Asn Pro Cys Leu Ile Asn Glu Cys Val Arg Val Lys Glu
    2525            2530                2535 gag gtc ttt ata caa caa agg aac gtc tcc tgc ccc cag ctg gag      7659
Glu Val Phe Ile Gln Gln Arg Asn Val Ser Cys Pro Gln Leu Glu
    2540            2545                2550 gtc cct gtc tgc ccc tcg ggc ttt cag ctg agc tgt aag acc tca      7704
Val Pro Val Cys Pro Ser Gly Phe Gln Leu Ser Cys Lys Thr Ser
    2555            2560                2565 gcg tgc tgc cca agc tgt cgc tgt gag cgc atg gag gcc tgc atg      7749
Ala Cys Cys Pro Ser Cys Arg Cys Glu Arg Met Glu Ala Cys Met
    2570            2575                2580 ctc aat ggc act gtc att ggg ccc ggg aag act gtg atg atc gat      7794
Leu Asn Gly Thr Val Ile Gly Pro Gly Lys Thr Val Met Ile Asp
    2585            2590                2595 gtg tgc acg acc tgc cgc tgc atg gtg cag gtg ggg gtc atc tct      7839
Val Cys Thr Thr Cys Arg Cys Met Val Gln Val Gly Val Ile Ser
    2600            2605                2610 gga ttc aag ctg gag tgc agg aag acc acc tgc aac ccc tgc ccc      7884
Gly Phe Lys Leu Glu Cys Arg Lys Thr Thr Cys Asn Pro Cys Pro
    2615            2620                2625 ctg ggt tac aag gaa gaa aat aac aca ggt gaa tgt tgt ggg aga      7929
Leu Gly Tyr Lys Glu Glu Asn Asn Thr Gly Glu Cys Cys Gly Arg
    2630            2635                2640 tgt ttg cct acg gct tgc acc att cag cta aga gga gga cag atc      7974
Cys Leu Pro Thr Ala Cys Thr Ile Gln Leu Arg Gly Gly Gln Ile
    2645            2650                2655 atg aca ctg aag cgt gat gag acg ctc cag gat ggc tgt gat act      8019
Met Thr Leu Lys Arg Asp Glu Thr Leu Gln Asp Gly Cys Asp Thr
    2660            2665                2670 cac ttc tgc aag gtc aat gag aga gga gag tac ttc tgg gag aag      8064
His Phe Cys Lys Val Asn Glu Arg Gly Glu Tyr Phe Trp Glu Lys
    2675            2680                2685 agg gtc aca ggc tgc cca ccc ttt gat gaa cac aag tgt ctg gct      8109
Arg Val Thr Gly Cys Pro Pro Phe Asp Glu His Lys Cys Leu Ala
    2690            2695                2700 gag gga ggt aaa att atg aaa att cca ggc acc tgc tgt gac aca      8154
Glu Gly Gly Lys Ile Met Lys Ile Pro Gly Thr Cys Cys Asp Thr
    2705            2710                2715 tgt gag gag cct gag tgc aac gac atc act gcc agg ctg cag tat      8199
Cys Glu Glu Pro Glu Cys Asn Asp Ile Thr Ala Arg Leu Gln Tyr
```

```
                2720                2725                2730
gtc aag gtg gga agc tgt aag tct gaa gta gag gtg gat atc cac        8244
Val Lys Val Gly Ser Cys Lys Ser Glu Val Glu Val Asp Ile His
    2735                2740                2745 tac tgc cag ggc aaa tgt gcc agc aaa gcc atg tac tcc att gac        8289
Tyr Cys Gln Gly Lys Cys Ala Ser Lys Ala Met Tyr Ser Ile Asp
        2750                2755                2760 atc aac gat gtg cag gac cag tgc tcc tgc tct ccg aca cgg            8334
Ile Asn Asp Val Gln Asp Gln Cys Ser Cys Ser Pro Thr Arg
    2765                2770                2775 acg gag ccc atg cag gtg gcc ctg cac tgc acc aat ggc tct gtt        8379
Thr Glu Pro Met Gln Val Ala Leu His Cys Thr Asn Gly Ser Val
    2780                2785                2790 gtg tac cat gag gtt ctc aat gcc atg gag tgc aaa tgc tcc ccc        8424
Val Tyr His Glu Val Leu Asn Ala Met Glu Cys Lys Cys Ser Pro
    2795                2800                2805 agg aag tgc agc aag tga                                            8442
Arg Lys Cys Ser Lys
    2810

<210> SEQ ID NO 2
<211> LENGTH: 2813
<212> TYPE: PRT
<213> ORGANISM: Homo sapiens

<400> SEQUENCE: 2

Met Ile Pro Ala Arg Phe Ala Gly Val Leu Leu Ala Leu Ala Leu Ile
1               5                   10                  15

Leu Pro Gly Thr Leu Cys Ala Glu Gly Thr Arg Gly Arg Ser Ser Thr
            20                  25                  30

Ala Arg Cys Ser Leu Phe Gly Ser Asp Phe Val Asn Thr Phe Asp Gly
        35                  40                  45

Ser Met Tyr Ser Phe Ala Gly Tyr Cys Ser Tyr Leu Leu Ala Gly Gly
    50                  55                  60

Cys Gln Lys Arg Ser Phe Ser Ile Ile Gly Asp Phe Gln Asn Gly Lys
65                  70                  75                  80

Arg Val Ser Leu Ser Val Tyr Leu Gly Glu Phe Phe Asp Ile His Leu
                85                  90                  95

Phe Val Asn Gly Thr Val Thr Gln Gly Asp Gln Arg Val Ser Met Pro
            100                 105                 110

Tyr Ala Ser Lys Gly Leu Tyr Leu Glu Thr Glu Ala Gly Tyr Tyr Lys
        115                 120                 125

Leu Ser Gly Glu Ala Tyr Gly Phe Val Ala Arg Ile Asp Gly Ser Gly
    130                 135                 140

Asn Phe Gln Val Leu Leu Ser Asp Arg Tyr Phe Asn Lys Thr Cys Gly
145                 150                 155                 160

Leu Cys Gly Asn Phe Asn Ile Phe Ala Glu Asp Asp Phe Met Thr Gln
                165                 170                 175

Glu Gly Thr Leu Thr Ser Asp Pro Tyr Asp Phe Ala Asn Ser Trp Ala
            180                 185                 190

Leu Ser Ser Gly Glu Gln Trp Cys Glu Arg Ala Ser Pro Pro Ser Ser
        195                 200                 205

Ser Cys Asn Ile Ser Ser Gly Glu Met Gln Lys Gly Leu Trp Glu Gln
    210                 215                 220

Cys Gln Leu Leu Lys Ser Thr Ser Val Phe Ala Arg Cys His Pro Leu
225                 230                 235                 240
```

-continued

Val Asp Pro Glu Pro Phe Val Ala Leu Cys Glu Lys Thr Leu Cys Glu
            245                 250                 255

Cys Ala Gly Gly Leu Glu Cys Ala Cys Pro Ala Leu Leu Glu Tyr Ala
        260                 265                 270

Arg Thr Cys Ala Gln Glu Gly Met Val Leu Tyr Gly Trp Thr Asp His
    275                 280                 285

Ser Ala Cys Ser Pro Val Cys Pro Ala Gly Met Glu Tyr Arg Gln Cys
290                 295                 300

Val Ser Pro Cys Ala Arg Thr Cys Gln Ser Leu His Ile Asn Glu Met
305                 310                 315                 320

Cys Gln Glu Arg Cys Val Asp Gly Cys Ser Cys Pro Glu Gly Gln Leu
            325                 330                 335

Leu Asp Glu Gly Leu Cys Val Glu Ser Thr Glu Cys Pro Cys Val His
        340                 345                 350

Ser Gly Lys Arg Tyr Pro Pro Gly Thr Ser Leu Ser Arg Asp Cys Asn
    355                 360                 365

Thr Cys Ile Cys Arg Asn Ser Gln Trp Ile Cys Ser Asn Glu Glu Cys
370                 375                 380

Pro Gly Glu Cys Leu Val Thr Gly Gln Ser His Phe Lys Ser Phe Asp
385                 390                 395                 400

Asn Arg Tyr Phe Thr Phe Ser Gly Ile Cys Gln Tyr Leu Leu Ala Arg
            405                 410                 415

Asp Cys Gln Asp His Ser Phe Ser Ile Val Ile Glu Thr Val Gln Cys
        420                 425                 430

Ala Asp Asp Arg Asp Ala Val Cys Thr Arg Ser Val Thr Val Arg Leu
    435                 440                 445

Pro Gly Leu His Asn Ser Leu Val Lys Leu Lys His Gly Ala Gly Val
450                 455                 460

Ala Met Asp Gly Gln Asp Val Gln Leu Pro Leu Leu Lys Gly Asp Leu
465                 470                 475                 480

Arg Ile Gln His Thr Val Thr Ala Ser Val Arg Leu Ser Tyr Gly Glu
            485                 490                 495

Asp Leu Gln Met Asp Trp Asp Gly Arg Gly Arg Leu Leu Val Lys Leu
        500                 505                 510

Ser Pro Val Tyr Ala Gly Lys Thr Cys Gly Leu Cys Gly Asn Tyr Asn
    515                 520                 525

Gly Asn Gln Gly Asp Asp Phe Leu Thr Pro Ser Gly Leu Ala Glu Pro
530                 535                 540

Arg Val Glu Asp Phe Gly Asn Ala Trp Lys Leu His Gly Asp Cys Gln
545                 550                 555                 560

Asp Leu Gln Lys Gln His Ser Asp Pro Cys Ala Leu Asn Pro Arg Met
            565                 570                 575

Thr Arg Phe Ser Glu Glu Ala Cys Ala Val Leu Thr Ser Pro Thr Phe
        580                 585                 590

Glu Ala Cys His Arg Ala Val Ser Pro Leu Pro Tyr Leu Arg Asn Cys
    595                 600                 605

Arg Tyr Asp Val Cys Ser Cys Ser Asp Gly Arg Glu Cys Leu Cys Gly
610                 615                 620

Ala Leu Ala Ser Tyr Ala Ala Ala Cys Ala Gly Arg Gly Val Arg Val
625                 630                 635                 640

Ala Trp Arg Glu Pro Gly Arg Cys Glu Leu Asn Cys Pro Lys Gly Gln
            645                 650                 655

Val Tyr Leu Gln Cys Gly Thr Pro Cys Asn Leu Thr Cys Arg Ser Leu

```
              660                 665                 670
Ser Tyr Pro Asp Glu Cys Asn Glu Ala Cys Leu Glu Gly Cys Phe
            675                 680                 685

Cys Pro Pro Gly Leu Tyr Met Asp Glu Arg Gly Asp Cys Val Pro Lys
        690                 695                 700

Ala Gln Cys Pro Cys Tyr Tyr Asp Gly Glu Ile Phe Gln Pro Glu Asp
705                 710                 715                 720

Ile Phe Ser Asp His His Thr Met Cys Tyr Cys Glu Asp Gly Phe Met
                725                 730                 735

His Cys Thr Met Ser Gly Val Pro Gly Ser Leu Leu Pro Asp Ala Val
            740                 745                 750

Leu Ser Ser Pro Leu Ser His Arg Ser Lys Arg Ser Leu Ser Cys Arg
        755                 760                 765

Pro Pro Met Val Lys Leu Val Cys Pro Ala Asp Asn Leu Arg Ala Glu
        770                 775                 780

Gly Leu Glu Cys Thr Lys Thr Cys Gln Asn Tyr Asp Leu Glu Cys Met
785                 790                 795                 800

Ser Met Gly Cys Val Ser Gly Cys Leu Cys Pro Pro Gly Met Val Arg
                805                 810                 815

His Glu Asn Arg Cys Val Ala Leu Glu Arg Cys Pro Cys Phe His Gln
            820                 825                 830

Gly Lys Glu Tyr Ala Pro Gly Glu Thr Val Lys Ile Gly Cys Asn Thr
        835                 840                 845

Cys Val Cys Arg Asp Arg Lys Trp Asn Cys Thr Asp His Val Cys Asp
        850                 855                 860

Ala Thr Cys Ser Thr Ile Gly Met Ala His Tyr Leu Thr Phe Asp Gly
865                 870                 875                 880

Leu Lys Tyr Leu Phe Pro Gly Glu Cys Gln Tyr Val Leu Val Gln Asp
                885                 890                 895

Tyr Cys Gly Ser Asn Pro Gly Thr Phe Arg Ile Leu Val Gly Asn Lys
            900                 905                 910

Gly Cys Ser His Pro Ser Val Lys Cys Lys Lys Arg Val Thr Ile Leu
        915                 920                 925

Val Glu Gly Gly Glu Ile Glu Leu Phe Asp Gly Glu Val Asn Val Lys
        930                 935                 940

Arg Pro Met Lys Asp Glu Thr His Phe Glu Val Val Glu Ser Gly Arg
945                 950                 955                 960

Tyr Ile Ile Leu Leu Leu Gly Lys Ala Leu Ser Val Val Trp Asp Arg
                965                 970                 975

His Leu Ser Ile Ser Val Val Leu Lys Gln Thr Tyr Gln Glu Lys Val
            980                 985                 990

Cys Gly Leu Cys Gly Asn Phe Asp  Gly Ile Gln Asn Asn  Asp Leu Thr
        995                 1000                 1005

Ser Ser  Asn Leu Gln Val Glu  Glu Asp Pro Val Asp  Phe Gly Asn
    1010                 1015                 1020

Ser Trp Lys Val Ser Ser Gln  Cys Ala Asp Thr Arg  Lys Val Pro
    1025                 1030                 1035

Leu Asp  Ser Ser Pro Ala Thr  Cys His Asn Asn Ile  Met Lys Gln
    1040                 1045                 1050

Thr Met  Val Asp Ser Ser Cys  Arg Ile Leu Thr Ser  Asp Val Phe
    1055                 1060                 1065

Gln Asp  Cys Asn Lys Leu Val  Asp Pro Glu Pro Tyr  Leu Asp Val
    1070                 1075                 1080
```

```
Cys Ile Tyr Asp Thr Cys Ser Cys Glu Ser Ile Gly Asp Cys Ala
1085                1090                1095

Cys Phe Cys Asp Thr Ile Ala Ala Tyr Ala His Val Cys Ala Gln
1100                1105                1110

His Gly Lys Val Val Thr Trp Arg Thr Ala Thr Leu Cys Pro Gln
1115                1120                1125

Ser Cys Glu Glu Arg Asn Leu Arg Glu Asn Gly Tyr Glu Cys Glu
1130                1135                1140

Trp Arg Tyr Asn Ser Cys Ala Pro Ala Cys Gln Val Thr Cys Gln
1145                1150                1155

His Pro Glu Pro Leu Ala Cys Pro Val Gln Cys Val Glu Gly Cys
1160                1165                1170

His Ala His Cys Pro Pro Gly Lys Ile Leu Asp Glu Leu Leu Gln
1175                1180                1185

Thr Cys Val Asp Pro Glu Asp Cys Pro Val Cys Glu Val Ala Gly
1190                1195                1200

Arg Arg Phe Ala Ser Gly Lys Lys Val Thr Leu Asn Pro Ser Asp
1205                1210                1215

Pro Glu His Cys Gln Ile Cys His Cys Asp Val Val Asn Leu Thr
1220                1225                1230

Cys Glu Ala Cys Gln Glu Pro Gly Gly Leu Val Val Pro Pro Thr
1235                1240                1245

Asp Ala Pro Val Ser Pro Thr Thr Leu Tyr Val Glu Asp Ile Ser
1250                1255                1260

Glu Pro Pro Leu His Asp Phe Tyr Cys Ser Arg Leu Leu Asp Leu
1265                1270                1275

Val Phe Leu Leu Asp Gly Ser Ser Arg Leu Ser Glu Ala Glu Phe
1280                1285                1290

Glu Val Leu Lys Ala Phe Val Val Asp Met Met Glu Arg Leu Arg
1295                1300                1305

Ile Ser Gln Lys Trp Val Arg Val Ala Val Val Glu Tyr His Asp
1310                1315                1320

Gly Ser His Ala Tyr Ile Gly Leu Lys Asp Arg Lys Arg Pro Ser
1325                1330                1335

Glu Leu Arg Arg Ile Ala Ser Gln Val Lys Tyr Ala Gly Ser Gln
1340                1345                1350

Val Ala Ser Thr Ser Glu Val Leu Lys Tyr Thr Leu Phe Gln Ile
1355                1360                1365

Phe Ser Lys Ile Asp Arg Pro Glu Ala Ser Arg Ile Ala Leu Leu
1370                1375                1380

Leu Met Ala Ser Gln Glu Pro Gln Arg Met Ser Arg Asn Phe Val
1385                1390                1395

Arg Tyr Val Gln Gly Leu Lys Lys Lys Lys Val Ile Val Ile Pro
1400                1405                1410

Val Gly Ile Gly Pro His Ala Asn Leu Lys Gln Ile Arg Leu Ile
1415                1420                1425

Glu Lys Gln Ala Pro Glu Asn Lys Ala Phe Val Leu Ser Ser Val
1430                1435                1440

Asp Glu Leu Glu Gln Gln Arg Asp Glu Ile Val Ser Tyr Leu Cys
1445                1450                1455

Asp Leu Ala Pro Glu Ala Pro Pro Pro Thr Leu Pro Pro His Met
1460                1465                1470
```

| | | | | | | | | | |
|---|---|---|---|---|---|---|---|---|---|
|Ala|Gln|Val|Thr|Val|Gly|Pro|Gly|Leu|Leu|Gly|Val|Ser|Thr|Leu|
|1475| | | | |1480| | | | |1485| | | | |

Gly Pro Lys Arg Asn Ser Met Val Leu Asp Val Ala Phe Val Leu
1490                    1495                    1500

Glu Gly Ser Asp Lys Ile Gly Glu Ala Asp Phe Asn Arg Ser Lys
1505                    1510                    1515

Glu Phe Met Glu Glu Val Ile Gln Arg Met Asp Val Gly Gln Asp
1520                    1525                    1530

Ser Ile His Val Thr Val Leu Gln Tyr Ser Tyr Met Val Thr Val
1535                    1540                    1545

Glu Tyr Pro Phe Ser Glu Ala Gln Ser Lys Gly Asp Ile Leu Gln
1550                    1555                    1560

Arg Val Arg Glu Ile Arg Tyr Gln Gly Gly Asn Arg Thr Asn Thr
1565                    1570                    1575

Gly Leu Ala Leu Arg Tyr Leu Ser Asp His Ser Phe Leu Val Ser
1580                    1585                    1590

Gln Gly Asp Arg Glu Gln Ala Pro Asn Leu Val Tyr Met Val Thr
1595                    1600                    1605

Gly Asn Pro Ala Ser Asp Glu Ile Lys Arg Leu Pro Gly Asp Ile
1610                    1615                    1620

Gln Val Val Pro Ile Gly Val Gly Pro Asn Ala Asn Val Gln Glu
1625                    1630                    1635

Leu Glu Arg Ile Gly Trp Pro Asn Ala Pro Ile Leu Ile Gln Asp
1640                    1645                    1650

Phe Glu Thr Leu Pro Arg Glu Ala Pro Asp Leu Val Leu Gln Arg
1655                    1660                    1665

Cys Cys Ser Gly Glu Gly Leu Gln Ile Pro Thr Leu Ser Pro Ala
1670                    1675                    1680

Pro Asp Cys Ser Gln Pro Leu Asp Val Ile Leu Leu Leu Asp Gly
1685                    1690                    1695

Ser Ser Ser Phe Pro Ala Ser Tyr Phe Asp Glu Met Lys Ser Phe
1700                    1705                    1710

Ala Lys Ala Phe Ile Ser Lys Ala Asn Ile Gly Pro Arg Leu Thr
1715                    1720                    1725

Gln Val Ser Val Leu Gln Tyr Gly Ser Ile Thr Thr Ile Asp Val
1730                    1735                    1740

Pro Trp Asn Val Val Pro Glu Lys Ala His Leu Leu Ser Leu Val
1745                    1750                    1755

Asp Val Met Gln Arg Glu Gly Gly Pro Ser Gln Ile Gly Asp Ala
1760                    1765                    1770

Leu Gly Phe Ala Val Arg Tyr Leu Thr Ser Glu Met His Gly Ala
1775                    1780                    1785

Arg Pro Gly Ala Ser Lys Ala Val Val Ile Leu Val Thr Asp Val
1790                    1795                    1800

Ser Val Asp Ser Val Asp Ala Ala Ala Asp Ala Ala Arg Ser Asn
1805                    1810                    1815

Arg Val Thr Val Phe Pro Ile Gly Ile Gly Asp Arg Tyr Asp Ala
1820                    1825                    1830

Ala Gln Leu Arg Ile Leu Ala Gly Pro Ala Gly Asp Ser Asn Val
1835                    1840                    1845

Val Lys Leu Gln Arg Ile Glu Asp Leu Pro Thr Met Val Thr Leu
1850                    1855                    1860

Gly Asn Ser Phe Leu His Lys Leu Cys Ser Gly Phe Val Arg Ile

```
                1865                1870                1875
Cys Met Asp Glu Asp Gly Asn Glu Lys Arg Pro Gly Asp Val Trp
        1880                1885                1890
Thr Leu Pro Asp Gln Cys His Thr Val Thr Cys Gln Pro Asp Gly
        1895                1900                1905
Gln Thr Leu Leu Lys Ser His Arg Val Asn Cys Asp Arg Gly Leu
        1910                1915                1920
Arg Pro Ser Cys Pro Asn Ser Gln Ser Pro Val Lys Val Glu Glu
        1925                1930                1935
Thr Cys Gly Cys Arg Trp Thr Cys Pro Cys Val Cys Thr Gly Ser
        1940                1945                1950
Ser Thr Arg His Ile Val Thr Phe Asp Gly Gln Asn Phe Lys Leu
        1955                1960                1965
Thr Gly Ser Cys Ser Tyr Val Leu Phe Gln Asn Lys Glu Gln Asp
        1970                1975                1980
Leu Glu Val Ile Leu His Asn Gly Ala Cys Ser Pro Gly Ala Arg
        1985                1990                1995
Gln Gly Cys Met Lys Ser Ile Glu Val Lys His Ser Ala Leu Ser
        2000                2005                2010
Val Glu Leu His Ser Asp Met Glu Val Thr Val Asn Gly Arg Leu
        2015                2020                2025
Val Ser Val Pro Tyr Val Gly Gly Asn Met Glu Val Asn Val Tyr
        2030                2035                2040
Gly Ala Ile Met His Glu Val Arg Phe Asn His Leu Gly His Ile
        2045                2050                2055
Phe Thr Phe Thr Pro Gln Asn Asn Glu Phe Gln Leu Gln Leu Ser
        2060                2065                2070
Pro Lys Thr Phe Ala Ser Lys Thr Tyr Gly Leu Cys Gly Ile Cys
        2075                2080                2085
Asp Glu Asn Gly Ala Asn Asp Phe Met Leu Arg Asp Gly Thr Val
        2090                2095                2100
Thr Thr Asp Trp Lys Thr Leu Val Gln Glu Trp Thr Val Gln Arg
        2105                2110                2115
Pro Gly Gln Thr Cys Gln Pro Ile Leu Glu Glu Gln Cys Leu Val
        2120                2125                2130
Pro Asp Ser Ser His Cys Gln Val Leu Leu Leu Pro Leu Phe Ala
        2135                2140                2145
Glu Cys His Lys Val Leu Ala Pro Ala Thr Phe Tyr Ala Ile Cys
        2150                2155                2160
Gln Gln Asp Ser Cys His Gln Glu Gln Val Cys Glu Val Ile Ala
        2165                2170                2175
Ser Tyr Ala His Leu Cys Arg Thr Asn Gly Val Cys Val Asp Trp
        2180                2185                2190
Arg Thr Pro Asp Phe Cys Ala Met Ser Cys Pro Pro Ser Leu Val
        2195                2200                2205
Tyr Asn His Cys Glu His Gly Cys Pro Arg His Cys Asp Gly Asn
        2210                2215                2220
Val Ser Ser Cys Gly Asp His Pro Ser Glu Gly Cys Phe Cys Pro
        2225                2230                2235
Pro Asp Lys Val Met Leu Glu Gly Ser Cys Val Pro Glu Glu Ala
        2240                2245                2250
Cys Thr Gln Cys Ile Gly Glu Asp Gly Val Gln His Gln Phe Leu
        2255                2260                2265
```

```
Glu Ala Trp Val Pro Asp His Gln Pro Cys Gln Ile Cys Thr Cys
        2270            2275            2280

Leu Ser Gly Arg Lys Val Asn Cys Thr Thr Gln Pro Cys Pro Thr
    2285            2290            2295

Ala Lys Ala Pro Thr Cys Gly Leu Cys Glu Val Ala Arg Leu Arg
    2300            2305            2310

Gln Asn Ala Asp Gln Cys Cys Pro Glu Tyr Glu Cys Val Cys Asp
    2315            2320            2325

Pro Val Ser Cys Asp Leu Pro Pro Val Pro His Cys Glu Arg Gly
    2330            2335            2340

Leu Gln Pro Thr Leu Thr Asn Pro Gly Glu Cys Arg Pro Asn Phe
    2345            2350            2355

Thr Cys Ala Cys Arg Lys Glu Glu Cys Lys Arg Val Ser Pro Pro
    2360            2365            2370

Ser Cys Pro Pro His Arg Leu Pro Thr Leu Arg Lys Thr Gln Cys
    2375            2380            2385

Cys Asp Glu Tyr Glu Cys Ala Cys Asn Cys Val Asn Ser Thr Val
    2390            2395            2400

Ser Cys Pro Leu Gly Tyr Leu Ala Ser Thr Ala Thr Asn Asp Cys
    2405            2410            2415

Gly Cys Thr Thr Thr Thr Cys Leu Pro Asp Lys Val Cys Val His
    2420            2425            2430

Arg Ser Thr Ile Tyr Pro Val Gly Gln Phe Trp Glu Glu Gly Cys
    2435            2440            2445

Asp Val Cys Thr Cys Thr Asp Met Glu Asp Ala Val Met Gly Leu
    2450            2455            2460

Arg Val Ala Gln Cys Ser Gln Lys Pro Cys Glu Asp Ser Cys Arg
    2465            2470            2475

Ser Gly Phe Thr Tyr Val Leu His Glu Gly Glu Cys Cys Gly Arg
    2480            2485            2490

Cys Leu Pro Ser Ala Cys Glu Val Val Thr Gly Ser Pro Arg Gly
    2495            2500            2505

Asp Ser Gln Ser Ser Trp Lys Ser Val Gly Ser Gln Trp Ala Ser
    2510            2515            2520

Pro Glu Asn Pro Cys Leu Ile Asn Glu Cys Val Arg Val Lys Glu
    2525            2530            2535

Glu Val Phe Ile Gln Gln Arg Asn Val Ser Cys Pro Gln Leu Glu
    2540            2545            2550

Val Pro Val Cys Pro Ser Gly Phe Gln Leu Ser Cys Lys Thr Ser
    2555            2560            2565

Ala Cys Cys Pro Ser Cys Arg Cys Glu Arg Met Glu Ala Cys Met
    2570            2575            2580

Leu Asn Gly Thr Val Ile Gly Pro Gly Lys Thr Val Met Ile Asp
    2585            2590            2595

Val Cys Thr Thr Cys Arg Cys Met Val Gln Val Gly Val Ile Ser
    2600            2605            2610

Gly Phe Lys Leu Glu Cys Arg Lys Thr Thr Cys Asn Pro Cys Pro
    2615            2620            2625

Leu Gly Tyr Lys Glu Glu Asn Asn Thr Gly Glu Cys Cys Gly Arg
    2630            2635            2640

Cys Leu Pro Thr Ala Cys Thr Ile Gln Leu Arg Gly Gly Gln Ile
    2645            2650            2655
```

```
Met Thr Leu Lys Arg Asp Glu Thr Leu Gln Asp Gly Cys Asp Thr
            2660            2665            2670

His Phe Cys Lys Val Asn Glu Arg Gly Glu Tyr Phe Trp Glu Lys
    2675            2680            2685

Arg Val Thr Gly Cys Pro Pro Phe Asp Glu His Lys Cys Leu Ala
        2690            2695            2700

Glu Gly Gly Lys Ile Met Lys Ile Pro Gly Thr Cys Cys Asp Thr
    2705            2710            2715

Cys Glu Pro Glu Cys Asn Asp Ile Thr Ala Arg Leu Gln Tyr
    2720            2725            2730

Val Lys Val Gly Ser Cys Lys Ser Glu Val Glu Val Asp Ile His
    2735            2740            2745

Tyr Cys Gln Gly Lys Cys Ala Ser Lys Ala Met Tyr Ser Ile Asp
    2750            2755            2760

Ile Asn Asp Val Gln Asp Gln Cys Ser Cys Cys Ser Pro Thr Arg
    2765            2770            2775

Thr Glu Pro Met Gln Val Ala Leu His Cys Thr Asn Gly Ser Val
    2780            2785            2790

Val Tyr His Glu Val Leu Asn Ala Met Glu Cys Lys Cys Ser Pro
    2795            2800            2805

Arg Lys Cys Ser Lys
    2810
```

<210> SEQ ID NO 3
<211> LENGTH: 30
<212> TYPE: DNA
<213> ORGANISM: Artificial Sequence
<220> FEATURE:
<223> OTHER INFORMATION: PCR primer VWF+

<400> SEQUENCE: 3
ttcgaattcc cgcagccctc atttgcaggg                                    30

<210> SEQ ID NO 4
<211> LENGTH: 31
<212> TYPE: DNA
<213> ORGANISM: Artificial Sequence
<220> FEATURE:
<223> OTHER INFORMATION: PCR primer VWF-

<400> SEQUENCE: 4
tccgaattcc ggcagcagca ggcacccatg c                                  31

<210> SEQ ID NO 5
<211> LENGTH: 30
<212> TYPE: DNA
<213> ORGANISM: Artificial Sequence
<220> FEATURE:
<223> OTHER INFORMATION: PCR primer VWFT2298Q+

<400> SEQUENCE: 5
gcagccctgc ccccaggcca aagctcccac                                    30

<210> SEQ ID NO 6
<211> LENGTH: 30
<212> TYPE: DNA
<213> ORGANISM: Artificial Sequence
<220> FEATURE:
<223> OTHER INFORMATION: PCR primer VWFT2298Q-

<400> SEQUENCE: 6

```
gtgggagctt tggcctgggg gcagggctgc                                    30
```

<210> SEQ ID NO 7
<211> LENGTH: 28
<212> TYPE: DNA
<213> ORGANISM: Artificial Sequence
<220> FEATURE:
<223> OTHER INFORMATION: PCR primer HA+

<400> SEQUENCE: 7

```
ggatccgatg cacacaagag tgaggttg                                      28
```

<210> SEQ ID NO 8
<211> LENGTH: 31
<212> TYPE: DNA
<213> ORGANISM: Artificial Sequence
<220> FEATURE:
<223> OTHER INFORMATION: PCR primer HA-

<400> SEQUENCE: 8

```
gcggccgcct ataagcctaa ggcagcttga c                                  31
```

<210> SEQ ID NO 9
<211> LENGTH: 686
<212> TYPE: PRT
<213> ORGANISM: Artificial Sequence
<220> FEATURE:
<223> OTHER INFORMATION: Signal peptide (1-22); VWF fragment aa 2276 to
      2326 (23 - 73); glycin/serin linker (74 - 101); albumin (102 -
      686)

<400> SEQUENCE: 9

Met Ile Pro Ala Arg Phe Ala Gly Val Leu Leu Ala Leu Ala Leu Ile
1               5                   10                  15

Leu Pro Gly Thr Leu Cys Gln Pro Cys Gln Ile Cys Thr Cys Leu Ser
            20                  25                  30

Gly Arg Lys Val Asn Cys Thr Thr Gln Pro Cys Pro Thr Ala Lys Ala
        35                  40                  45

Pro Thr Cys Gly Leu Cys Glu Val Ala Arg Leu Arg Gln Asn Ala Asp
    50                  55                  60

Gln Cys Cys Pro Glu Tyr Glu Cys Val Gly Ser Gly Gly Ser Gly Gly
65                  70                  75                  80

Ser Gly Gly Ser Gly Gly Ser Gly Gly Ser Gly Gly Ser Gly Gly Ser
                85                  90                  95

Gly Gly Ser Gly Ser Asp Ala His Lys Ser Glu Val Ala His Arg Phe
            100                 105                 110

Lys Asp Leu Gly Glu Glu Asn Phe Lys Ala Leu Val Leu Ile Ala Phe
        115                 120                 125

Ala Gln Tyr Leu Gln Gln Cys Pro Phe Glu Asp His Val Lys Leu Val
    130                 135                 140

Asn Glu Val Thr Glu Phe Ala Lys Thr Cys Val Ala Asp Glu Ser Ala
145                 150                 155                 160

Glu Asn Cys Asp Lys Ser Leu His Thr Leu Phe Gly Asp Lys Leu Cys
                165                 170                 175

Thr Val Ala Thr Leu Arg Glu Thr Tyr Gly Glu Met Ala Asp Cys Cys
            180                 185                 190

Ala Lys Gln Glu Pro Glu Arg Asn Glu Cys Phe Leu Gln His Lys Asp
        195                 200                 205

Asp Asn Pro Asn Leu Pro Arg Leu Val Arg Pro Glu Val Asp Val Met
    210                 215                 220

```
Cys Thr Ala Phe His Asp Asn Glu Glu Thr Phe Leu Lys Lys Tyr Leu
225                 230                 235                 240

Tyr Glu Ile Ala Arg Arg His Pro Tyr Phe Tyr Ala Pro Glu Leu Leu
            245                 250                 255

Phe Phe Ala Lys Arg Tyr Lys Ala Ala Phe Thr Glu Cys Cys Gln Ala
        260                 265                 270

Ala Asp Lys Ala Ala Cys Leu Leu Pro Lys Leu Asp Glu Leu Arg Asp
    275                 280                 285

Glu Gly Lys Ala Ser Ser Ala Lys Gln Arg Leu Lys Cys Ala Ser Leu
290                 295                 300

Gln Lys Phe Gly Glu Arg Ala Phe Lys Ala Trp Ala Val Ala Arg Leu
305                 310                 315                 320

Ser Gln Arg Phe Pro Lys Ala Glu Phe Ala Glu Val Ser Lys Leu Val
            325                 330                 335

Thr Asp Leu Thr Lys Val His Thr Glu Cys Cys His Gly Asp Leu Leu
        340                 345                 350

Glu Cys Ala Asp Asp Arg Ala Asp Leu Ala Lys Tyr Ile Cys Glu Asn
    355                 360                 365

Gln Asp Ser Ile Ser Ser Lys Leu Lys Glu Cys Cys Glu Lys Pro Leu
370                 375                 380

Leu Glu Lys Ser His Cys Ile Ala Glu Val Glu Asn Asp Glu Met Pro
385                 390                 395                 400

Ala Asp Leu Pro Ser Leu Ala Ala Asp Phe Val Glu Ser Lys Asp Val
            405                 410                 415

Cys Lys Asn Tyr Ala Glu Ala Lys Asp Val Phe Leu Gly Met Phe Leu
        420                 425                 430

Tyr Glu Tyr Ala Arg Arg His Pro Asp Tyr Ser Val Val Leu Leu Leu
    435                 440                 445

Arg Leu Ala Lys Thr Tyr Glu Thr Thr Leu Glu Lys Cys Cys Ala Ala
450                 455                 460

Ala Asp Pro His Glu Cys Tyr Ala Lys Val Phe Asp Glu Phe Lys Pro
465                 470                 475                 480

Leu Val Glu Glu Pro Gln Asn Leu Ile Lys Gln Asn Cys Glu Leu Phe
            485                 490                 495

Glu Gln Leu Gly Glu Tyr Lys Phe Gln Asn Ala Leu Leu Val Arg Tyr
        500                 505                 510

Thr Lys Lys Val Pro Gln Val Ser Thr Pro Thr Leu Val Glu Val Ser
    515                 520                 525

Arg Asn Leu Gly Lys Val Gly Ser Lys Cys Cys Lys His Pro Glu Ala
530                 535                 540

Lys Arg Met Pro Cys Ala Glu Asp Tyr Leu Ser Val Val Leu Asn Gln
545                 550                 555                 560

Leu Cys Val Leu His Glu Lys Thr Pro Val Ser Asp Arg Val Thr Lys
            565                 570                 575

Cys Cys Thr Glu Ser Leu Val Asn Arg Arg Pro Cys Phe Ser Ala Leu
        580                 585                 590

Glu Val Asp Glu Thr Tyr Val Pro Lys Glu Phe Asn Ala Glu Thr Phe
    595                 600                 605

Thr Phe His Ala Asp Ile Cys Thr Leu Ser Glu Lys Glu Arg Gln Ile
610                 615                 620

Lys Lys Gln Thr Ala Leu Val Glu Leu Val Lys His Lys Pro Lys Ala
625                 630                 635                 640
```

```
Thr Lys Glu Gln Leu Lys Ala Val Met Asp Asp Phe Ala Ala Phe Val
            645                 650                 655

Glu Lys Cys Cys Lys Ala Asp Asp Lys Glu Thr Cys Phe Ala Glu Glu
        660                 665                 670

Gly Lys Lys Leu Val Ala Ala Ser Gln Ala Ala Leu Gly Leu
    675                 680                 685

<210> SEQ ID NO 10
<211> LENGTH: 74
<212> TYPE: PRT
<213> ORGANISM: Artificial Sequence
<220> FEATURE:
<223> OTHER INFORMATION: C1 domain of modified VWF having a mutation at
      T2298
<220> FEATURE:
<221> NAME/KEY: MISC_FEATURE
<222> LOCATION: (44)..(44)
<223> OTHER INFORMATION: Xaa is absent or an amino acid other than
      threonine and serine

<400> SEQUENCE: 10

Thr Gln Cys Ile Gly Glu Asp Gly Val Gln His Gln Phe Leu Glu Ala
1               5                   10                  15

Trp Val Pro Asp His Gln Pro Cys Gln Ile Cys Thr Cys Leu Ser Gly
            20                  25                  30

Arg Lys Val Asn Cys Thr Thr Gln Pro Cys Pro Xaa Ala Lys Ala Pro
        35                  40                  45

Thr Cys Gly Leu Cys Glu Val Ala Arg Leu Arg Gln Asn Ala Asp Gln
    50                  55                  60

Cys Cys Pro Glu Tyr Glu Cys Val Cys Asp
65                  70

<210> SEQ ID NO 11
<211> LENGTH: 2050
<212> TYPE: PRT
<213> ORGANISM: Artificial Sequence
<220> FEATURE:
<223> OTHER INFORMATION: Mature form of modified VWF having a mutation
      of T2298
<220> FEATURE:
<221> NAME/KEY: MISC_FEATURE
<222> LOCATION: (1535)..(1535)
<223> OTHER INFORMATION: Xaa is absent or an amino acid other than
      threonine and serine

<400> SEQUENCE: 11

Ser Leu Ser Cys Arg Pro Pro Met Val Lys Leu Val Cys Pro Ala Asp
1               5                   10                  15

Asn Leu Arg Ala Glu Gly Leu Glu Cys Thr Lys Thr Cys Gln Asn Tyr
            20                  25                  30

Asp Leu Glu Cys Met Ser Met Gly Cys Val Ser Gly Cys Leu Cys Pro
        35                  40                  45

Pro Gly Met Val Arg His Glu Asn Arg Cys Val Ala Leu Glu Arg Cys
    50                  55                  60

Pro Cys Phe His Gln Gly Lys Glu Tyr Ala Pro Gly Glu Thr Val Lys
65                  70                  75                  80

Ile Gly Cys Asn Thr Cys Val Cys Arg Asp Arg Lys Trp Asn Cys Thr
                85                  90                  95

Asp His Val Cys Asp Ala Thr Cys Ser Thr Ile Gly Met Ala His Tyr
            100                 105                 110

Leu Thr Phe Asp Gly Leu Lys Tyr Leu Phe Pro Gly Glu Cys Gln Tyr
        115                 120                 125
```

```
Val Leu Val Gln Asp Tyr Cys Gly Ser Asn Pro Thr Phe Arg Ile
    130                 135                 140
Leu Val Gly Asn Lys Gly Cys Ser His Pro Ser Val Lys Cys Lys Lys
145                 150                 155                 160
Arg Val Thr Ile Leu Val Glu Gly Glu Ile Glu Leu Phe Asp Gly
                165                 170                 175
Glu Val Asn Val Lys Arg Pro Met Lys Asp Glu Thr His Phe Glu Val
                180                 185                 190
Val Glu Ser Gly Arg Tyr Ile Ile Leu Leu Gly Lys Ala Leu Ser
            195                 200                 205
Val Val Trp Asp Arg His Leu Ser Ile Ser Val Leu Lys Gln Thr
    210                 215                 220
Tyr Gln Glu Lys Val Cys Gly Leu Cys Gly Asn Phe Asp Gly Ile Gln
225                 230                 235                 240
Asn Asn Asp Leu Thr Ser Ser Asn Leu Gln Val Glu Glu Asp Pro Val
                245                 250                 255
Asp Phe Gly Asn Ser Trp Lys Val Ser Ser Gln Cys Ala Asp Thr Arg
            260                 265                 270
Lys Val Pro Leu Asp Ser Ser Pro Ala Thr Cys His Asn Asn Ile Met
        275                 280                 285
Lys Gln Thr Met Val Asp Ser Ser Cys Arg Ile Leu Thr Ser Asp Val
    290                 295                 300
Phe Gln Asp Cys Asn Lys Leu Val Asp Pro Glu Pro Tyr Leu Asp Val
305                 310                 315                 320
Cys Ile Tyr Asp Thr Cys Ser Cys Glu Ser Ile Gly Asp Cys Ala Cys
                325                 330                 335
Phe Cys Asp Thr Ile Ala Ala Tyr Ala His Val Cys Ala Gln His Gly
            340                 345                 350
Lys Val Val Thr Trp Arg Thr Ala Thr Leu Cys Pro Gln Ser Cys Glu
        355                 360                 365
Glu Arg Asn Leu Arg Glu Asn Gly Tyr Glu Cys Glu Trp Arg Tyr Asn
    370                 375                 380
Ser Cys Ala Pro Ala Cys Gln Val Thr Cys Gln His Pro Glu Pro Leu
385                 390                 395                 400
Ala Cys Pro Val Gln Cys Val Glu Gly Cys His Ala His Cys Pro Pro
                405                 410                 415
Gly Lys Ile Leu Asp Glu Leu Leu Gln Thr Cys Val Asp Pro Glu Asp
            420                 425                 430
Cys Pro Val Cys Glu Val Ala Gly Arg Arg Phe Ala Ser Gly Lys Lys
        435                 440                 445
Val Thr Leu Asn Pro Ser Asp Pro Glu His Cys Gln Ile Cys His Cys
    450                 455                 460
Asp Val Val Asn Leu Thr Cys Glu Ala Cys Gln Glu Pro Gly Gly Leu
465                 470                 475                 480
Val Val Pro Pro Thr Asp Ala Pro Val Ser Pro Thr Thr Leu Tyr Val
                485                 490                 495
Glu Asp Ile Ser Glu Pro Pro Leu His Asp Phe Tyr Cys Ser Arg Leu
            500                 505                 510
Leu Asp Leu Val Phe Leu Leu Asp Gly Ser Ser Arg Leu Ser Glu Ala
        515                 520                 525
Glu Phe Glu Val Leu Lys Ala Phe Val Val Asp Met Met Glu Arg Leu
    530                 535                 540
```

```
Arg Ile Ser Gln Lys Trp Val Arg Val Ala Val Glu Tyr His Asp
545                 550                 555                 560

Gly Ser His Ala Tyr Ile Gly Leu Lys Asp Arg Lys Arg Pro Ser Glu
            565                 570                 575

Leu Arg Arg Ile Ala Ser Gln Val Lys Tyr Ala Gly Ser Gln Val Ala
                580                 585                 590

Ser Thr Ser Glu Val Leu Lys Tyr Thr Leu Phe Gln Ile Phe Ser Lys
            595                 600                 605

Ile Asp Arg Pro Glu Ala Ser Arg Ile Ala Leu Leu Met Ala Ser
610                 615                 620

Gln Glu Pro Gln Arg Met Ser Arg Asn Phe Val Arg Tyr Val Gln Gly
625                 630                 635                 640

Leu Lys Lys Lys Val Ile Ile Pro Val Gly Ile Gly Pro His
                645                 650                 655

Ala Asn Leu Lys Gln Ile Arg Leu Ile Glu Lys Gln Ala Pro Glu Asn
            660                 665                 670

Lys Ala Phe Val Leu Ser Ser Val Asp Glu Leu Glu Gln Gln Arg Asp
            675                 680                 685

Glu Ile Val Ser Tyr Leu Cys Asp Leu Ala Pro Glu Ala Pro Pro
690                 695                 700

Thr Leu Pro Pro His Met Ala Gln Val Thr Val Gly Pro Gly Leu Leu
705                 710                 715                 720

Gly Val Ser Thr Leu Gly Pro Lys Arg Asn Ser Met Val Leu Asp Val
            725                 730                 735

Ala Phe Val Leu Glu Gly Ser Asp Lys Ile Gly Glu Ala Asp Phe Asn
            740                 745                 750

Arg Ser Lys Glu Phe Met Glu Glu Val Ile Gln Arg Met Asp Val Gly
            755                 760                 765

Gln Asp Ser Ile His Val Thr Val Leu Gln Tyr Ser Tyr Met Val Thr
770                 775                 780

Val Glu Tyr Pro Phe Ser Glu Ala Gln Ser Lys Gly Asp Ile Leu Gln
785                 790                 795                 800

Arg Val Arg Glu Ile Arg Tyr Gln Gly Gly Asn Arg Thr Asn Thr Gly
                805                 810                 815

Leu Ala Leu Arg Tyr Leu Ser Asp His Ser Phe Leu Val Ser Gln Gly
            820                 825                 830

Asp Arg Glu Gln Ala Pro Asn Leu Val Tyr Met Val Thr Gly Asn Pro
            835                 840                 845

Ala Ser Asp Glu Ile Lys Arg Leu Pro Gly Asp Ile Gln Val Val Pro
850                 855                 860

Ile Gly Val Gly Pro Asn Ala Asn Val Gln Glu Leu Glu Arg Ile Gly
865                 870                 875                 880

Trp Pro Asn Ala Pro Ile Leu Ile Gln Asp Phe Glu Thr Leu Pro Arg
                885                 890                 895

Glu Ala Pro Asp Leu Val Leu Gln Arg Cys Cys Ser Gly Glu Gly Leu
            900                 905                 910

Gln Ile Pro Thr Leu Ser Pro Ala Pro Asp Cys Ser Gln Pro Leu Asp
            915                 920                 925

Val Ile Leu Leu Leu Asp Gly Ser Ser Ser Phe Pro Ala Ser Tyr Phe
            930                 935                 940

Asp Glu Met Lys Ser Phe Ala Lys Ala Phe Ile Ser Lys Ala Asn Ile
945                 950                 955                 960

Gly Pro Arg Leu Thr Gln Val Ser Val Leu Gln Tyr Gly Ser Ile Thr
```

-continued

```
                965                 970                 975
Thr Ile Asp Val Pro Trp Asn Val Pro Glu Lys Ala His Leu Leu
                980                 985                 990

Ser Leu Val Asp Val Met Gln Arg Glu Gly Gly Pro Ser Gln Ile Gly
        995                 1000                1005

Asp Ala Leu Gly Phe Ala Val Arg Tyr Leu Thr Ser Glu Met His
    1010                1015                1020

Gly Ala Arg Pro Gly Ala Ser Lys Ala Val Val Ile Leu Val Thr
    1025                1030                1035

Asp Val Ser Val Asp Ser Val Asp Ala Ala Asp Ala Ala Arg
    1040                1045                1050

Ser Asn Arg Val Thr Val Phe Pro Ile Gly Ile Gly Asp Arg Tyr
    1055                1060                1065

Asp Ala Ala Gln Leu Arg Ile Leu Ala Gly Pro Ala Gly Asp Ser
    1070                1075                1080

Asn Val Val Lys Leu Gln Arg Ile Glu Asp Leu Pro Thr Met Val
    1085                1090                1095

Thr Leu Gly Asn Ser Phe Leu His Lys Leu Cys Ser Gly Phe Val
    1100                1105                1110

Arg Ile Cys Met Asp Glu Asp Gly Asn Glu Lys Arg Pro Gly Asp
    1115                1120                1125

Val Trp Thr Leu Pro Asp Gln Cys His Thr Val Thr Cys Gln Pro
    1130                1135                1140

Asp Gly Gln Thr Leu Leu Lys Ser His Arg Val Asn Cys Asp Arg
    1145                1150                1155

Gly Leu Arg Pro Ser Cys Pro Asn Ser Gln Ser Pro Val Lys Val
    1160                1165                1170

Glu Glu Thr Cys Gly Cys Arg Trp Thr Cys Pro Cys Val Cys Thr
    1175                1180                1185

Gly Ser Ser Thr Arg His Ile Val Thr Phe Asp Gly Gln Asn Phe
    1190                1195                1200

Lys Leu Thr Gly Ser Cys Ser Tyr Val Leu Phe Gln Asn Lys Glu
    1205                1210                1215

Gln Asp Leu Glu Val Ile Leu His Asn Gly Ala Cys Ser Pro Gly
    1220                1225                1230

Ala Arg Gln Gly Cys Met Lys Ser Ile Glu Val Lys His Ser Ala
    1235                1240                1245

Leu Ser Val Glu Leu His Ser Asp Met Glu Val Thr Val Asn Gly
    1250                1255                1260

Arg Leu Val Ser Val Pro Tyr Val Gly Gly Asn Met Glu Val Asn
    1265                1270                1275

Val Tyr Gly Ala Ile Met His Glu Val Arg Phe Asn His Leu Gly
    1280                1285                1290

His Ile Phe Thr Phe Thr Pro Gln Asn Asn Glu Phe Gln Leu Gln
    1295                1300                1305

Leu Ser Pro Lys Thr Phe Ala Ser Lys Thr Tyr Gly Leu Cys Gly
    1310                1315                1320

Ile Cys Asp Glu Asn Gly Ala Asn Asp Phe Met Leu Arg Asp Gly
    1325                1330                1335

Thr Val Thr Thr Asp Trp Lys Thr Leu Val Gln Glu Trp Thr Val
    1340                1345                1350

Gln Arg Pro Gly Gln Thr Cys Gln Pro Ile Leu Glu Glu Cys
    1355                1360                1365
```

-continued

```
Leu Val Pro Asp Ser Ser His Cys Gln Val Leu Leu Leu Pro Leu
    1370            1375                    1380

Phe Ala Glu Cys His Lys Val Leu Ala Pro Ala Thr Phe Tyr Ala
    1385            1390                    1395

Ile Cys Gln Gln Asp Ser Cys His Gln Glu Gln Val Cys Glu Val
    1400            1405                    1410

Ile Ala Ser Tyr Ala His Leu Cys Arg Thr Asn Gly Val Cys Val
    1415            1420                    1425

Asp Trp Arg Thr Pro Asp Phe Cys Ala Met Ser Cys Pro Pro Ser
    1430            1435                    1440

Leu Val Tyr Asn His Cys Glu His Gly Cys Pro Arg His Cys Asp
    1445            1450                    1455

Gly Asn Val Ser Ser Cys Gly Asp His Pro Ser Glu Gly Cys Phe
    1460            1465                    1470

Cys Pro Pro Asp Lys Val Met Leu Glu Gly Ser Cys Val Pro Glu
    1475            1480                    1485

Glu Ala Cys Thr Gln Cys Ile Gly Glu Asp Gly Val Gln His Gln
    1490            1495                    1500

Phe Leu Glu Ala Trp Val Pro Asp His Gln Pro Cys Gln Ile Cys
    1505            1510                    1515

Thr Cys Leu Ser Gly Arg Lys Val Asn Cys Thr Thr Gln Pro Cys
    1520            1525                    1530

Pro Xaa Ala Lys Ala Pro Thr Cys Gly Leu Cys Glu Val Ala Arg
    1535            1540                    1545

Leu Arg Gln Asn Ala Asp Gln Cys Cys Pro Glu Tyr Glu Cys Val
    1550            1555                    1560

Cys Asp Pro Val Ser Cys Asp Leu Pro Pro Val Pro His Cys Glu
    1565            1570                    1575

Arg Gly Leu Gln Pro Thr Leu Thr Asn Pro Gly Glu Cys Arg Pro
    1580            1585                    1590

Asn Phe Thr Cys Ala Cys Arg Lys Glu Glu Cys Lys Arg Val Ser
    1595            1600                    1605

Pro Pro Ser Cys Pro Pro His Arg Leu Pro Thr Leu Arg Lys Thr
    1610            1615                    1620

Gln Cys Cys Asp Glu Tyr Glu Cys Ala Cys Asn Cys Val Asn Ser
    1625            1630                    1635

Thr Val Ser Cys Pro Leu Gly Tyr Leu Ala Ser Thr Ala Thr Asn
    1640            1645                    1650

Asp Cys Gly Cys Thr Thr Thr Cys Leu Pro Asp Lys Val Cys
    1655            1660                    1665

Val His Arg Ser Thr Ile Tyr Pro Val Gly Gln Phe Trp Glu Glu
    1670            1675                    1680

Gly Cys Asp Val Cys Thr Cys Thr Asp Met Glu Asp Ala Val Met
    1685            1690                    1695

Gly Leu Arg Val Ala Gln Cys Ser Gln Lys Pro Cys Glu Asp Ser
    1700            1705                    1710

Cys Arg Ser Gly Phe Thr Tyr Val Leu His Glu Gly Glu Cys Cys
    1715            1720                    1725

Gly Arg Cys Leu Pro Ser Ala Cys Glu Val Val Thr Gly Ser Pro
    1730            1735                    1740

Arg Gly Asp Ser Gln Ser Ser Trp Lys Ser Val Gly Ser Gln Trp
    1745            1750                    1755
```

```
Ala Ser Pro Glu Asn Pro Cys Leu Ile Asn Glu Cys Val Arg Val
    1760            1765            1770

Lys Glu Glu Val Phe Ile Gln Gln Arg Asn Val Ser Cys Pro Gln
    1775            1780            1785

Leu Glu Val Pro Val Cys Pro Ser Gly Phe Gln Leu Ser Cys Lys
    1790            1795            1800

Thr Ser Ala Cys Cys Pro Ser Cys Arg Cys Glu Arg Met Glu Ala
    1805            1810            1815

Cys Met Leu Asn Gly Thr Val Ile Gly Pro Gly Lys Thr Val Met
    1820            1825            1830

Ile Asp Val Cys Thr Thr Cys Arg Cys Met Val Gln Val Gly Val
    1835            1840            1845

Ile Ser Gly Phe Lys Leu Glu Cys Arg Lys Thr Thr Cys Asn Pro
    1850            1855            1860

Cys Pro Leu Gly Tyr Lys Glu Glu Asn Asn Thr Gly Glu Cys Cys
    1865            1870            1875

Gly Arg Cys Leu Pro Thr Ala Cys Thr Ile Gln Leu Arg Gly Gly
    1880            1885            1890

Gln Ile Met Thr Leu Lys Arg Asp Glu Thr Leu Gln Asp Gly Cys
    1895            1900            1905

Asp Thr His Phe Cys Lys Val Asn Glu Arg Gly Glu Tyr Phe Trp
    1910            1915            1920

Glu Lys Arg Val Thr Gly Cys Pro Pro Phe Asp Glu His Lys Cys
    1925            1930            1935

Leu Ala Glu Gly Gly Lys Ile Met Lys Ile Pro Gly Thr Cys Cys
    1940            1945            1950

Asp Thr Cys Glu Glu Pro Glu Cys Asn Asp Ile Thr Ala Arg Leu
    1955            1960            1965

Gln Tyr Val Lys Val Gly Ser Cys Lys Ser Glu Val Glu Val Asp
    1970            1975            1980

Ile His Tyr Cys Gln Gly Lys Cys Ala Ser Lys Ala Met Tyr Ser
    1985            1990            1995

Ile Asp Ile Asn Asp Val Gln Asp Gln Cys Ser Cys Cys Ser Pro
    2000            2005            2010

Thr Arg Thr Glu Pro Met Gln Val Ala Leu His Cys Thr Asn Gly
    2015            2020            2025

Ser Val Val Tyr His Glu Val Leu Asn Ala Met Glu Cys Lys Cys
    2030            2035            2040

Ser Pro Arg Lys Cys Ser Lys
    2045            2050

<210> SEQ ID NO 12
<211> LENGTH: 1444
<212> TYPE: PRT
<213> ORGANISM: Artificial Sequence
<220> FEATURE:
<223> OTHER INFORMATION: single chain FVIII

<400> SEQUENCE: 12

Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
                20                  25                  30

Arg Val Pro Lys Ser Phe Pro Phe Asn Thr Ser Val Val Tyr Lys Lys
            35                  40                  45
```

Thr Leu Phe Val Glu Phe Thr Asp His Leu Phe Asn Ile Ala Lys Pro
50                      55                      60

Arg Pro Pro Trp Met Gly Leu Leu Gly Pro Thr Ile Gln Ala Glu Val
65                  70                      75                      80

Tyr Asp Thr Val Val Ile Thr Leu Lys Asn Met Ala Ser His Pro Val
                    85                      90                      95

Ser Leu His Ala Val Gly Val Ser Tyr Trp Lys Ala Ser Glu Gly Ala
                100                     105                     110

Glu Tyr Asp Asp Gln Thr Ser Gln Arg Glu Lys Glu Asp Asp Lys Val
            115                     120                     125

Phe Pro Gly Gly Ser His Thr Tyr Val Trp Gln Val Leu Lys Glu Asn
130                     135                     140

Gly Pro Met Ala Ser Asp Pro Leu Cys Leu Thr Tyr Ser Tyr Leu Ser
145                     150                     155                     160

His Val Asp Leu Val Lys Asp Leu Asn Ser Gly Leu Ile Gly Ala Leu
                165                     170                     175

Leu Val Cys Arg Glu Gly Ser Leu Ala Lys Glu Lys Thr Gln Thr Leu
            180                     185                     190

His Lys Phe Ile Leu Leu Phe Ala Val Phe Asp Glu Gly Lys Ser Trp
        195                     200                     205

His Ser Glu Thr Lys Asn Ser Leu Met Gln Asp Arg Asp Ala Ala Ser
        210                     215                     220

Ala Arg Ala Trp Pro Lys Met His Thr Val Asn Gly Tyr Val Asn Arg
225                     230                     235                     240

Ser Leu Pro Gly Leu Ile Gly Cys His Arg Lys Ser Val Tyr Trp His
                245                     250                     255

Val Ile Gly Met Gly Thr Thr Pro Glu Val His Ser Ile Phe Leu Glu
            260                     265                     270

Gly His Thr Phe Leu Val Arg Asn His Arg Gln Ala Ser Leu Glu Ile
        275                     280                     285

Ser Pro Ile Thr Phe Leu Thr Ala Gln Thr Leu Leu Met Asp Leu Gly
        290                     295                     300

Gln Phe Leu Leu Phe Cys His Ile Ser Ser His Gln His Asp Gly Met
305                     310                     315                     320

Glu Ala Tyr Val Lys Val Asp Ser Cys Pro Glu Glu Pro Gln Leu Arg
                325                     330                     335

Met Lys Asn Asn Glu Glu Ala Glu Asp Tyr Asp Asp Asp Leu Thr Asp
            340                     345                     350

Ser Glu Met Asp Val Val Arg Phe Asp Asp Asp Asn Ser Pro Ser Phe
        355                     360                     365

Ile Gln Ile Arg Ser Val Ala Lys Lys His Pro Lys Thr Trp Val His
370                     375                     380

Tyr Ile Ala Ala Glu Glu Asp Trp Asp Tyr Ala Pro Leu Val Leu
385                     390                     395                     400

Ala Pro Asp Asp Arg Ser Tyr Lys Ser Gln Tyr Leu Asn Asn Gly Pro
            405                     410                     415

Gln Arg Ile Gly Arg Lys Tyr Lys Lys Val Arg Phe Met Ala Tyr Thr
        420                     425                     430

Asp Glu Thr Phe Lys Thr Arg Glu Ala Ile Gln His Glu Ser Gly Ile
            435                     440                     445

Leu Gly Pro Leu Leu Tyr Gly Glu Val Gly Asp Thr Leu Leu Ile Ile
450                     455                     460

Phe Lys Asn Gln Ala Ser Arg Pro Tyr Asn Ile Tyr Pro His Gly Ile

-continued

```
           465                 470                 475                 480
       Thr Asp Val Arg Pro Leu Tyr Ser Arg Arg Leu Pro Lys Gly Val Lys
                       485                 490                 495
       His Leu Lys Asp Phe Pro Ile Leu Pro Gly Glu Ile Phe Lys Tyr Lys
                       500                 505                 510
       Trp Thr Val Thr Val Glu Asp Gly Pro Thr Lys Ser Asp Pro Arg Cys
                       515                 520                 525
       Leu Thr Arg Tyr Tyr Ser Ser Phe Val Asn Met Glu Arg Asp Leu Ala
                       530                 535                 540
       Ser Gly Leu Ile Gly Pro Leu Leu Ile Cys Tyr Lys Glu Ser Val Asp
       545                 550                 555                 560
       Gln Arg Gly Asn Gln Ile Met Ser Asp Lys Arg Asn Val Ile Leu Phe
                       565                 570                 575
       Ser Val Phe Asp Glu Asn Arg Ser Trp Tyr Leu Thr Glu Asn Ile Gln
                       580                 585                 590
       Arg Phe Leu Pro Asn Pro Ala Gly Val Gln Leu Glu Asp Pro Glu Phe
                       595                 600                 605
       Gln Ala Ser Asn Ile Met His Ser Ile Asn Gly Tyr Val Phe Asp Ser
                       610                 615                 620
       Leu Gln Leu Ser Val Cys Leu His Glu Val Ala Tyr Trp Tyr Ile Leu
       625                 630                 635                 640
       Ser Ile Gly Ala Gln Thr Asp Phe Leu Ser Val Phe Phe Ser Gly Tyr
                       645                 650                 655
       Thr Phe Lys His Lys Met Val Tyr Glu Asp Thr Leu Thr Leu Phe Pro
                       660                 665                 670
       Phe Ser Gly Glu Thr Val Phe Met Ser Met Glu Asn Pro Gly Leu Trp
                       675                 680                 685
       Ile Leu Gly Cys His Asn Ser Asp Phe Arg Asn Arg Gly Met Thr Ala
                       690                 695                 700
       Leu Leu Lys Val Ser Ser Cys Asp Lys Asn Thr Gly Asp Tyr Tyr Glu
       705                 710                 715                 720
       Asp Ser Tyr Glu Asp Ile Ser Ala Tyr Leu Leu Ser Lys Asn Asn Ala
                       725                 730                 735
       Ile Glu Pro Arg Ser Phe Ser Gln Asn Ser Arg His Pro Ser Thr Arg
                       740                 745                 750
       Gln Lys Gln Phe Asn Ala Thr Thr Ile Pro Glu Asn Thr Thr Leu Gln
                       755                 760                 765
       Ser Asp Gln Glu Glu Ile Asp Tyr Asp Thr Ile Ser Val Glu Met
       770                 775                 780
       Lys Lys Glu Asp Phe Asp Ile Tyr Asp Glu Asp Glu Asn Gln Ser Pro
       785                 790                 795                 800
       Arg Ser Phe Gln Lys Lys Thr Arg His Tyr Phe Ile Ala Ala Val Glu
                       805                 810                 815
       Arg Leu Trp Asp Tyr Gly Met Ser Ser Ser Pro His Val Leu Arg Asn
                       820                 825                 830
       Arg Ala Gln Ser Gly Ser Val Pro Gln Phe Lys Lys Val Val Phe Gln
                       835                 840                 845
       Glu Phe Thr Asp Gly Ser Phe Thr Gln Pro Leu Tyr Arg Gly Glu Leu
                       850                 855                 860
       Asn Glu His Leu Gly Leu Leu Gly Pro Tyr Ile Arg Ala Glu Val Glu
       865                 870                 875                 880
       Asp Asn Ile Met Val Thr Phe Arg Asn Gln Ala Ser Arg Pro Tyr Ser
                       885                 890                 895
```

-continued

```
Phe Tyr Ser Ser Leu Ile Ser Tyr Glu Glu Asp Gln Arg Gln Gly Ala
            900                 905                 910

Glu Pro Arg Lys Asn Phe Val Lys Pro Asn Glu Thr Lys Thr Tyr Phe
            915                 920                 925

Trp Lys Val Gln His His Met Ala Pro Thr Lys Asp Glu Phe Asp Cys
            930                 935                 940

Lys Ala Trp Ala Tyr Phe Ser Asp Val Asp Leu Glu Lys Asp Val His
945                 950                 955                 960

Ser Gly Leu Ile Gly Pro Leu Leu Val Cys His Thr Asn Thr Leu Asn
                965                 970                 975

Pro Ala His Gly Arg Gln Val Thr Val Gln Glu Phe Ala Leu Phe Phe
            980                 985                 990

Thr Ile Phe Asp Glu Thr Lys Ser Trp Tyr Phe Thr Glu Asn Met Glu
            995                 1000                1005

Arg Asn Cys Arg Ala Pro Cys Asn Ile Gln Met Glu Asp Pro Thr
    1010                1015                1020

Phe Lys Glu Asn Tyr Arg Phe His Ala Ile Asn Gly Tyr Ile Met
    1025                1030                1035

Asp Thr Leu Pro Gly Leu Val Met Ala Gln Asp Gln Arg Ile Arg
    1040                1045                1050

Trp Tyr Leu Leu Ser Met Gly Ser Asn Glu Asn Ile His Ser Ile
    1055                1060                1065

His Phe Ser Gly His Val Phe Thr Val Arg Lys Lys Glu Glu Tyr
    1070                1075                1080

Lys Met Ala Leu Tyr Asn Leu Tyr Pro Gly Val Phe Glu Thr Val
    1085                1090                1095

Glu Met Leu Pro Ser Lys Ala Gly Ile Trp Arg Val Glu Cys Leu
    1100                1105                1110

Ile Gly Glu His Leu His Ala Gly Met Ser Thr Leu Phe Leu Val
    1115                1120                1125

Tyr Ser Asn Lys Cys Gln Thr Pro Leu Gly Met Ala Ser Gly His
    1130                1135                1140

Ile Arg Asp Phe Gln Ile Thr Ala Ser Gly Gln Tyr Gly Gln Trp
    1145                1150                1155

Ala Pro Lys Leu Ala Arg Leu His Tyr Ser Gly Ser Ile Asn Ala
    1160                1165                1170

Trp Ser Thr Lys Glu Pro Phe Ser Trp Ile Lys Val Asp Leu Leu
    1175                1180                1185

Ala Pro Met Ile Ile His Gly Ile Lys Thr Gln Gly Ala Arg Gln
    1190                1195                1200

Lys Phe Ser Ser Leu Tyr Ile Ser Gln Phe Ile Ile Met Tyr Ser
    1205                1210                1215

Leu Asp Gly Lys Lys Trp Gln Thr Tyr Arg Gly Asn Ser Thr Gly
    1220                1225                1230

Thr Leu Met Val Phe Phe Gly Asn Val Asp Ser Ser Gly Ile Lys
    1235                1240                1245

His Asn Ile Phe Asn Pro Pro Ile Ile Ala Arg Tyr Ile Arg Leu
    1250                1255                1260

His Pro Thr His Tyr Ser Ile Arg Ser Thr Leu Arg Met Glu Leu
    1265                1270                1275

Met Gly Cys Asp Leu Asn Ser Cys Ser Met Pro Leu Gly Met Glu
    1280                1285                1290
```

```
Ser Lys Ala Ile Ser Asp Ala Gln Ile Thr Ala Ser Ser Tyr Phe
    1295            1300            1305

Thr Asn Met Phe Ala Thr Trp Ser Pro Ser Lys Ala Arg Leu His
    1310            1315            1320

Leu Gln Gly Arg Ser Asn Ala Trp Arg Pro Gln Val Asn Asn Pro
    1325            1330            1335

Lys Glu Trp Leu Gln Val Asp Phe Gln Lys Thr Met Lys Val Thr
    1340            1345            1350

Gly Val Thr Thr Gln Gly Val Lys Ser Leu Leu Thr Ser Met Tyr
    1355            1360            1365

Val Lys Glu Phe Leu Ile Ser Ser Ser Gln Asp Gly His Gln Trp
    1370            1375            1380

Thr Leu Phe Phe Gln Asn Gly Lys Val Lys Val Phe Gln Gly Asn
    1385            1390            1395

Gln Asp Ser Phe Thr Pro Val Val Asn Ser Leu Asp Pro Pro Leu
    1400            1405            1410

Leu Thr Arg Tyr Leu Arg Ile His Pro Gln Ser Trp Val His Gln
    1415            1420            1425

Ile Ala Leu Arg Met Glu Val Leu Gly Cys Glu Ala Gln Asp Leu
    1430            1435            1440

Tyr
```

MODIFIED VON WILLEBRAND FACTOR HAVING IMPROVED HALF-LIFE

This application is the United States national stage entry under 35 U.S.C. § 371 of International Application No. PCT/EP2016/054647, filed on Mar. 4, 2016 and published as WO 2016/142288A1, which claims priority to European Patent Application No. 15158065.1, filed on Mar. 6, 2015. The contents of these applications are each incorporated herein by reference in their entirety.

FIELD OF THE INVENTION

The present invention relates to products and methods for improving treatment of blood coagulation disorders.

BACKGROUND OF THE INVENTION

There are various bleeding disorders caused by deficiencies of blood coagulation factors. The most common disorders are hemophilia A and B, resulting from deficiencies of blood coagulation factor VIII (FVIII) and IX, respectively. Another known bleeding disorder is von Willebrand's disease (VWD).

In plasma FVIII exists mostly as a noncovalent complex with von Willebrand factor (VWF), and its coagulant function is to accelerate factor IXa dependent conversion of factor X to Xa.

Classic hemophilia or hemophilia A is an inherited bleeding disorder. It results from a chromosome X-linked deficiency of blood coagulation FVIII, and affects almost exclusively males with an incidence of between one and two individuals per 10,000. The X-chromosome defect is transmitted by female carriers who are not themselves hemophiliacs. The clinical manifestation of hemophilia A is an increased bleeding tendency.

In severe hemophilia A patients undergoing prophylactic treatment FVIII has to be administered intravenously (i.v.) about 3 times per week due to the short plasma half-life of FVIII of about 12 to 14 hours. Each i.v. administration is cumbersome, associated with pain and entails the risk of an infection especially as this is mostly done at home by the patients themselves or by the parents of children being diagnosed for hemophilia A.

It would thus be highly desirable to increase the half-life of FVIII so that pharmaceutical compositions containing FVIII which have to be administered less frequently.

Several attempts have been made to prolong the half-life of non-activated FVIII either by reducing its interaction with cellular receptors (WO 03/093313 A2, WO 02/060951 A2), by covalently attaching polymers to FVIII (WO 94/15625, WO 97/11957 and U.S. Pat. No. 4,970,300), by encapsulation of FVIII (WO 99/55306), by introduction of novel metal binding sites (WO 97/03193), by covalently attaching the A2 domain to the A3 domain either by peptidic (WO 97/40145 and WO 03/087355) or disulfide linkage (WO 02/103024A2) or by covalently attaching the A1 domain to the A2 domain (WO2006/108590).

Another approach to enhance the functional half-life of FVIII or VWF is by PEGylation of FVIII (WO 2007/126808, WO 2006/053299, WO 2004/075923) or by PEGylation of VWF (WO 2006/071801) which pegylated VWF by having an increased half-life would indirectly also enhance the half-life of FVIII present in plasma. Also fusion proteins of FVIII have been described (WO 2004/101740, WO2008/077616 and WO 2009/156137).

VWF, which is missing, functionally defect or only available in reduced quantity in different forms of von Willebrand disease (VWD), is a multimeric adhesive glycoprotein present in the plasma of mammals, which has multiple physiological functions. During primary hemostasis VWF acts as a mediator between specific receptors on the platelet surface and components of the extracellular matrix such as collagen. Moreover, VWF serves as a carrier and stabilizing protein for procoagulant FVIII. VWF is synthesized in endothelial cells and megakaryocytes as a 2813 amino acid precursor molecule. The amino acid sequence and the cDNA sequence of wild-type VWF are disclosed in Collins et al. 1987, Proc Natl. Acad. Sci. USA 84:4393-4397. The precursor polypeptide, pre-pro-VWF, consists of a 22-residue signal peptide, a 741-residue pro-peptide and the 2050-residue polypeptide found in mature plasma VWF (Fischer et al., FEBS Lett. 351: 345-348, 1994). After cleavage of the signal peptide in the endoplasmatic reticulum a C-terminal disulfide bridge is formed between two monomers of VWF. During further transport through the secretory pathway 13 N-linked and 10 O-linked carbohydrate side chains are added (Canis et al. (2010) Journal of Thrombosis and Haemostasis, 8: 137-145; Canis et al. (2012) The Biochemical Journal, 447: 217-228). More important, VWF dimers are multimerized via N-terminal disulfide bridges and the propeptide of 741 amino acids length is cleaved off by the enzyme PACE/furin in the late Golgi apparatus. The propeptide as well as the high-molecular-weight multimers of VWF (VWF-HMWM) are stored in the Weibel-Palade bodies of endothelial cells or in the α-granules of platelets.

Once secreted into plasma the protease ADAMTS13 cleaves VWF within the A1 domain of VWF. Plasma VWF therefore consists of a whole range of multimers ranging from single dimers of 500 kDa to multimers consisting of up to more than 20 dimers of a molecular weight of over 10,000 kDa. The VWF-HMWM hereby having the strongest hemostatic activity, which can be measured in ristocetin cofactor activity (VWF:RCo). The higher the ratio of VWF:RCo/VWF antigen, the higher the relative amount of high molecular weight multimers.

Defects in VWF are causal to von Willebrand disease (VWD), which is characterized by a more or less pronounced bleeding phenotype. VWD type 3 is the most severe form in which VWF is completely missing, VWD type 1 relates to a quantitative loss of VWF and its phenotype can be very mild. VWD type 2 relates to qualitative defects of VWF and can be as severe as VWD type 3. VWD type 2 has many sub forms some of them being associated with the loss or the decrease of high molecular weight multimers. Von VWD type 2a is characterized by a loss of both intermediate and large multimers. VWD type 2B is characterized by a loss of highest-molecular-weight multimers.

VWD is the most frequent inherited bleeding disorder in humans and can be treated by replacement therapy with concentrates containing VWF of plasmatic or recombinant origin.

In plasma FVIII binds with high affinity to VWF, which protects it from premature catabolism and thus, plays in addition to its role in primary hemostasis a crucial role to regulate plasma levels of FVIII and as a consequence is also a central factor to control secondary hemostasis. The half-life of non-activated FVIII bound to VWF is about 12 to 14 hours in plasma. In von Willebrand disease type 3, where no or almost no VWF is present, the half-life of FVIII is only about 6 hours, leading to symptoms of mild to moderate hemophilia A in such patients due to decreased concentrations of FVIII. The stabilizing effect of VWF on FVIII has also been used to aid recombinant expression of FVIII in CHO cells (Kaufman et al. 1989, Mol Cell Biol).

There is a need for products and methods for increasing the half-life of VWF, FVIII or both factors.

SUMMARY OF THE INVENTION

In a separate invention, it had been found that VWF monomers strongly bind to calcium-type lectin domain family 10 member A (CLEC10A), a receptor protein present on macrophages. In particular, it could be shown that CLEC10A plays a crucial role in VWF clearance. In the present invention, it was further found that the O-linked glycan site 2298 present on VWF interacts with CLEC10A. The present invention therefore provides modified VWF molecules lacking the O-linked glycosylation at position 2298 to prolong the half-life of the VWF molecules in vivo.

The present invention therefore relates to the subject matter defined in items [1] to [21]:

[1] A von Willebrand factor (VWF) molecule capable of binding to Factor VIII, comprising a C1 domain which lacks an O-glycosylation site at amino acid position 2298. Preferably the VWF molecule is not murine. More preferably, the VWF molecule is human.

[2] The VWF molecule of item [1], wherein the O-glycosylation site at position 2298 present in native VWF has been inactivated by deleting or substituting one or more amino acids at positions 2292 to 2303 of the VWF amino acid sequence.

[3] The VWF molecule of item [2], wherein threonine at position 2298 has been deleted or substituted with an amino acid other than threonine and serine.

[4] The VWF molecule of item [3], wherein said amino acid other than threonine and serine is selected from the group consisting of glycine, alanine, arginine, asparagine, aspartic acid, cysteine, glutamic acid, glutamine, histidine, isoleucine, leucine, lysine, methionine, phenylalanine, proline, tryptophan, tyrosine, and valine.

[5] The VWF molecule of any one of the preceding items, comprising an amino acid sequence as shown in SEQ ID NO:10 or 11.

[6] The VWF molecule of item [2], wherein proline at one of the positions 2295, 2297 and 2302 has been deleted or substituted with a different amino acid.

[7] The VWF molecule of any one of the preceding items, having a reduced in vivo clearance than native plasma-derived VWF.

[8] A VWF C1 domain comprising the O-glycosylation site at amino acid position 2298, linked to a half-life extending moiety, preferably fused to human albumin.

[9] The VWF molecule of any one of the preceding items, which is capable of increasing the half-life of Factor VIII co-administered with said VWF molecule, as compared to the half-life of the Factor VIII co-administered with native plasma-derived VWF.

[10] The VWF molecule as defined in any one of the preceding items for use in the treatment of a blood coagulation disorder.

[11] The VWF molecule for use according to item [10], wherein said blood coagulation disorder is hemophilia A or von Willebrand disease.

[12] The VWF molecule for use according to item [10] or [11], wherein said treatment further comprises administering a Factor VIII molecule.

[13] The VWF molecule for use according to item [12], wherein said VWF molecule and said Factor VIII molecule are administered separately.

[14] A pharmaceutical composition comprising the VWF molecule of any one of items [1] to [9].

[15] A pharmaceutical kit comprising (i) the VWF molecule of any one of items [1] to [9] and (ii) a Factor VIII molecule.

[16] The pharmaceutical kit of item [15], wherein said VWF molecule and said Factor VIII molecule are contained in separate compositions.

[17] A pharmaceutical kit comprising (i) the VWF molecule of any one of items [1] to [9] and (ii) a Factor VIII molecule, for simultaneous, separate or sequential use in the treatment of a blood coagulation disorder.

[18] The use of the VWF molecule of any one of items [1] to [9] for increasing the half-life of Factor VIII in vivo.

[19] A VWF molecule as defined in any one of items [1] to [9] for use in prolonging the half-life of Factor VIII in a therapeutic treatment.

[20] A method of increasing the half-life Factor VIII in vivo, comprising administering to a subject an effective amount of the VWF molecule of any one of items [1] to [9].

[21] A method of treating a blood coagulation disorder, comprising administering to a patient in need thereof an effective amount of the VWF molecule of any one of items [1] to [9].

Core 2 glycan (A), core 1 glycan carrying one NeuGc residue (B) and core 2 glycan elongated with the disaccharide GlcNAcβ1,3Gal (C) were identified as predominant O-glycan structures present in eluate fractions. After incubation of tryptic VWF fragments with soluble CLEC10A, washing and elution of bound VWF peptides, MALDI-TOF-MS analyses of free glycans revealed a significant enrichment of glycan structure A (concentration factor of >40), B (factor 9) and C (factor 7), when compared with the starting material prior to incubation with CLEC10A. The three displayed O-glycans represented approximately 80% of all O-glycan structures detected (40% related to structure B whereas A and C accounted for 20% each).

DETAILED DESCRIPTION

In a first aspect, the present invention pertains to a modified von Willebrand factor (VWF) molecule capable of binding to Factor VIII, comprising a C1 domain which lacks an O-glycosylation site at amino acid position 2298.

VWF

The term "von Willebrand factor" (VWF) as used herein includes naturally occurring (native) VWF, but also variants thereof, e.g. fragments, fusion proteins or conjugates, or sequence variants where one or more residues have been inserted, deleted or substituted, retaining the biological activity of naturally occurring VWF. The biological activity is retained in the sense of the invention if the VWF variant retains at least 10%, preferably at least 25%, more preferably at least 50%, most preferably at least 75% of at least one of the biological activities of wild-type VWF. The biological activity of wild-type VWF and variants thereof can be determined by the artisan using methods for ristocetin co-factor activity (Federici A B et al. 2004. Haematologica 89:77-85), binding of VWF to GP Ibα of the platelet glycoprotein complex Ib-V-IX (Sucker et al. 2006. Clin Appl Thromb Hemost. 12:305-310), or a collagen binding assay (Kallas & Talpsep. 2001. Annals of Hematology 80:466-471)), or a Factor VIII binding assay (Veyradier et al. (2011) Haemophilia, vol. 17, pp 944-951).

The gene encoding human native VWF is transcribed into a 9 kb mRNA which is translated into a pre-propolypeptide of 2813 amino acids with an estimated molecular weight of 310,000 Da. The pre-propolypeptide contains a 22 amino acids signal peptide, a 741 amino acid pro-polypeptide (amino acids 23-763 of SEQ ID NO:2) and the mature subunit (amino acids 764-2813 of SEQ ID NO:2). Cleavage of the 741 amino acids propolypeptide from the N-terminus results in mature VWF consisting of 2050 amino acids. The amino acid sequence of the human native VWF pre-propolypeptide is shown in SEQ ID NO:2. Unless indicated otherwise, the amino acid numbering of VWF residues in this application refers to SEQ ID NO:2, even if the VWF molecule does not comprise all residues of SEQ ID NO:2. The term "VWF" as used herein refers to the mature form of VWF unless indicated otherwise.

Figure 1:
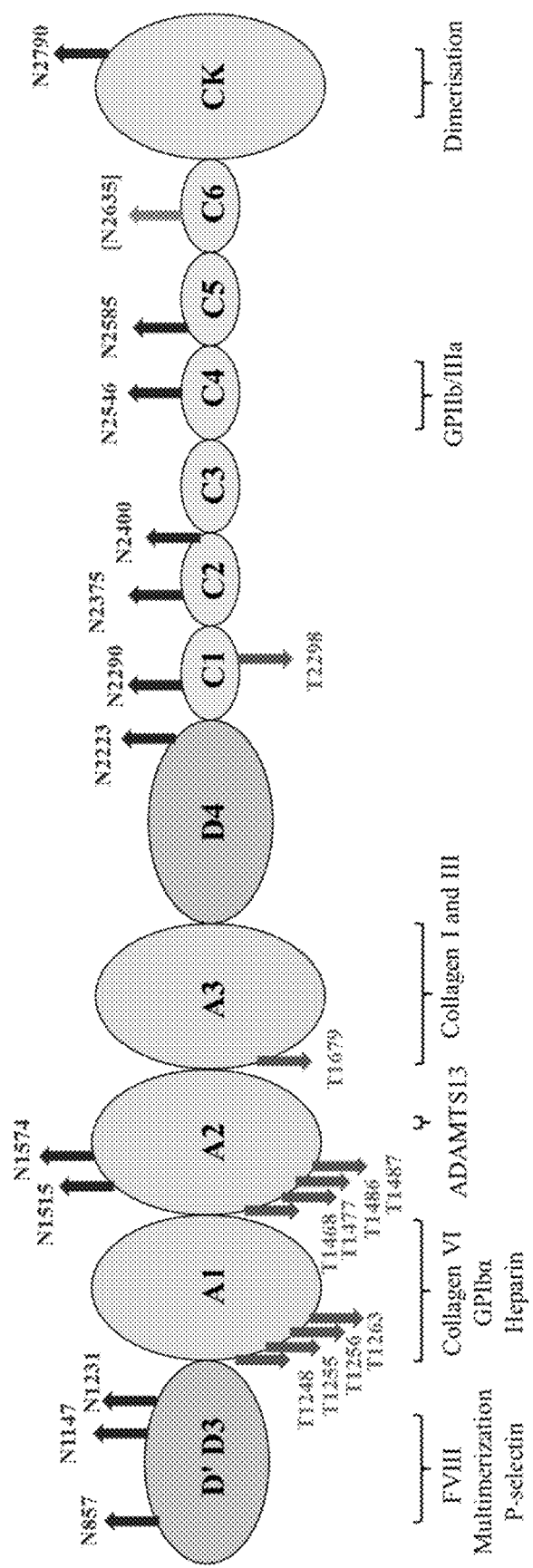
FIG. 1: Domain structures, functional binding sites and glycan positions of the mature VWF monomer The protein structure of the VWF monomer reveals areas of internal homology termed A, C and D domains. VWF interacts with a large number of ligands with a range of biological functions. Each mature VWF monomer contains 13 N-linked (upward arrows) and 10 O-linked (downward arrows) glycosylation sites distributed as shown. The sequence number of the amino acid involved in a glycosidic bond is given. The revised annotation of the VWF mature subunit structure was adapted and modified from Zhou et al. (2012) Blood 120(2): 449-458.

The propolypeptide of native VWF comprises multiple domains. Different domain annotations can be found in the literature (see, e.g. Zhou et al. (2012) Blood 120(2): 449-458). The following domain annotation of native pre-propolypeptide of VWF is applied in this application (see also FIG. 1):

D1-D2-D'-D3-A1-A2-A3-D4-C1-C2-C3-C4-C5-C6-CK

With reference to SEQ ID NO:2, the D' domain consists of amino acids 764-865; the D3 domain consists of amino acids 866-1242; and the C1 domain consists of amino acids 2255-2328.

A "modified" VWF molecule has an amino acid sequence that differs from the amino acid sequence of mature human native VWF (amino acids 764-2813 of the amino acid shown in SEQ ID NO:2.

The modified VWF molecule of the present invention comprises a C1 domain of VWF lacking an O-glycosylation site at amino acid position 2298. The amino acid sequence of the C1 domain comprised in the modified VWF molecule of the invention has a sequence identity to amino acids 2255-2328 of SEQ ID NO:2 of at least 80%, preferably of at least 85%, more preferably of at least 90%, most preferably of at least 95%.

In preferred embodiments, one, two or three (but not more) amino acids that are present in amino acids 2255-2328 of SEQ ID NO:2 are deleted and/or substituted in the C1 domain comprised in the modified VWF molecule of the present invention.

In a first embodiment, the modified VWF molecule of the present invention comprises amino acids 2255-2328 of SEQ ID NO:2 except for three amino acids, wherein each of said three amino acids has been deleted or substituted with an amino acid not present at the respective position within SEQ ID NO:2. That is, the amino acid sequence of the C1 domain of the modified VWF molecule of the invention differs from the amino acid sequence of the C1 domain of SEQ ID NO:2 in three (and not more) amino acids.

In a second embodiment, the modified VWF molecule of the present invention comprises amino acids 2255-2328 of SEQ ID NO:2 except for two amino acids, wherein each of said two amino acids has been deleted or substituted with an amino acid not present at the respective position within SEQ ID NO:2. That is, the amino acid sequence of the C1 domain of the modified VWF molecule of the invention differs from the amino acid sequence of the C1 domain of SEQ ID NO:2 in two (and not more) amino acids.

In a third embodiment, the modified VWF molecule of the present invention comprises amino acids 2255-2333 of SEQ ID NO:2 except for one amino acid, wherein said one amino acid has been deleted or substituted with an amino acid not present at the respective position within SEQ ID NO:2. That is, the amino acid sequence of the C1 domain of the modified VWF molecule of the invention differs from the amino acid sequence of the C1 domain of SEQ ID NO:2 in one (and not more) amino acid.

Preferably, the O-glycosylation site at position 2298 of the VWF amino acid sequence is inactivated by deleting the threonine at position 2298 or by substituting it with a different amino acid, preferably with an amino acid other than threonine and serine.

Accordingly, the invention provides in a further embodiment a modified VWF molecule comprising the amino acid sequence shown in SEQ ID NO:10. In preferred aspects, the VWF molecule of the present invention comprises the amino acid sequence shown in SEQ ID NO:10 wherein Xaa is absent;

the amino acid sequence shown in SEQ ID NO:10 wherein Xaa is glycine;

the amino acid sequence shown in SEQ ID NO:10 wherein Xaa is alanine;

the amino acid sequence shown in SEQ ID NO:10 wherein Xaa is arginine;

the amino acid sequence shown in SEQ ID NO:10 wherein Xaa is asparagine;

the amino acid sequence shown in SEQ ID NO:10 wherein Xaa is aspartic acid;

the amino acid sequence shown in SEQ ID NO:10 wherein Xaa is cysteine;

the amino acid sequence shown in SEQ ID NO:10 wherein Xaa is glutamic acid;

the amino acid sequence shown in SEQ ID NO:10 wherein Xaa is glutamine;

the amino acid sequence shown in SEQ ID NO:10 wherein Xaa is histidine;

the amino acid sequence shown in SEQ ID NO:10 wherein Xaa is isoleucine;

the amino acid sequence shown in SEQ ID NO:10 wherein Xaa is leucine;

the amino acid sequence shown in SEQ ID NO:10 wherein Xaa is lysine;

the amino acid sequence shown in SEQ ID NO:10 wherein Xaa is methionine;

the amino acid sequence shown in SEQ ID NO:10 wherein Xaa is phenylalanine;

the amino acid sequence shown in SEQ ID NO:10 wherein Xaa is proline;
the amino acid sequence shown in SEQ ID NO:10 wherein Xaa is tryptophan;
the amino acid sequence shown in SEQ ID NO:10 wherein Xaa is tyrosine; or
the amino acid sequence shown in SEQ ID NO:10 wherein Xaa is valine.

Typically, the modified VWF molecule of the present invention further comprises a D'D3 domain. Preferably, the modified VWF molecule comprises amino acids 764 to 1242 of SEQ ID NO:2, or an amino acid sequence that has a sequence identity of at least 90%, preferably of at least 95%, more preferably of at least 98% to an amino acid sequence consisting of amino acids 764 to 1242 of SEQ ID NO:2.

In a further embodiment, the modified VWF molecule of the present invention comprises or consists of an amino acid sequence as shown in SEQ ID NO:11. In preferred aspects, the VWF molecule of the present invention comprises or consists of
the amino acid sequence shown in SEQ ID NO:11 wherein Xaa is absent;
the amino acid sequence shown in SEQ ID NO:11 wherein Xaa is glycine;
the amino acid sequence shown in SEQ ID NO:11 wherein Xaa is alanine;
the amino acid sequence shown in SEQ ID NO:11 wherein Xaa is arginine;
the amino acid sequence shown in SEQ ID NO:11 wherein Xaa is asparagine;
the amino acid sequence shown in SEQ ID NO:11 wherein Xaa is aspartic acid;
the amino acid sequence shown in SEQ ID NO:11 wherein Xaa is cysteine;
the amino acid sequence shown in SEQ ID NO:11 wherein Xaa is glutamic acid;
the amino acid sequence shown in SEQ ID NO:11 wherein Xaa is glutamine;
the amino acid sequence shown in SEQ ID NO:11 wherein Xaa is histidine;
the amino acid sequence shown in SEQ ID NO:11 wherein Xaa is isoleucine;
the amino acid sequence shown in SEQ ID NO:11 wherein Xaa is leucine;
the amino acid sequence shown in SEQ ID NO:11 wherein Xaa is lysine;
the amino acid sequence shown in SEQ ID NO:11 wherein Xaa is methionine;
the amino acid sequence shown in SEQ ID NO:11 wherein Xaa is phenylalanine;
the amino acid sequence shown in SEQ ID NO:11 wherein Xaa is proline;
the amino acid sequence shown in SEQ ID NO:11 wherein Xaa is tryptophan;
the amino acid sequence shown in SEQ ID NO:11 wherein Xaa is tyrosine; or
the amino acid sequence shown in SEQ ID NO:11 wherein Xaa is valine.

Alternatively, the O-glycosylation site at position 2298 is inactivated by deleting or substituting one or more amino acids that are involved in the recognition of the glycosylation site by the glycosyltransferases. The putative glycosylation motif comprises amino acids 2292-2303 of VWF. In one embodiment, at least one proline at positions 2295, 2297 and/or 2302 is deleted or substituted with a different amino acid. Alternatively at least one threonine at positions 2292, 2293 and/or 2303 is deleted or substituted with a different amino acid.

The modified VWF molecule of the present invention is capable of binding to a Factor VIII molecule, and/or it comprises a D' domain and a D3 domain (e.g. the D' domain and the D3 domain of SEQ ID NO:3). Preferably, the modified VWF molecule is capable of binding to the mature form of the human native Factor VIII. In another embodiment, the modified VWF molecule is capable of binding to the single-chain Factor VIII molecule consisting of the amino acid sequence SEQ ID NO:12.

Binding of VWF to Factor VIII can be determined by using a commercially distributed ready-to-use ELISA kit (Asserachrom VWF:FVIIIB, Diagnostica Stago, Asnieres, France) based on the method description reported earlier (Veyradier et al. (2011) Haemophilia, vol. 17, pp 944-951). Samples are diluted with ready-to-use dilution buffers respectively defined by the supplier of the test kit. VWF present in the samples to be tested is captured by a rabbit anti-human VWF polyclonal antibody pre-coated on microtiter plates. Subsequently, endogenous FVIII potentially attendant is dissociated from VWF and eliminated. After adding recombinant FVIII that interacted with the captured VWF, a mouse monoclonal anti-human FVIII antibody coupled with peroxidase binds to attached FVIII and the subsequent substrate reaction stopped with 1 M sulfuric acid after a reaction time of 5 min is photometrically quantified at 450 nm. The test results are calculated by using the test kit related standard.

Alternatively, a flow cytometry/equilibrium binding assay can be utilized, for example, as described by Bendetowicz et al. (1998) Blood, vol 92, No 2: pp 529-538.

Factor VIII

The terms "Factor VIII" and "FVIII" are used synonymously herein. "FVIII" includes natural allelic variations of FVIII that may exist and occur from one individual to another. FVIII may be plasma-derived or recombinantly produced, using well known methods of production and purification. The degree and location of glycosylation, tyrosine sulfation and other post-translation modifications may vary, depending on the chosen host cell and its growth conditions.

The term FVIII includes FVIII analogues. The term "FVIII analogue" as used herein refers to a FVIII molecule (full-length or B-domain-truncated/deleted) wherein one or more amino acids have been substituted or deleted compared to the wild type amino acid sequence of FVIII (i.e. the sequence defined by UniProt identifier P00451) or, for B-domain truncated/deleted FVIII molecules, the corresponding part of that amino acid sequence. FVIII analogues do not occur in nature but are obtained by human manipulation. The Factor VIII molecules used according to the present invention may also be B-domain-truncated/deleted FVIII molecules wherein the remaining domains correspond to the sequences as set forth in amino acid numbers 1-740 and 1649-2332 of the FVIII wild type amino acid sequence. Other forms of B-domain deleted FVIII molecules have additionally a partial deletion in their a3 domain, which leads to single-chain FVIII molecules.

It follows that these FVIII molecules are recombinant molecules produced in transformed host cells, preferably of mammalian origin. However, the remaining domains in a B-domain deleted FVIII, (i.e. the three A-domains, the two C-domains and the a1, a2 and a3 regions) may differ slightly e.g. about 1%, 2%, 3%, 4% or 5% from the respective wild type amino acid sequence (amino acids 1-740 and 1649-2332).

The FVIII molecules used in accordance with the present invention may be two-chain FVIII molecules or single-chain FVIII molecules. The FVIII molecules included in the composition of the present invention may also be biologically active fragments of FVIII, i.e., FVIII wherein domain(s) other than the B-domain has/have been deleted or truncated, but wherein the FVIII molecule in the deleted/truncated form retains its ability to support the formation of a blood clot. FVIII activity can be assessed in vitro using techniques well known in the art. A preferred test for determining FVIII activity according to this invention is the chromogenic substrate assay or the one stage assay (see infra). Amino acid modifications (substitutions, deletions, etc.) may be introduced in the remaining domains, e.g., in order to modify the binding capacity of Factor VIII with various other components such as e.g. VWF), low density lipoprotein receptor-related protein (LPR), various receptors, other coagulation factors, cell surfaces, etc. or in order to introduce and/or abolish glycosylation sites, etc. Other mutations that do not abolish FVIII activity may also be accommodated in a FVIII molecule/analogue for use in a composition of the present invention.

FVIII analogues also include FVIII molecules, in which one or more of the amino acid residues of the parent polypeptide have been deleted or substituted with other amino acid residues, and/or wherein additional amino acid residues have been added to the parent FVIII polypeptide.

Furthermore, the Factor VIII molecules/analogues may comprise other modifications in e.g. the truncated B-domain and/or in one or more of the other domains of the molecules ("FVIII derivatives"). These other modifications may be in the form of various molecules conjugated to the Factor VIII molecule, such as e.g. polymeric compounds, peptidic compounds, fatty acid derived compounds, etc.

The term FVIII includes glycopegylated FVIII. In the present context, the term "glycopegylated FVIII" is intended to designate a Factor VIII molecule (including full length FVIII and B-domain truncated/deleted FVIII) wherein one or more PEG group(s) has/have been attached to the FVIII polypeptide via the polysaccharide sidechain(s) (glycan(s)) of the polypeptide.

The term FVIII includes FVIII molecules having protective groups or half-life extending moieties. The terms "protective groups"/"half-life extending moieties" is herein understood to refer to one or more chemical groups attached to one or more amino acid site chain functionalities such as —SH, —OH, —COOH, —CONH2, —NH2, or one or more N- and/or O-glycan structures and that can increase in vivo circulatory half-life of a number of therapeutic proteins/peptides when conjugated to these proteins/peptides. Examples of protective groups/half-life extending moieties include: Biocompatible fatty acids and derivatives thereof, Hydroxy Alkyl Starch (HAS) e.g. Hydroxy Ethyl Starch (HES), Poly (Glyx-Sery)n (Homo Amino acid Polymer (HAP)), Hyaluronic acid (HA), Heparosan polymers (HEP), Phosphorylcholine-based polymers (PC polymer), Fleximer® polymers (Mersana Therapeutics, MA, USA), Dextran, Poly-sialic acids (PSA), polyethylene glycol (PEG), an Fc domain, Transferrin, Albumin, Elastin like peptides, XTEN® polymers (Amunix, Calif., USA), Albumin binding peptides, a von Willebrand factor fragment (vWF fragment), a Carboxyl Terminal Peptide (CTP peptide, Prolor Biotech, IL), and any combination thereof (see, for example, McCormick, C. L., A. B. Lowe, and N. Ayres, Water-Soluble Polymers, in Encyclopedia of Polymer Science and Technology. 2002, John Wiley & Sons, Inc.). The manner of derivatization is not critical and can be elucidated from the above.

The FVIII molecules which can be used in accordance with this invention include fusion proteins comprising a FVIII amino acid sequence fused to a heterologous amino acid sequence, preferably a half-life extending amino acid sequence. Preferred fusion proteins are Fc fusion proteins and albumin fusion proteins. The term "Fc fusion protein" is herein meant to encompass FVIII fused to an Fc domain that can be derived from any antibody isotype. An IgG Fc domain will often be preferred due to the relatively long circulatory half-life of IgG antibodies. The Fc domain may furthermore be modified in order to modulate certain effector functions such as e.g. complement binding and/or binding to certain Fc receptors. Fusion of FVIII with an Fc domain, which has the capacity to bind to FcRn receptors, will generally result in a prolonged circulatory half-life of the fusion protein compared to the half-life of the wild type FVIII. It follows that a FVIII molecule for use in the present invention may also be a derivative of a FVIII analogue, such as, for example, a fusion protein of an FVIII analogue, a PEGylated or glycoPEGylated FVIII analogue, or a FVIII analogue conjugated to a heparosan polymer. The term "albumin fusion protein" is herein meant to encompass FVIII fused to an albumin amino acid sequence or a fragment or derivative thereof. The heterologous amino acid sequence may be fused to the N- or C-terminus of FVIII, or it may be inserted internally within the FVIII amino acid sequence. The heterologous amino acid sequence may be any "half life extending polypeptide" described in WO 2008/077616 A1, the disclosure of which is incorporated herein by reference.

Examples of FVIII molecules for use in compositions of the present invention comprise for instance the FVIII molecules described in WO 2010/045568, WO 2009/062100, WO 2010/014708, WO 2008/082669, WO 2007/126808, US 2010/0173831, US 2010/0173830, US 2010/0168391, US 2010/0113365, US 2010/0113364, WO 2003/031464, WO 2009/108806, WO 2010/102886, WO 2010/115866, WO 2011/101242, WO 2011/101284, WO 2011/101277, WO 2011/131510, WO 2012/007324, WO 2011/101267, WO 2013/083858, and WO 2004/067566.

Examples of FVIII molecules, which can be used in a composition of the present invention include the active ingredient of Advate®, Helixate®, Kogenate®, Xyntha® as well as the FVIII molecule described in WO 2008/135501, WO 2009/007451 and the construct designated "dBN(64-53)" of WO 2004/067566 (SEQ ID NO:12).

Treatment of Coagulation Disorder

The modified VWF molecules of the invention are useful for treating coagulation disorders including, but not limited to, hemophilia and von Willebrand disease. Preferably, the disease is hemophilia A or von Willebrand disease.

The term "hemophilia A" refers to a deficiency in functional coagulation FVIII, which is usually inherited.

The term "von Willebrand disease" (VWD) refers to a coagulation abnormality associated with a qualitative or quantitative deficiency of VWF.

Treatment of a disease encompasses the treatment of patients already diagnosed as having any form of the disease at any clinical stage or manifestation; the delay of the onset or evolution or aggravation or deterioration of the symptoms or signs of the disease; and/or preventing and/or reducing the severity of the disease.

A "subject" or "patient" to whom a modified VWF molecule of the invention is administered can be a mammal, such as a non-primate (e.g., cow, pig, horse, cat, dog, rat, etc.) or a primate (e.g., monkey or human). In certain aspects, the human is a pediatric patient. In other aspects, the human is an adult patient.

Compositions comprising a modified VWF molecule of the invention and, optionally one or more additional therapeutic agents, such as the second therapeutic agents described below, are described herein. The compositions typically are supplied as part of a sterile, pharmaceutical composition that includes a pharmaceutically acceptable carrier. This composition can be in any suitable form (depending upon the desired method of administering it to a patient).

The modified VWF molecules of the invention can be administered to a patient by a variety of routes such as orally, transdermally, subcutaneously, intranasally, intravenously, intramuscularly, intrathecally, topically or locally. The most suitable route for administration in any given case will depend on the particular molecule to be administered, the subject, and the nature and severity of the disease and the physical condition of the subject. Typically, a modified VWF molecule of the invention will be administered intravenously.

In typical embodiments, a modified VWF molecule of the invention is present in a pharmaceutical composition at a concentration sufficient to permit intravenous administration at 0.5 mg/kg to 20 mg/kg. In some embodiments, the concentration of modified VWF molecule suitable for use in the compositions and methods described herein includes, but is not limited to, 0.5 mg/kg, 0.75 mg/kg, 1 mg/kg, 2 mg/kg, 2.5 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, 20 mg/kg, or a concentration ranging between any of the foregoing values, e.g., 1 mg/kg to 10 mg/kg, 5 mg/kg to 15 mg/kg, or 10 mg/kg to 18 mg/kg.

The effective dose of a modified VWF molecule of the invention can range from about 0.001 to about 750 mg/kg per single (e.g., bolus) administration, multiple administrations or continuous administration, or to achieve a serum concentration of 0.01-5000 μg/ml serum concentration per single (e.g., bolus) administration, multiple administrations or continuous administration, or any effective range or value therein depending on the condition being treated, the route of administration and the age, weight and condition of the subject. In certain embodiments, each dose can range from about 0.5 mg to about 50 mg per kilogram of body weight or from about 3 mg to about 30 mg per kilogram body weight. The modified VWF molecule can be formulated as an aqueous solution.

Pharmaceutical compositions can be conveniently presented in unit dose forms containing a predetermined amount of a modified VWF molecule of the invention per dose. Such a unit can contain 0.5 mg to 5 g, for example, but without limitation, 1 mg, 10 mg, 20 mg, 30 mg, 40 mg, 50 mg, 100 mg, 200 mg, 300 mg, 400 mg, 500 mg, 750 mg, 1000 mg, or any range between any two of the foregoing values, for example 10 mg to 1000 mg, 20 mg to 50 mg, or 30 mg to 300 mg. Pharmaceutically acceptable carriers can take a wide variety of forms depending, e.g., on the condition to be treated or route of administration.

Determination of the effective dosage, total number of doses, and length of treatment with a modified VWF molecule of the invention is well within the capabilities of those skilled in the art, and can be determined using a standard dose escalation study.

Therapeutic formulations of the modified VWF molecules of the invention suitable in the methods described herein can be prepared for storage as lyophilized formulations or aqueous solutions by mixing the modified VWF molecule having the desired degree of purity with optional pharmaceutically-acceptable carriers, excipients or stabilizers typically employed in the art (all of which are referred to herein as "carriers"), i.e., buffering agents, stabilizing agents, preservatives, isotonifiers, non-ionic detergents, antioxidants, and other miscellaneous additives. See, Remington's Pharmaceutical Sciences, 16th edition (Osol, ed. 1980). Such additives must be nontoxic to the recipients at the dosages and concentrations employed.

Buffering agents help to maintain the pH in the range which approximates physiological conditions. They can present at concentration ranging from about 2 mM to about 50 mM. Suitable buffering agents include both organic and inorganic acids and salts thereof such as citrate buffers (e.g., monosodium citrate-disodium citrate mixture, citric acid-trisodium citrate mixture, citric acid-monosodium citrate mixture, etc.), succinate buffers (e.g., succinic acid-monosodium succinate mixture, succinic acid-sodium hydroxide mixture, succinic acid-disodium succinate mixture, etc.), tartrate buffers (e.g., tartaric acid-sodium tartrate mixture, tartaric acid-potassium tartrate mixture, tartaric acid-sodium hydroxide mixture, etc.), fumarate buffers (e.g., fumaric acid-monosodium fumarate mixture, fumaric acid-disodium fumarate mixture, monosodium fumarate-disodium fumarate mixture, etc.), gluconate buffers (e.g., gluconic acid-sodium glyconate mixture, gluconic acid-sodium hydroxide mixture, gluconic acid-potassium glyuconate mixture, etc.), oxalate buffer (e.g., oxalic acid-sodium oxalate mixture, oxalic acid-sodium hydroxide mixture, oxalic acid-potassium oxalate mixture, etc), lactate buffers (e.g., lactic acid-sodium lactate mixture, lactic acid-sodium hydroxide mixture, lactic acid-potassium lactate mixture, etc.) and acetate buffers (e.g., acetic acid-sodium acetate mixture, acetic acid-sodium hydroxide mixture, etc.). Additionally, phosphate buffers, histidine buffers and trimethylamine salts such as Tris can be used.

Preservatives can be added to retard microbial growth, and can be added in amounts ranging from 0.2%-1% (w/v). Suitable preservatives include phenol, benzyl alcohol, meta-cresol, methyl paraben, propyl paraben, octadecyldimethylbenzyl ammonium chloride, benzalconium halides (e.g., chloride, bromide, and iodide), hexamethonium chloride, and alkyl parabens such as methyl or propyl paraben, catechol, resorcinol, cyclohexanol, and 3-pentanol. Isotonicifiers sometimes known as "stabilizers" can be added to ensure isotonicity of liquid compositions and include polyhydric sugar alcohols, preferably trihydric or higher sugar alcohols, such as glycerin, erythritol, arabitol, xylitol, sorbitol and mannitol. Stabilizers refer to a broad category of excipients which can range in function from a bulking agent to an additive which solubilizes the therapeutic agent or helps to prevent denaturation or adherence to the container wall. Typical stabilizers can be polyhydric sugar alcohols (enumerated above); amino acids such as arginine, lysine, glycine, glutamine, asparagine, histidine, alanine, ornithine, L-leucine, 2-phenylalanine, glutamic acid, threonine, etc., organic sugars or sugar alcohols, such as lactose, trehalose, stachyose, mannitol, sorbitol, xylitol, ribitol, myoinisitol, galactitol, glycerol and the like, including cyclitols such as inositol; polyethylene glycol; amino acid polymers; sulfur containing reducing agents, such as urea, glutathione, thioctic acid, sodium thioglycolate, thioglycerol, α-monothioglycerol and sodium thio sulfate; low molecular weight polypeptides (e.g., peptides of 10 residues or fewer); proteins such as human serum albumin, bovine serum albumin, gelatin or immunoglobulins; hydrophylic polymers, such as polyvinylpyrrolidone monosaccharides, such as xylose, mannose, fructose, glucose; disaccharides such as lactose, maltose, sucrose and trisaccacharides such as raffinose; and polysaccharides such as dextran. Stabilizers can be present in the range from 0.1 to 10,000 weights per part of weight active protein.

Non-ionic surfactants or detergents (also known as "wetting agents") can be added to help solubilize the therapeutic agent as well as to protect the therapeutic protein against agitation-induced aggregation, which also permits the formulation to be exposed to shear surface stressed without causing denaturation of the protein. Suitable non-ionic surfactants include polysorbates (20, 80, etc.), polyoxamers (184, 188 etc.), Pluronic polyols, polyoxyethylene sorbitan monoethers (TWEEN®-20, TWEEN®-80, etc.). Non-ionic surfactants can be present in a range of about 0.05 mg/ml to about 1.0 mg/ml, or in a range of about 0.07 mg/ml to about 0.2 mg/ml.

Additional miscellaneous excipients include bulking agents (e.g., starch), chelating agents (e.g., EDTA), antioxidants (e.g., ascorbic acid, methionine, vitamin E), and cosolvents.

The formulation herein can also contain a second therapeutic agent in addition to a modified VWF molecule of the invention. Examples of suitable second therapeutic agents are provided below.

The dosing schedule can vary from once a month to daily depending on a number of clinical factors, including the type of disease, severity of disease, and the patient's sensitivity to the modified VWF molecule of the invention. In specific embodiments, a modified VWF molecule of the invention is administered daily, twice weekly, three times a week, every 5 days, every 10 days, every two weeks, every three weeks, every four weeks or once a month, or in any range between any two of the foregoing values, for example from every four weeks to every month, from every 10 days to every two weeks, or from two to three times a week, etc.

The dosage of a modified VWF molecule of the invention to be administered will vary according to the particular modified VWF molecule, the subject, and the nature and severity of the disease, the physical condition of the subject, the therapeutic regimen (e.g., whether a second therapeutic agent is used), and the selected route of administration; the appropriate dosage can be readily determined by a person skilled in the art.

It will be recognized by one of skill in the art that the optimal quantity and spacing of individual dosages of a modified VWF molecule of the invention will be determined by the nature and extent of the condition being treated, the form, route and site of administration, and the age and condition of the particular subject being treated, and that a physician will ultimately determine appropriate dosages to be used. This dosage can be repeated as often as appropriate. If side effects develop the amount and/or frequency of the dosage can be altered or reduced, in accordance with normal clinical practice.

Combination Therapy

Preferably, the patient being treated with the modified VWF molecule of the invention is also treated with a conventional therapy of coagulation disorders. For example, a patient suffering from hemophilia is typically also being treated with blood coagulation factor VIII (Factor VIII).

The concentration of Factor VIII in the composition used according to the present invention is typically in the range of 10-10,000 IU/mL. In different embodiments, the concentration of FVIII molecules in the compositions of the invention is in the range of 10-8,000 IU/mL, or 10-5,000 IU/mL, or 20-3,000 IU/mL, or 50-1,500 IU/mL, or 3,000 IU/mL, or 2,500 IU/mL, or 2,000 IU/mL, or 1,500 IU/mL, or 1,200 IU/mL, 1,000 IU/mL, or 800 IU/mL, or 600 IU/mL, or 500 IU/mL, or 400 IU/mL, or 300 IU/mL, or 250 IU/mL, or 200 IU/mL, or 150 IU/mL, or 100 IU/mL.

"International Unit," or "IU," is a unit of measurement of the blood coagulation activity (potency) of FVIII as measured by a FVIII activity assay such as a one stage clotting assay or a chromogenic substrate FVIII activity assay using a standard calibrated against an international standard preparation calibrated in "IU". One stage clotting assays are known to the art, such as that described in N Lee, Martin L, et al., An Effect of Predilution on Potency Assays of FVIII Concentrates, Thrombosis Research (Pergamon Press Ltd.) 30, 511 519 (1983). Principle of the one stage assay: The test is executed as a modified version of the activated Partial Thromboplastin Time (aPTT)-assay: Incubation of plasma with phospholipids and a surface activator leads to the activation of factors of the intrinsic coagulation system. Addition of calcium ions triggers the coagulation cascade. The time to formation of a measurable fibrin clot is determined. The assay is executed in the presence of Factor VIII deficient plasma. The coagulation capability of the deficient plasma is restored by Coagulation Factor VIII included in the sample to be tested. The shortening of coagulation time is proportional to the amount of Factor VIII present in the sample. The activity of Coagulation Factor VIII is quantified by direct comparison to a standard preparation with a known activity of Factor VIII in International Units.

Another standard assay is a chromogenic substrate assay. Chromogenic substrate assays may be purchased commercially, such as the coamatic FVIII test kit (Chromogenix-Instrumentation Laboratory SpA V. le Monza 338-20128 Milano, Italy). Principle of the chromogenic assay: In the presence of calcium and phospholipid, Factor X is activated by Factor IXa to Factor Xa. This reaction is stimulated by Factor VIIIa as cofactor. FVIIIa is formed by low amounts of thrombin in the reaction mixture from FVIII in the sample to be measured. When using the optimum concentrations of Ca2+, phospholipid and Factor IXa and an excess quantity of Factor X, activation of Factor X is proportional to the potency of Factor VIII. Activated Factor X releases the chromophore pNA from the chromogenic substrate S-2765. The release of pNA, measured at 405 nm, is therefore proportional to the amount of FXa formed, and, therefore, also to the Factor VIII activity of the sample.

In one embodiment, the treatment comprises administering the modified VWF molecule of the invention and Factor VIII to a patient suffering from hemophilia, preferably hemophilia A.

In another embodiment, the treatment comprises administering the modified VWF molecule of the invention and a compound capable of binding to CLEC10A to a patient suffering from VWD or hemophilia, preferably hemophilia A.

In yet another embodiment, the treatment comprises administering the modified VWF molecule of the invention, a Factor VIII molecule, and a compound capable of binding to CLEC10A to a patient suffering from hemophilia, preferably hemophilia A.

In a particular embodiment, the modified VWF molecule of the invention and the second therapeutic agent (e.g. Factor VIII and/or a compound capable of binding to CLEC10A) are administered simultaneously. In another embodiment, the modified VWF molecule of the invention and the second therapeutic agent (e.g. Factor VIII and/or a compound capable of binding to CLEC10A) are administered separately. The time between the administration of the modified VWF molecule of the invention and the second therapeutic agent (e.g. Factor VIII and/or a compound capable of binding to CLEC10A) is not particularly limited. It is preferred that the modified VWF molecule of the invention is administered prior to the compound capable of binding to CLEC10A.

CLEC10A

CLEC10A, also known as macrophage Gal-type lectin, is a human type II transmembrane receptor protein of the CLEC family. Further synonyms are C-type lectin superfamily member 14, Macrophage lectin 2, and CD301. CLEC10A is closely related to the hepatic ASGPR proteins but is expressed by intermediate monocytes, macrophages and dendritic cells. As used herein, the term "CLEC10A" refers to a human protein having or consisting of the amino acid sequence as shown in the UniProt database under one of the identifiers Q8IUN9-1, Q8IUN9-2, and Q8IUN9-3. Most preferably, the CLEC10A comprises or consists of the amino acid sequence as shown in the UniProt database under one of the identifiers Q8IUN9-1.

Compound Capable of Binding to CLEC10A

The type or class of the compound capable of binding to CLEC10A (hereinafter referred to as "the compound") is not particularly limited. Preferably, however, the compound is a peptide or polypeptide, most preferably the compound is an antibody or a fragment thereof.

The term "antibody", as used herein, refers to an immunoglobulin molecule that binds to, or is immunologically reactive with, a particular antigen, and includes polyclonal, monoclonal, genetically engineered and otherwise modified forms of antibodies, including but not limited to chimeric antibodies, humanized antibodies, human antibodies, heteroconjugate antibodies (e.g., bispecific antibodies, diabodies, triabodies, and tetrabodies), single-domain antibodies (nanobodies) and antigen binding fragments of antibodies, including e.g., Fab', F(ab')2, Fab, Fv, rIgG, and scFv fragments. Moreover, unless otherwise indicated, the term "monoclonal antibody" (mAb) is meant to include both intact molecules, as well as, antibody fragments (such as, for example, Fab and F(ab')2 fragments) which are capable of binding to a protein. Fab and F(ab')2 fragments lack the Fc fragment of intact antibody, clear more rapidly from the circulation of the animal or plant, and may have less non-specific tissue binding than an intact antibody (Wahl et al, 1983, J. Nucl. Med. 24:316).

The antibody used in the invention is capable of binding to at least one variant of CLEC10A. In other embodiments, the antibody is capable of binding to the extracellular domain of CLEC10A, e.g. to an epitope within amino acids 61-316 of the amino acid sequence of CLEC10A. Preferably, the antibody binds to the lectin binding site of CLEC10A.

It is also preferred that the antibody specifically binds to CLEC10A. In one embodiment, the antibody is capable of binding to CLEC10A, but is not capable of binding to all of the following receptors: ASGPR1, COLEC12, CLEC4F, CLEC4M, SCARA5 and MMR. In another embodiment, the antibody is capable of binding to CLEC10A, but is not capable of binding to ASGPR1 (UniProt identifier: P07306). In another embodiment, the antibody is capable of binding to CLEC10A, but is not capable of binding to COLEC12 (UniProt identifier: Q5KU26). In another embodiment, the antibody is capable of binding to CLEC10A, but is not capable of binding to CLEC4F (UniProt identifier: Q8N1N0). In another embodiment, the antibody is capable of binding to CLEC10A, but is not capable of binding to CLEC4M (UniProt identifier: Q9H2X3). In another embodiment, the antibody is capable of binding to CLEC10A, but is not capable of binding to SCARA5 (UniProt identifier: Q6ZMJ2). In another embodiment, the antibody is capable of binding to CLEC10A, but is not capable of binding to MMR (UniProt identifier: P22897). In yet another embodiment, the antibody is capable of binding to CLEC10A, but is not capable of binding to any one of the following receptors: ASGPR1, COLEC12, CLEC4F, CLEC4M, SCARA5 and MMR.

In another embodiment, the antibody is capable of binding to at least one murine ortholog of CLEC10A. In that embodiment, the antibody may be capable of binding to MGL1, to MGL2, or to both MGL1 and MGL2. The antibody may be capable of binding to a protein having or consisting of the amino acid sequence defined in UniProt identifier No. P49300. The antibody may be capable of binding to a protein having or consisting of the amino acid sequence defined in UniProt identifier No. F8WHB7. The antibody may be capable of binding to a protein having or consisting of the amino acid sequence defined in UniProt identifier No. Q8JZN1

In another embodiment, the antibody is capable of binding to the rat ortholog of CLEC10A. In another embodiment, the antibody is capable of binding to the rabbit ortholog of CLEC10A. In another embodiment, the antibody is capable of binding to the *Macaca fascicularis* ortholog and/or to the *Macaca mulatta* ortholog of CLEC10A.

The dissociation constant $K_D$ for the complex formed by CLEC10A and antibody is preferably less than 100 nM, more preferably less than 10 nM, most preferably less than 5 nM. Typically the $K_D$ ranges from about 10 pM to about 100 nM, or from about 100 pM to about 10 nM, or from about 500 pM to about 5 nM.

Preferably, the antibody used in this invention is a monoclonal antibody. The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced. Monoclonal antibodies can be prepared using a wide variety of techniques known in the art including the use of hybridoma, recombinant, and phage display technologies, or a combination thereof. (Harlow and Lane, "Antibodies, A Laboratory Manual" CSH Press 1988, Cold Spring Harbor N.Y.).

In other embodiments, including in vivo use of the anti-CLEC10A antibodies in humans, chimeric, primatized, humanized, or human antibodies can be used. In a preferred embodiment, the antibody is a human antibody or a humanized antibody, more preferably a monoclonal human antibody or a monoclonal humanized antibody.

The term "chimeric" antibody as used herein refers to an antibody having variable sequences derived from a non-human immunoglobulins, such as rat or mouse antibody, and human immunoglobulins constant regions, typically chosen from a human immunoglobulin template. Methods for producing chimeric antibodies are known in the art. See, e.g., Morrison, 1985, Science 229 (4719): 1202-7; Oi et al, 1986, BioTechniques 4:214-221; Gillies et al., 1985, J. Immunol.

Methods 125: 191-202; U.S. Pat. Nos. 5,807,715; 4,816,567; and 4,816397, which are incorporated herein by reference in their entireties.

"Humanized" forms of non-human (e.g., murine) antibodies are chimeric immunoglobulins, immunoglobulin chains or fragments thereof (such as Fv, Fab, Fab', F(ab')2 or other target-binding subsequences of antibodies) which contain minimal sequences derived from non-human immunoglobulin. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody can also comprise at least a portion of an immunoglobulin constant region (Fc), typically that of a human immunoglobulin template chosen. Humanization is a technique for making a chimeric antibody in which one or more amino acids or portions of the human variable domain have been substituted by the corresponding sequence from a non-human species. Humanized antibodies are antibody molecules generated in a non-human species that bind the desired antigen having one or more complementarity determining regions (CDRs) from the non-human species and framework (FR) regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. See, e.g., Riechmann et al., 1988, Nature 332:323-7 and Queen et al, U.S. Pat. Nos. 5,530,101; 5,585,089; 5,693,761; 5,693,762; and 6,180,370 (each of which is incorporated by reference in its entirety). Antibodies can be humanized using a variety of techniques known in the art including, for example, CDR-grafting (EP239400; PCT publication WO 91/09967; U.S. Pat. Nos. 5,225,539; 5,530,101 and 5,585,089), veneering or resurfacing (EP592106; EP519596; Padlan, 1991, Mol. Immunol, 28:489-498; Studnicka et al, 1994, Prot. Eng. 7:805-814; Roguska et al, 1994, Proc. Natl. Acad. Sci. 91:969-973, and chain shuffling (U.S. Pat. No. 5,565,332), all of which are hereby incorporated by reference in their entireties.

In some embodiments, humanized antibodies are prepared as described in Queen et al, U.S. Pat. Nos. 5,530,101; 5,585,089; 5,693,761; 5,693,762; and 6,180,370 (each of which is incorporated by reference in its entirety).

In some embodiments, the anti-CLEC10A antibodies are human antibodies. Completely "human" anti-CLEC10A antibodies can be desirable for therapeutic treatment of human patients. As used herein, "human antibodies" include antibodies having the amino acid sequence of a human immunoglobulin and include antibodies isolated from human immunoglobulin libraries or from animals transgenic for one or more human immunoglobulin and that do not express endogenous immunoglobulins. Human antibodies can be made by a variety of methods known in the art including phage display methods described above using antibody libraries derived from human immunoglobulin sequences. See U.S. Pat. Nos. 4,444,887 and 4,716,111; and PCT publications WO 98/46645; WO 98/50433; WO 98/24893; WO 98/16654; WO 96/34096; WO 96/33735; and WO 91/10741, each of which is incorporated herein by reference in its entirety. Human antibodies can also be produced using transgenic mice which are incapable of expressing functional endogenous immunoglobulins, but which can express human immunoglobulin genes. See, e.g., PCT publications WO 98/24893; WO 92/01047; WO 96/34096; WO 96/33735; U.S. Pat. Nos. 5,413,923; 5,625,126; 5,633,425; 5,569,825; 5,661,016; 5,545,806; 5,814,318; 5,885,793; 5,916,771; and 5,939,598, which are incorporated by reference herein in their entireties. Completely human antibodies that recognize a selected epitope can be generated using a technique referred to as "guided selection." In this approach a selected non-human monoclonal antibody, e.g., a mouse antibody, is used to guide the selection of a completely human antibody recognizing the same epitope (Jespers et al, 1988, Biotechnology 12:899-903).

In some embodiments, the anti-CLEC10A antibodies are primatized antibodies. The term "primatized antibody" refers to an antibody comprising monkey variable regions and human constant regions. Methods for producing primatized antibodies are known in the art. See e.g., U.S. Pat. Nos. 5,658,570; 5,681,722; and 5,693,780, which are incorporated herein by reference in their entireties.

In some embodiments, the anti-CLEC10A antibodies are derivatized antibodies. For example, but not by way of limitation, the derivatized antibodies that have been modified, e.g., by glycosylation, acetylation, pegylation, phosphorylation, amidation, derivatization by known protecting/blocking groups, proteolytic cleavage, linkage to a cellular ligand or other protein (see infra for a discussion of antibody conjugates), etc. Any of numerous chemical modifications may be carried out by known techniques, including, but not limited to, specific chemical cleavage, acetylation, formylation, metabolic synthesis of tunicamycin, etc. Additionally, the derivative may contain one or more non-classical amino acids.

In some embodiments, the anti-CLEC10A antibodies or fragments thereof can be antibodies or antibody fragments whose sequence has been modified to reduce at least one constant region-mediated biological effector function relative to the corresponding wild type sequence. To modify an anti-CLEC10A antibody such that it exhibits reduced binding to the Fc receptor, the immunoglobulin constant region segment of the antibody can be mutated at particular regions necessary for Fc receptor (FcR) interactions (See e.g., Canfield and Morrison, 1991, J. Exp. Med. 173: 1483-1491; and Lund et al, 1991, J. Immunol. 147:2657-2662). Reduction in FcR binding ability of the antibody can also reduce other effector functions which rely on FcR interactions, such as opsonization and phagocytosis and antigen-dependent cellular cytotoxicity.

In yet other aspects, the anti-CLEC10A antibodies or fragments thereof can be antibodies or antibody fragments that have been modified to increase or reduce their binding affinities to the fetal Fc receptor, FcRn. To alter the binding affinity to FcRn, the immunoglobulin constant region segment of the antibody can be mutated at particular regions necessary for FcRn interactions (See e.g., WO 2005/123780). Increasing the binding affinity to FcRn should increase the antibody's serum half-life, and reducing the binding affinity to FcRn should conversely reduce the antibody's serum half-life. In particular embodiments, the anti-CLEC10A antibody is of the IgG class in which at least one of amino acid residues 250, 314, and 428 of the heavy chain constant region is substituted with an amino acid residue different from that present in the unmodified antibody. The antibodies of IgG class include antibodies of IgG1, IgG2, IgG3, and IgG4. The substitution can be made at position 250, 314, or 428 alone, or in any combinations thereof, such as at positions 250 and 428, or at positions 250 and 314, or at positions 314 and 428, or at positions 250, 314, and 428, with positions 250 and 428 as a preferred combination. For each position, the substituting amino acid can be any amino acid residue different from that present in that position of the unmodified antibody. For position 250, the substituting amino acid residue can be any amino acid residue other than threonine, including, but not limited to, alanine, cysteine, aspartic acid, glutamic acid, phenylalanine, glycine, histidine, isoleucine, lysine, leucine, methionine, asparagine, proline, glutamine, arginine, serine, valine, tryptophan, or tyrosine. For position 314, the substituting amino acid residue can be any amino acid residue other than leucine, including, but not limited to, alanine, cysteine, aspartic acid, glutamic acid, phenylalanine, glycine, histidine, isoleucine, lysine, methionine, asparagine, proline, glutamine, arginine, serine, threonine, valine, tryptophan, or tyrosine. For position 428, the substituting amino acid residues can be any amino acid residue other than methionine, including, but not limited to, alanine, cysteine, aspartic acid, glutamic acid, phenylalanine, glycine, histidine, isoleucine, lysine, leucine, asparagine, proline, glutamine, arginine, serine, threonine, valine, tryptophan, or tyrosine. Specific combinations of suitable amino acid substitutions are identified in Table 1 of WO 2005/123780, which table is incorporated by reference herein in its entirety. See also, Hinton et al, U.S. Pat. Nos. 7,217,797, 7,361,740, 7,365,168, and 7,217,798, which are incorporated herein by reference in their entireties.

In yet other aspects, an anti-CLEC10A antibody has one or more amino acids inserted into one or more of its hypervariable region, for example as described in US 2007/0280931.

Antibody Conjugates

In some embodiments, the anti-CLEC10A antibodies are antibody conjugates that are modified, e.g., by the covalent attachment of any type of molecule to the antibody, such that covalent attachment does not interfere with binding to CLEC10A. Techniques for conjugating effector moieties to antibodies are well known in the art (See, e.g., Hellstrom et ah, Controlled Drag Delivery, 2nd Ed., at pp. 623-53 (Robinson et ah, eds., 1987)); Thorpe et ah, 1982, Immunol. Rev. 62: 119-58 and Dubowchik et al., 1999, Pharmacology and Therapeutics 83:67-123).

In one example, the antibody or fragment thereof is fused via a covalent bond (e.g., a peptide bond), at optionally the N-terminus or the C-terminus, to an amino acid sequence of another protein (or portion thereof; preferably at least a 10, 20 or 50 amino acid portion of the protein). Preferably the antibody, or fragment thereof, is linked to the other protein at the N-terminus of the constant domain of the antibody. Recombinant DNA procedures can be used to create such fusions, for example as described in WO 86/01533 and EP0392745. In another example the effector molecule can increase half-life in vivo. Examples of suitable effector molecules of this type include polymers, albumin, albumin binding proteins or albumin binding compounds such as those described in WO 2005/117984.

In some embodiments, anti-CLEC10A antibodies can be attached to poly(ethyleneglycol) (PEG) moieties. For example, if the antibody is an antibody fragment, the PEG moieties can be attached through any available amino acid side-chain or terminal amino acid functional group located in the antibody fragment, for example any free amino, imino, thiol, hydroxyl or carboxyl group. Such amino acids can occur naturally in the antibody fragment or can be engineered into the fragment using recombinant DNA methods. See for example U.S. Pat. No. 5,219,996. Multiple sites can be used to attach two or more PEG molecules. Preferably PEG moieties are covalently linked through a thiol group of at least one cysteine residue located in the antibody fragment. Where a thiol group is used as the point of attachment, appropriately activated effector moieties, for example thiol selective derivatives such as maleimides and cysteine derivatives, can be used.

In another example, an anti-CLEC10A antibody conjugate is a modified Fab' fragment which is PEGylated, i.e., has PEG (poly(ethyleneglycol)) covalently attached thereto, e.g., according to the method disclosed in EP0948544. See also Poly(ethyleneglycol) Chemistry, Biotechnical and Biomedical Applications, (J. Milton Harris (ed.), Plenum Press, New York, 1992); Poly(ethyleneglycol) Chemistry and Biological Applications, (J. Milton Harris and S. Zalipsky, eds., American Chemical Society, Washington D.C., 1997); and Bioconjugation Protein Coupling Techniques for the Biomedical Sciences, (M. Aslam and A. Dent, eds., Grove Publishers, New York, 1998); and Chapman, 2002, Advanced Drug Delivery Reviews 54:531-545.

Another embodiment that can be used to block the CLEC10A receptor is a VWF-C1 domain comprising the O-glycosylation site at position 2298, linked to a half-life extending moiety such as fused to albumin, preferably via a linker. A preferred embodiment is the fusion protein with the amino acid sequence as shown in SEQ ID NO: 9.

Kits

Another aspect of the present invention is a pharmaceutical kit comprising (i) a modified VWF molecule as defined hereinabove and (ii) a polypeptide selected from the group consisting of Factor VIII, a compound (preferably an antibody) capable of binding to CLEC10A, and combinations thereof. Preferably, the modified VWF molecule and the polypeptide are contained in separate compositions.

Another aspect of the present invention is a pharmaceutical kit comprising (i) a modified VWF molecule as defined hereinabove and (ii) a polypeptide selected from the group consisting of Factor VIII, a compound (preferably an antibody) capable of binding to CLEC10A, and combinations thereof, for simultaneous, separate or sequential use in the treatment of a blood coagulation disorder.

Another aspect of the invention is the use of a modified VWF molecule as defined hereinabove for increasing the half-life or reducing the clearance of Factor VIII.

The term "half-life" refers to the time it takes to eliminate half of the protein from the circulation in vivo. The area under the curve (AUC) can be determined to assess clearance effects. A reduction in clearance leads to higher AUC values, and to an increase in half-life.

Yet another aspect of the invention is the use of a compound (preferably an antibody) as defined hereinabove for increasing the half-life of Factor VIII, preferably in a therapeutic treatment.

The invention further relates to a method of increasing the half-life or reducing the clearance of Factor VIII in vivo, comprising administering to a subject an effective amount of a modified VWF molecule as defined hereinabove.

A further aspect of this invention is a method of treating a blood coagulation disorder, comprising administering to a patient in need thereof an effective amount of a modified VWF molecule as defined hereinabove.

A further aspect is the use of a modified VWF molecule as defined hereinabove for reducing the frequency of administration of FVIII in a treatment of hemophilia A. The frequency of intravenous or subcutaneous administration of FVIII may be reduced to twice per week. Alternatively, the frequency of intravenous or subcutaneous administration of FVIII may be reduced to once per week.

A further aspect is the use of a modified VWF molecule as defined hereinabove for reducing the frequency of administration of VWF in a treatment of VWD. The frequency of intravenous or subcutaneous administration of VWF may be reduced to twice per week. Alternatively, the frequency of intravenous or subcutaneous administration of VWF may be reduced to once per week. That is, the modified VWF molecule of the invention is administered once or twice per week.

Another aspect is the use of a modified VWF molecule as defined hereinabove for reducing the dose FVIII to be administered in a treatment of hemophilia A.

Another aspect is the use of a modified VWF molecule as defined hereinabove for reducing the dose VWF to be administered in a treatment of VWD.

The following table summarizes the nucleotide and amino acid sequences shown in the sequence listing:

| SEQ ID NO: | Remark |
| --- | --- |
| 1 | DNA sequence encoding the prepropeptide of human native VWF |
| 2 | Amino acid sequence of the prepropeptide of human native VWF |
| 3 | Primer |
| 4 | Primer |
| 5 | Primer |
| 6 | Primer |
| 7 | Primer |
| 8 | Primer |
| 9 | Amino acid sequence of a C1 domain of human VWF, fused to human albumin via a Gly-Ser linker |
| 10 | C1 domain of a modified VWF having a mutation of T2298 |
| 11 | Mature form of modified VWF having a mutation of T2298 |
| 12 | Single chain Factor VIII molecule |

EXAMPLES

Figure 2:
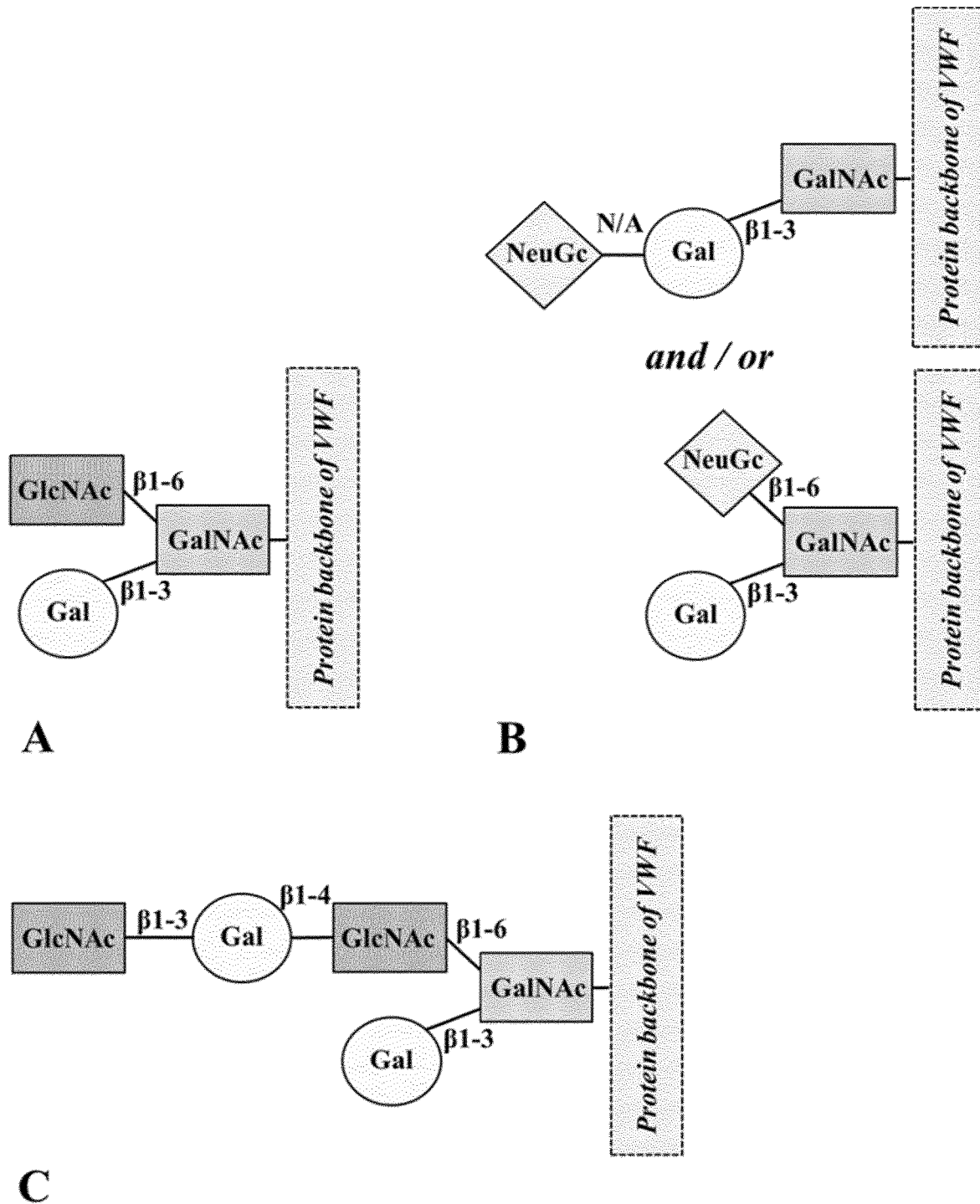
FIG. 2: Predominant O-glycans detected in eluate fractions after incubating tryptic VWF fragments with soluble CLEC10A (NeuGc=N-glycolylneuraminic acid; GlcNAc=N-acetylglucosamine; Gal=galactose; GalNAc=N-acetylgalactosamine)

Example 1: Specific Glycosylation Structures Present on VWF were Identified to Interact with CLEC10A, as Well as O-Linked Glycan Site 2298 Present on VWF In order to identify the binding site on human VWF for CLEC10A, tryptic fragments of VWF were incubated with soluble CLEC10A. After washing, bound protein fragments were eluted at pH 11 and by using a solution containing 100 mM GalNAc, respectively. The elution conditions were chosen based on preliminary SPR experiments which indicated that all components bound to CLEC10A are completely eluted under the defined conditions. Subsequently, the respective eluate fractions were subjected to MS analysis. Free N- and O-glycans were permethylated and characterized by MALDI-TOF-MS analysis. The resulting data demonstrated that CLEC10A differed significantly in their recognition of N- and O-glycans. In comparison to the VWF fragments used as starting material (glycan analysis observed the presence of 18% non-sialylated O-glycans), both eluate fractions revealed a strong enrichment of non-sialylated O-glycans whereas sialylated O-glycans containing one or more NeuAc residues were extremely decreased as well as N-glycans regardless of their sialylation status. The different elution conditions (alkaline versus GalNAc) resulted in only slightly different glycan patterns. Three predominant O-glycosylation structures could be identified in the eluate fractions, which represented approximately 80% of all O-glycan structures detected. The respective structures are given in FIG. 2. The enrichment of core 2 glycan (concentration factor of more than 40), core 1 glycan carrying one NeuGc residue (concentration factor of approximately 9) and core 2 glycan elongated with the disaccharide GlcNAcβ1,3Gal (concentration factor of approximately 7) were identified by MALDI-TOF-MS analyses. The concentration factor mentioned in brackets quantitatively describes the enrichment of the respective glycan, when compared with the starting material prior to incubation with CLEC10A.

In addition to the investigation described before, analysis was performed by nano liquid chromatography electrospray ionization MS/MS after deglycosylation of VWF fragments. The resulting peptide pattern detected in each of the two different eluate fractions was comparable, and therefore was independent of the elution condition applied. As a result, VWF peptides containing threonine 2298 were clearly identified after elution. The involvement of other glycosylated VWF fragments in CLEC10A-binding could be excluded, based on the analytical data obtained. Thus, it is most likely that O-linked glycan site T2298 contained a glycan structure that was not sialylated, and therefore interacted with CLEC10A. Furthermore, this glycosylation site present on VWF was exclusively identified as being a predominant interaction partner of CLEC10A, and therefore was solely found to be responsible for receptor interaction. All other VWF glycan sites appeared to be not involved in CLEC10A-binding.

In summary, after elution of tryptic-digested VWF fragments from soluble CLEC10A, MS analyses demonstrated that non-sialylated O-glycans were found to bind to CLEC10A whereas sialylated O-glycans as well as N-glycans regardless of their sialylation status did not interact with CLEC10A significantly. Three predominant O-glycosylation structures (Core 2 glycan, core 1 glycan carrying one NeuGc residue and core 2 glycan elongated with the disaccharide GlcNAcβ1,3Gal) present on VWF were identified as being responsible for the interaction. Due to the fact that an extremely high concentration factor was detected for core 2 glycan in comparison to both other structures, this glycan present on VWF seemed to have a strong affinity to CLEC10A. In addition, only VWF peptides containing O-linked glycan site 2298 were identified to bind to CLEC10A, and therefore contained a glycan structure that was not sialylated. Ultimately, these results were surprising and indicated that the glycan site T2298 was solely responsible for VWF-CLEC10A interaction. Moreover, the observed glycosylation patterns appeared to be only present at T2298. Based on these results and the observation that CLEC10A mediated VWF clearance, it can be suggested that the clearance of natively glycosylated VWF by CLEC10A was only affected by the O-linked glycosylation site 2298. Consequently, with the aim to prevent CLEC10A-binding, a decreased clearance of VWF mutants can be assumed after manipulating the respective O-glycosylation site and/or the respective carbohydrate structures identified to be present at this glycan site.

Methods

1) Reduction and Carboxymethylation of VWF

A volume of 30 mL of VWF solution that had been purified according to the method described in the previous section was further dialyzed overnight against 1 L of reduction buffer (50 mM Tris, 100 mM NaCl, pH 8.5) at +4° C. This procedure was repeated again, except that the second dialysis was performed for 4 hours at RT. Subsequently, the solution was adjusted to 15 mM DTT by adding a stock solution of 1 M DTT under gentle stirring (IKA, Staufen, Germany). Reduction of VWF was carried out by incubation for 60 min at +37° C. VWF was then alkylated with 40 mM iodoacetamide by adding a 1 M stock solution and the solution was incubated for 60 minutes at RT.

2) Enzymatic Digestion of Monomeric VWF Purified from Human Plasma

After reduction and alkylation based on the method described before, 60 mL of monomeric VWF (protein concentration of 1 mg/mL) was dialyzed overnight at +4° C. via Membra-Cel MD25-14 dialysis tubing (Serva, Heidelberg, Germany) against 20 L of 50 mM $NH_4HCO_3$ (pH 7.8). The dialyzing step was repeated 2 times. Immobilized trypsin resin (Promega, Mannheim, Germany) was washed with 50 mM $NH_4HCO_3$ (pH 7.8) and added to the protein solution, resulting in a concentration of 1 mL trypsin resin per 8 mg protein. Subsequently, the suspension was incubated on a rotating mixer (Glaswarenfabrik Karl Hecht, Sondheim, Germany) at +37° C. for 24 hours. After the reaction, immobilized trypsin was separated by centrifugation (Multifuge 3SR, Heraeus, Osterode, Germany) at 2,000×g at +20° C. for 15 minutes. After an additional filtration step (pore size of 0.45 µm, Sterivex-HV, Millipore, Cork, Ireland), the reaction mixture was transferred to Centricon Plus-70 devices (Merck Millipore, Darmstadt, Germany) and centrifugation (Multifuge 3SR, Heraeus, Osterode, Germany) was performed at 3,000×g at RT for 15 minutes. A successful cleavage reaction was demonstrated by SDS-PAGE (data not shown). The depletion of trypsin was confirmed by applying a chromogenic substrate (data not shown). The tryptic fragments (protein concentration of approximately 0.5 mg/mL) were concentrated in a SpeedVac vacuum concentrator system (Thermo Scientific, Langenselbold, Germany) to a final concentration of approximately 40 mg/mL. Ultimately, the peptide profile of the concentrated VWF fragments was investigated by MS analysis and compared with the profile obtained for the intermediate fraction prior to the first centrifugation step, thereby providing evidence that both samples had the same composition of VWF fragments.

3) Identification of Tryptic VWF Fragments Interacting with CLEC10A

To identify which of the glycan chains present on VWF were involved in interacting with CLEC10A, tryptic VWF fragments were incubated with soluble CLEC10A (R&D Systems, Wiesbaden, Germany). 1 mg of lyophilized receptor protein was dissolved in 2 mL of reaction buffer containing 10 mM HEPES, 150 mM NaCl and 5 mM $CaCl_2$ at pH 7.4. 20 mL of concentrated VWF fragments after trypsin digestion with a protein content of 0.5 mg/mL were adjusted to the same buffer conditions by adding a 20-times concentrated buffer stock solution, and then mixed with the solution containing the receptor protein. Incubation was carried out overnight at +37° C. under gentle mixing (Glaswarenfabrik Karl Hecht, Sondheim, Germany). Afterwards, unbound VWF fragments were separated by centrifugation (Amicon Ultra-15 centrifugal filter units, NMWL 10 kDa, Merck Millipore, Darmstadt, Germany) at 3,000×g (Multifuge 3SR, Heraeus, Osterode, Germany) and discarded. Centrifugation was performed at RT until a remaining volume of 0.5 mL was reached. The concentrated reaction mixture containing the receptor protein interacting with VWF fragments was then washed with reaction buffer and concentrated again. After repeating this washing step of the concentrated solution 2 times, the reaction mixture was divided into two equal portions, which were then treated with two different elution buffers. On the one hand, bound protein fragments were eluted at pH 11 (100 mM glycine/NaOH buffer, pH 11.0), on the other, by using a solution containing GalNAc (100 mM GalNAc, pH 4.3). The respective elution buffer was added to the washed and concentrated solution and incubation was carried out overnight at RT under gentle mixing. After separation by centrifugation, the resulting filtrate containing the eluted VWF fragments was collected and analyzed by MS.

4) Analysis of Tryptic VWF Fragments Interacting with Clearance Receptor

Isolated tryptic fragments were deglycosylated by PNGase F treatment and β-elimination, and then analyzed by applying nano liquid chromatography electrospray ionization MS/MS. In addition, the free N- and O-glycans were permethylated and characterized by MALDI-TOF-MS analysis. Analysis was performed based on published methods (Canis et al. (2010) Journal of Thrombosis and Haemostasis, 8: 137-145; Canis et al. (2012) The Biochemical Journal, 447: 217-228).

Example 2: Generation of an Expression Vector for VWF Mutant T2298

An expression plasmid containing a full length VWF cDNA sequence in its multiple cloning site had been generated previously. The VWF cDNA sequence contained in this vector is displayed as SEQ ID NO:1, its corresponding protein sequence as SEQ ID NO:2.

For generating such expression vectors, the VWF cDNA was amplified by polymerase chain reaction (PCR) using primer set VWF+ and VWF− (SEQ ID NO. 3 and 4) under standard conditions known to those skilled in the art (and as described e.g. in Current Protocols in Molecular Biology, Ausubel F M et al. (eds.) John Wiley & Sons, Inc. from a plasmid containing VWF cDNA (as obtainable commercially, e.g. pMT2-VWF from ATCC, No. 67122). The resulting PCR fragment was digested by restriction endonuclease EcoRI and ligated into expression vector pIRESneo3 (BD Biosciences, Franklin Lakes, N.J., USA) which had been linearized by EcoRI. The resulting expression plasmid with correct orientation of the insert contained a wild-type cDNA of VWF downstream of the CMV promoter.

In order to introduce mutations into the VWF sequence site directed mutagenesis (QuickChange XL Site Directed Mutagenesis Kit, Stratagene, La Jolla, Calif., USA) was applied on the above described plasmid according to the following protocol as suggested by the kit manufacturer. Per mutagenesis reaction 5 µl of 10× reaction buffer, 1 µl of plasmid DNA (50 ng), 1 µl (10 pmol/µl) each of the respective two mutagenesis oligonucleotides We4781 and We4782 (SEQ ID NO. 5 and 6), 1 µl dNTP Mix, 3 µl Quick-Solution, 1 µl Turbo Polymerase (2.5 U/µl) and 37 µl $H_2O$ were mixed and subjected to a polymerase chain reaction with an initial denaturation for 2 min at 95° C., 18 cycles of a) denaturation for 50 sec. at 95° C., b) annealing for 50 sec at 60° C. and c) elongation for 17 min at 68° C., followed by a single terminal elongation phase of 7 min at 68° C. Subsequently 1 µl of Dpnl enzyme from the kit was added and the reaction incubated for another 60 min at 37° C. After that 3 µl of the mutagenesis reaction were transformed into E. coli. Clones were isolated, plasmid DNA extracted and the mutation in the VWF sequence was verified by DNA sequencing.

Using the protocols and plasmid described above and by applying molecular biology techniques known to those skilled in the art (and as described e.g. in Current Protocols in Molecular Biology, ibid) other constructs can be made by the artisan for mutation of other amino acid residues.

Example 3: Generation of an Expression Vector for an Albumin Fused VWF Fragment Containing the T2298 Residue In order to generate an expression vector for a VWF fragment containing amino acid residues 2276 to 2326 fused to human albumin, the coding sequences for the VWF fragment including an N-terminal signal peptide and a C-terminal 28 amino acid glycin/serine linker are manufactured by gene synthesis (Eurofins MWG Synthesis, Ebersberg, Germany) with an NheI restriction site at the 5"-end and a BamH1 site at the 3"-end. This fragment is excised from the cloning vector provided by NheI and BamH1 digestion, purified and cloned into NheI/BamH1 digested expression vector pIRESneo3 (ibid).

The albumin coding sequence is amplified by PCR. For that 1 µl of wild-type albumin cDNA containing plasmid DNA (50 ng), 5 µl of 10× reaction buffer, 1 µl (10 pmol/µl) each of the respective two PCR primers HA+ and HA− (SEQ ID NO:7 and 8), 1 µl dNTP Mix, 1 µl Turbo Polymerase (2.5 U/µl) and 40 µl H$_2$O are mixed and subjected to a polymerase chain reaction with an initial denaturation for 2 min at 95° C., 25 cycles of a) denaturation for 20 sec. at 95° C., b) annealing for 20 sec at 61° C. and c) elongation for 7 min at 68° C., followed by a single terminal elongation phase of 7 min at 68° C. The fragment is purified, digested with BamH1 and Not1 and ligated into the BamH1 and Not1 sites of above described vector containing the VWF fragment. The ligation mix is transformed into E. coli. Clones are isolated, plasmid DNA is extracted and the sequence verified by DNA sequencing. The amino acid sequence of the expressed construct is shown in SEQ ID NO:9.

Example 4: Transfection of Plasmids and Expression of VWF Mutants in CHO Cells Expression plasmids were grown up in E. coli TOP10 (Invitrogen, Carlsbad, Calif., USA) and purified using standard protocols (Qiagen, Hilden, Germany). CHO K1 cells were transfected with expression plasmids using the Lipofectamine 2000 reagent (Invitrogen). Single clones were isolated and grown up in serum-free medium (CD-CHO, Life Technologies) in the presence of 750 µg/ml Geniticin. Clones were spread through T-flasks into shake flasks and bioreactors from which supernatants were harvested for purification of the respective recombinant VWF protein.

Example 5: Quantitation of VWF Antigen

VWF antigen in culture supernatant was determined by an ELISA whose performance is known to those skilled in the art. Briefly, microplates were incubated with 100 µL per well of the capture antibody (rabbit anti human vWF-IgG, Dako A0082 [Dako, Hamburg, Germany], diluted 1:2000 in buffer A [Sigma C3041, Sigma-Aldrich, Munich, Germany]) overnight at ambient temperature. After washing plates three times with buffer B (Sigma P3563), each well was incubated with 200 µL buffer C (Sigma P3688) for 1.5 hours at ambient temperature (blocking). After another three wash steps with buffer B, serial dilutions of the test sample in buffer B as well as serial dilutions of standard human plasma (ORKL21; 20-0.2 mU/mL; Siemens Healthcare Diagnostics, Marburg, Germany) in buffer B (volumes per well: 100 µL) were incubated for 1.5 hours at ambient temperature. After three wash steps with buffer B, 100 µL of a 1:16000 dilution in buffer B of the detection antibody (rabbit anti human vWF-IgG, Dako P0226, peroxidase labelled) were added to each well and incubated for 1 hour at ambient temperature. After three wash steps with buffer B, 100 µL of substrate solution (OUVF, Siemens Healthcare Diagnostics) were added per well and incubated for 30 minutes at ambient temperature in the dark. Addition of 100 µL undiluted stop dilution (OSFA, Siemens Healthcare Diagnostics) prepared the samples for reading in a suitable microplate reader at 450 nm wavelength. Concentrations of the test samples were then calculated using the standard curve with standard human plasma as reference.

Example 6: Pharmacokinetic Analysis of the VWF T2298Q Mutant

VWF-T2298Q from Example 4 and recombinant VWF (wild type) are administered intravenously to a total of 4 CD rats each. The dose is 100 U (VWF:Ag)/kg body weight, at an injection volume of 4 mL/kg.

Blood samples are drawn retroorbitally at appropriate intervals starting at 5 minutes after application of the test substances, using an alternating sampling scheme, resulting in samples from 2 animals/timepoint (t=0, 5, 30, 90 min, 4 h, 1 d for subset Nr. 1 and 0, 15 min, 1, 2, 8 h and 2 d for subset Nr. 2). The scheme is designed to minimize potential effects of blood sampling on the plasma concentration to be quantified. Blood is processed to plasma and stored deep frozen until analysis. The VWF:Ag level in plasma is subsequently quantified by an ELISA as described in example 5. The mean plasma concentration is used for calculation of pharmacokinetic parameters.

The invention claimed is:

1. A method of treating hemophilia A or von Willebrand disease, comprising administering to a patient in need thereof an effective amount of a modified von Willebrand factor (VWF) molecule comprising a C1 domain, wherein the C1 domain comprises an amino acid sequence sharing at least 95% identity to SEQ ID NO: 10, wherein the C1 domain comprises an inactivated O-glycosylation site at amino acid position 44, wherein the amino acid position numbering refers to SEQ ID NO: 10, and wherein the modified VWF molecule is capable of binding to Factor VIII.

2. The method according to claim 1, further comprising administering a Factor VIII molecule.

3. The method according to claim 2, wherein said modified VWF molecule and said Factor VIII molecule are administered separately.

4. The method according to claim 2, wherein said modified VWF molecule and said Factor VIII molecule are administered simultaneously.

5. The method according to claim 2, wherein said modified VWF molecule and said Factor VIII molecule are administered sequentially.

6. The method according to claim 1, wherein the O-glycosylation site at amino acid position 44 has been inactivated by deleting or substituting one or more amino acids at positions 38 to 49.

7. The method according to claim 6, wherein the O-glycosylation site at amino acid position 44 has been deleted or substituted with a different amino acid other than serine or threonine.

8. The method according to claim 7, wherein said different amino acid other than serine or threonine is selected from the group consisting of glycine, alanine, arginine, asparagine, aspartic acid, cysteine, glutamic acid, glutamine, histidine, isoleucine, leucine, lysine, methionine, phenylalanine, proline, tryptophan, tyrosine, and valine.

9. The method according to claim 6, wherein a proline at amino acid position 41, 43, or 48 has been deleted or substituted with a different amino acid.

10. The method according to claim 1, wherein said modified VWF molecule comprises the amino acid sequence of SEQ ID NO: 10.

11. The method according to claim 1, wherein said modified VWF molecule comprises the amino acid sequence of SEQ ID NO: 11.

12. The method according to claim 1, wherein said modified VWF molecule has a reduced in vivo clearance as compared to a native plasma-derived VWF.

13. The method according to claim 1, wherein said modified VWF molecule is capable of increasing the half-life of Factor VIII co-administered with said modified VWF molecule, as compared to the half-life of the Factor VIII co-administered with a native plasma-derived VWF.

* * * * *

UNITED STATES PATENT AND TRADEMARK OFFICE
CERTIFICATE OF CORRECTION

PATENT NO. : 11,155,601 B2  
APPLICATION NO. : 15/555894  
DATED : October 26, 2021  
INVENTOR(S) : Michael Moses et al.

Page 1 of 1

It is certified that error appears in the above-identified patent and that said Letters Patent is hereby corrected as shown below:

On the Title Page

Item (30), under "Foreign Application Priority Data": "15158065" should read --15158065.1--.

In the Claims

Claim 6, Column 83, Lines 54-55: "wherein the O -glycosylation" should read --wherein the O-glycosylation--.

Claim 7, Column 84, Lines 30-31: "wherein the O -glycosylation" should read --wherein the O-glycosylation--.

Signed and Sealed this  
Eighth Day of March, 2022

Drew Hirshfeld  
*Performing the Functions and Duties of the*  
*Under Secretary of Commerce for Intellectual Property and*  
*Director of the United States Patent and Trademark Office*